United States Patent
Beisel et al.

(10) Patent No.: US 8,870,899 B2
(45) Date of Patent: Oct. 28, 2014

(54) SELF-ASSEMBLING MAGNETIC ANASTOMOSIS DEVICE HAVING AN EXOSKELETON

(71) Applicant: G. I. Windows, Inc., Newton, MA (US)

(72) Inventors: Robert F. Beisel, Robesonia, PA (US); Peter Lukin, Norfolk, MA (US); John McWeeney, Brighton, MA (US); Marvin Ryou, Melrose, MA (US); Christopher Thompson, Needham, MA (US); Josef K. Winkler, Wayland, MA (US)

(73) Assignee: GI Windows, Inc., West Bridgewater, MA (US)

( * ) Notice: Subject to any disclaimer, the term of this patent is extended or adjusted under 35 U.S.C. 154(b) by 0 days.

(21) Appl. No.: 14/262,337

(22) Filed: Apr. 25, 2014

(65) Prior Publication Data

US 2014/0236200 A1   Aug. 21, 2014

Related U.S. Application Data

(63) Continuation of application No. 13/896,670, filed on May 17, 2013, which is a continuation-in-part of application No. 12/984,803, filed on Jan. 5, 2011.

(60) Provisional application No. 61/292,313, filed on Jan. 5, 2010, provisional application No. 61/649,248, filed on May 19, 2012.

(51) Int. Cl.
*A61B 17/08* (2006.01)
*A61B 17/11* (2006.01)
*A61B 17/00* (2006.01)
*A61B 17/122* (2006.01)

(52) U.S. Cl.
CPC ............. *A61B 17/1114* (2013.01); *A61B 17/11* (2013.01); *A61B 2017/00818* (2013.01); *A61B 2017/00876* (2013.01); *A61B 2017/1139* (2013.01); *A61B 17/122* (2013.01); *A61B 2017/00809* (2013.01); *A61B 2017/1132* (2013.01)
USPC ........................................................ 606/153

(58) Field of Classification Search
USPC .............. 606/151, 153; 600/30, 37, 101, 104; 623/23.64
See application file for complete search history.

(56) References Cited

U.S. PATENT DOCUMENTS 4,197,840 A * 4/1980 Beck et al. ............... 606/204.25
4,538,130 A   8/1985 Gluckstern et al.
(Continued)

FOREIGN PATENT DOCUMENTS

| RU | 2018266 C1 | 8/1994 |
| SU | 1708313 A1 | 1/1992 |
| SU | 1725851 A1 | 4/1992 |

OTHER PUBLICATIONS

International Search Report for PCT/US2013/041641 dated Oct. 18, 2013, 4 pages.

*Primary Examiner* — Gregory Anderson
(74) *Attorney, Agent, or Firm* — Brown Rudnick LLP; Mark S. Leonardo

(57) ABSTRACT

The invention is an implantable magnetic anastomosis device having an exoskeleton that directs self-assembly. The design allows the device to be delivered in a linear configuration using a minimally-invasive technique, such as endoscopy or laparoscopy, whereupon the device self-assembles into, e.g., a polygon. A coupled set of polygons define a circumscribed tissue that can be perforated, or the tissue can be allowed to naturally necrose and perforate. The device can be used to create anastomoses in a variety of tissues, such as tissues found in the gastrointestinal, renal/urinary, and reproductive tracts. New procedures for using anastomoses, e.g., surgical bypass are also disclosed.

23 Claims, 63 Drawing Sheets

(56) References Cited

U.S. PATENT DOCUMENTS

| | | |
|---|---|---|
| 5,300,910 A | 4/1994 | Unkelbach et al. |
| 5,595,562 A | 1/1997 | Grier |
| 5,690,656 A * | 11/1997 | Cope et al. .................... 606/153 |
| 6,129,668 A | 10/2000 | Haynor et al. |
| 6,352,543 B1 | 3/2002 | Cole |
| 6,652,540 B1 | 11/2003 | Cole et al. |
| 6,719,768 B1 | 4/2004 | Cole et al. |
| 6,932,827 B2 | 8/2005 | Cole |
| 7,760,059 B2 | 7/2010 | Higuchi |
| 8,118,821 B2 | 2/2012 | Mouw |
| 8,142,454 B2 | 3/2012 | Harrison et al. |
| 8,262,680 B2 | 9/2012 | Swain et al. |
| 8,439,915 B2 | 5/2013 | Harrison et al. |
| 8,623,036 B2 | 1/2014 | Harrison et al. |
| 2008/0051626 A1 | 2/2008 | Sato et al. |
| 2008/0200934 A1 | 8/2008 | Fox |
| 2008/0262523 A1 | 10/2008 | Makower et al. |
| 2009/0125042 A1 | 5/2009 | Mouw |
| 2010/0099947 A1 | 4/2010 | Sato et al. |
| 2011/0144560 A1 | 6/2011 | Gagner et al. |
| 2011/0295285 A1 | 12/2011 | McWeeney et al. |
| 2012/0197062 A1 | 8/2012 | Requarth |
| 2012/0259350 A1 | 10/2012 | Gagner et al. |
| 2012/0330330 A1 | 12/2012 | Gagner et al. |

* cited by examiner

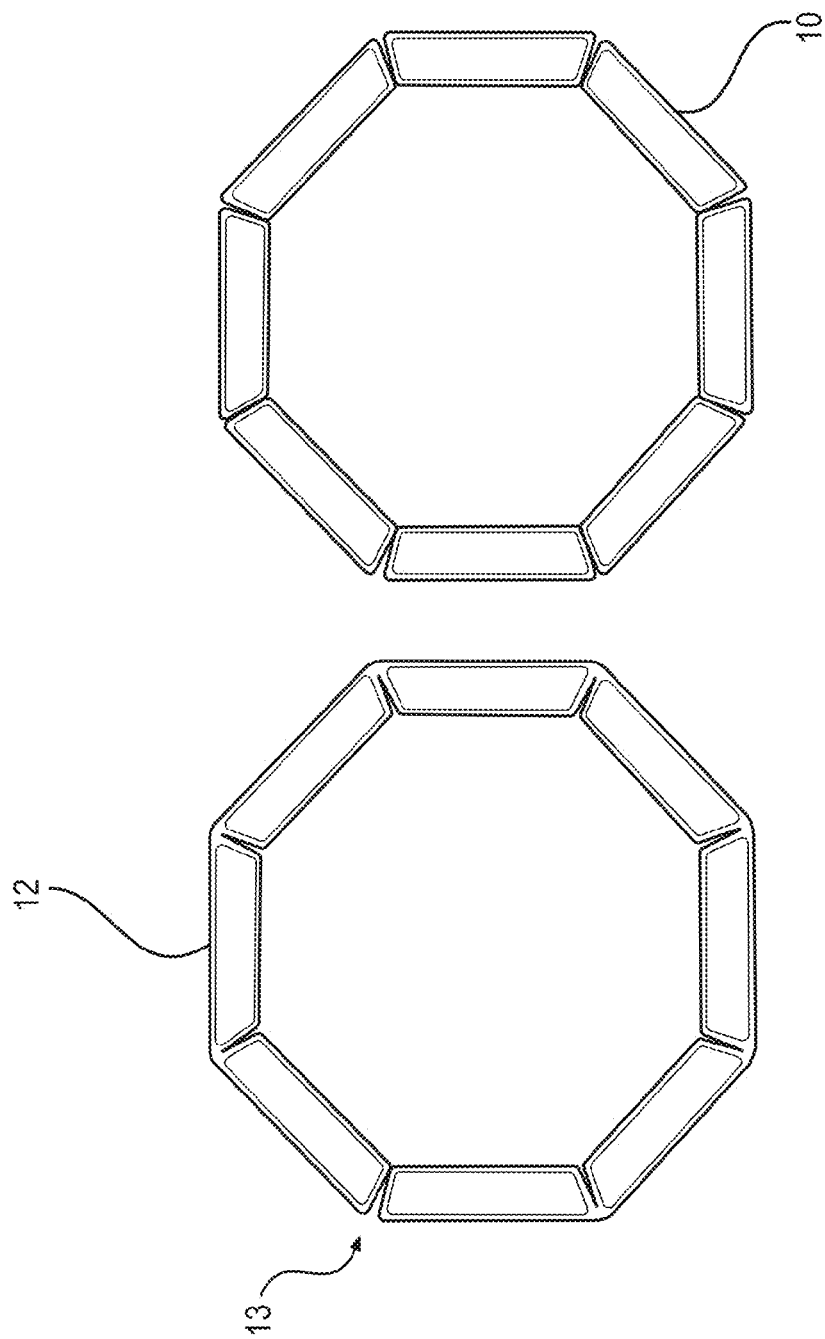

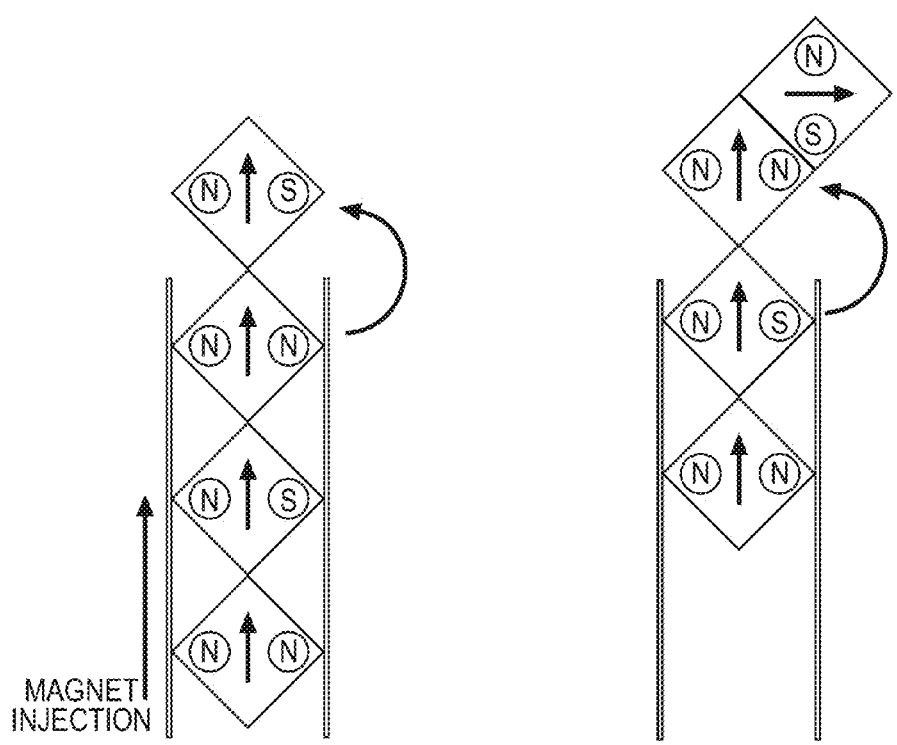
*FIG. 58A*   *FIG. 58B*

US 8,870,899 B2

SELF-ASSEMBLING MAGNETIC ANASTOMOSIS DEVICE HAVING AN EXOSKELETON

RELATED APPLICATIONS

This application is a continuation of U.S. patent application Ser. No. 13/896,670, filed May 17, 2013, which claims priority to U.S. patent application Ser. No. 61/649,248 filed May 19, 2012. U.S. patent application Ser. No. 13/896,670 is additionally a continuation-in-part of U.S. patent application Ser. No. 12/984,803 filed Jan. 5, 2011, which claims priority to U.S. Provisional Patent Application No. 61/292,313 filed Jan. 5, 2010. All of the aforementioned applications are incorporated by reference herein in their entireties.

FIELD OF THE INVENTION

The invention relates to surgical methods, apparatus and kits, especially minimally invasive endoscopic and laparoscopic techniques for creating surgical bypass ("anastomosis") using a magnetic compression device. The invention also relates to medical applications for which such a magnetic compression anastomosis device could be used.

BACKGROUND

Surgical bypass (anastomosis) of the gastroenterological (GI), vascular, or urological tracts are typically formed by cutting holes in the tracts at two locations and joining the holes with sutures or staples. The procedure is invasive, and subjects a patient to surgical risks such as bleeding, infection, pain, and adverse reaction to anesthesia. Additionally, an anastomosis created with sutures or staples can be complicated by post-operative leaks and adhesions. Leaks may result in infection or sepsis, while adhesions can result in complications such as bowel strangulation and obstruction. Additionally, while traditional anastomosis procedures can be completed with an endoscope, laparoscope, or robot, it can be time consuming to join the holes in the tissues.

As an alternative to sutures or staples, surgeons can use mechanical couplings or magnets to create a compressive anastomosis between tissues. Using surgical techniques, such as endoscopy or laparoscopy, couplings or magnets are placed over the tissues to be joined. Because of the strong compression, the tissue trapped between the couplings or magnets is cut off from its blood supply. Under these conditions, the tissue becomes necrotic and degenerates, and at the same time, new tissue grows around points of compression, i.e., on the edges of the coupling. When the coupling is removed, a healed anastomosis between the two tissues is formed.

Nonetheless, the difficulty of placing the magnets or couplings limits the locations that compressive anastomosis can be used. In most cases, the magnets or couplings have to be delivered as a completed assembly, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency, typically lasting several weeks at best.

To overcome the limitations of the mechanical or magnetic coupling devices described above, researchers have developed deployable magnetic anastomosis devices that can be delivered via a delivery conduit. Upon delivery, the devices are intended to self-assemble in useful shapes to form the anastomosis. Such devices are reported in U.S. Pat. No. 8,118,821, incorporated by reference in its entirety. Unfortunately, these designs are not sufficiently robust to be adapted for human use. In some instances, the magnetic pieces become separated from the anastomosis device, creating a risk of blockage in unintended systems. In other instances, the anastomosis devices do not self-assemble correctly and require additional surgical procedures to remove the malformed device. Regardless, previous clinical trials have met with little success. See, e.g., U.S. NIH Clinical Trial NCT00487552, terminated for failure to meet a primary endpoint.

Thus, there still remains a clinical need for reliable devices and minimally-invasive procedures that facilitate compression anastomosis formation between tissues in the human body.

SUMMARY

The invention described herein overcomes the shortcomings of the prior art by incorporating an exoskeleton that directs self-assembly of the magnetic anastomotic device, thereby assuring that the device self-assembles properly, and that magnetic segments are not dislocated or dislodged during deployment. In particular, the invention provides an implantable anastomosis device comprising a plurality of magnetic segments coupled together with an exoskeleton that directs self-assembly, e.g., made from a shape memory material, i.e., shape metal, e.g., nitinol. The device can be delivered in a low-profile, linear configuration using e.g. endoscopy, or laparoscopy, or a needle. Upon delivery, the device self assembles to form a polygon, and can be paired to a second polygon to join tissues, such as tissues of the gastrointestinal tract.

Using the devices of the invention, a wide variety of surgical procedures can be performed, including forming ports and anastomoses, as well as connecting tissues with devices such as shunts. Typically, a set of two devices will be delivered to the tissues to be joined. The devices can be delivered either with the same device (e.g., endoscope) or different devices (e.g., endoscope and needle). The mated devices will circumscribe a portion of tissue that can be perforated (e.g., with cautery) for immediate access, or the tissues can be allowed to necrose over time and form an anastomosis.

Using the disclosed anastomosis devices (or other anastomosis devices of similar functionality), it is possible to partially bypass bowel tissue so that only a pre-selected portion of the food and fluids traversing the bowel travel through the anastomosis, while the partially bypassed bowel tissue continues to function in its native capacity. By using this technique, it is possible to predetermine a ratio of native to bypassed nutrients, thereby allowing a surgeon to "dial in" an amount of bypass based upon the desired endpoints. This functionality avoids many complications that arise with more radical (e.g., bariatric) surgery, such as extreme weight loss, bacterial infection and vitamin deficiency while providing an ability to control diseases, such as diabetes, that present with a spectrum of conditions and severity.

The methods can be also used to treat diseases that require tissue removal, tissue bypass, or fluid clearance. For example, the techniques can be employed to treat cancers, gastrointestinal diseases, and cardiovascular diseases. Because the devices are relatively simple to use and can be deployed with minimally invasive tools (e.g. flexible endoscopy), the devices will save valuable OR time, and also lead to faster recoveries for patients. Furthermore, when used in the GI tract the devices do not have to be recovered in a separate procedure because the devices pass naturally through the GI tract.

Methods of forming the magnetic anastomosis devices are also described herein. The devices are simple to construct. First, the shape metal is patterned and shape-set to form an exoskeleton. Next, the exoskeleton is cooled and opened prior to inserting cooled mitered magnets inside the exoskeleton. Finally, the device is allowed to return to room temperature, whereupon the shape metal regains its resilience. In some embodiments, an adhesive is added to secure the magnets. Specific devices for shaping and opening the exoskeletons are also described.

BRIEF DESCRIPTION OF THE DRAWINGS

Other aspects, advantages and novel features of the invention will become more apparent from the following detailed description of the invention when considered in conjunction with the accompanying drawings wherein:

FIG. 26A shows eight octagon mitered segments magnetically assembled (right) next to a shape-set nickel titanium octagonal exoskeleton (left) of 0.1 mm thick superelastic sheet;

FIG. 31A shows the shape metal exoskeleton and magnet assembly prior to wrapping the exoskeleton over the magnet assemblage. FIG. 31B shows a completed magnetic anastomosis device with shape metal exoskeleton;

FIG. 32A shows the opening device in a closed position, suitable for loading a formed shape metal exoskeleton. FIG. 32B shows the opening device in an open position, suitable for opening a formed shape metal exoskeleton. In some embodiments, the shape metal exoskeleton is opened with an opening device in a bath of cold ethanol;

In FIG. 33A, a formed shape metal exoskeleton in a pinched configuration is placed on a closed opening device. In FIG. 33B, the formed shape metal exoskeleton is opened;

FIGS. 58A-58D are schematic views of a plurality of magnets in the lumen of a catheter, illustrating the process of magnetic self-assembly as the magnets are ejected from the catheter;

DETAILED DESCRIPTION

Self-assembling magnetic anastomosis is a promising therapeutic modality because it addresses several of the historical disadvantages of traditional anastomosis (discussed in Background). It allows a surgical-quality anastomosis in a minimally-invasive fashion, heretofore not possible. As described below, the invention includes devices having a plurality of small magnets that can be delivered endoscopically or laparoscopically through a delivery conduit (such as an endoscope, laparoscope, catheter, trocar, or other delivery device) whereby they reproducibly re-assemble into a larger magnet structure in vivo.

As described herein, the magnetic devices are relatively smooth and flat and have essentially uninterrupted annular faces. Because of this design, the devices do not cut or perforate tissue but rather achieve anastomosis by providing steady necrotizing pressure across the contact surface between mating polygonal rings. Because the devices include exoskeletons that direct self-assembly, the devices consistently self-assemble into the correct shape upon deployment, which greatly reduces the risks of surgical complications due to misshapen devices or premature detachment. These features also reduce the risks associated with surgical access and ensure that the anastomosis is formed with the correct geometric attributes. Overall, this ensures the patency of the anastomosis. In some embodiments, the exoskeleton is formed from a shape metal, e.g., nitinol.

As described in greater detail below, the invention discloses flexible linear magnetic devices comprising linked magnetic multipole segments that, when extruded from the end of a deployment channel or lumen, self-assemble to form a rigid, multipolar polygonal ring magnet (PRM; generally "magnetic device"). The self-assembly is directed by an exoskeleton that is capable of returning to a pre-determined shape. In some embodiments, the exoskeleton is formed from a shape metal, e.g., nitinol. The physical and magnetic structure of the deployed magnetic devices is such that when two magnetic devices approach one another, there is a rapidly strengthening attractive magnetic interaction, which creates a coupling between the magnetic devices. In some instances, it is necessary to pre-align the complimentary devices, however, in other instances the devices self-align by undergoing fast in-plane rotation with respect to one another, as discussed in detail below. As described in detail below, systems including the magnetic devices may include an endoscope having sensors that allow the endoscope to sense the position of a mating magnetic device or another endoscope that will deploy the mating device.

Figure 23:
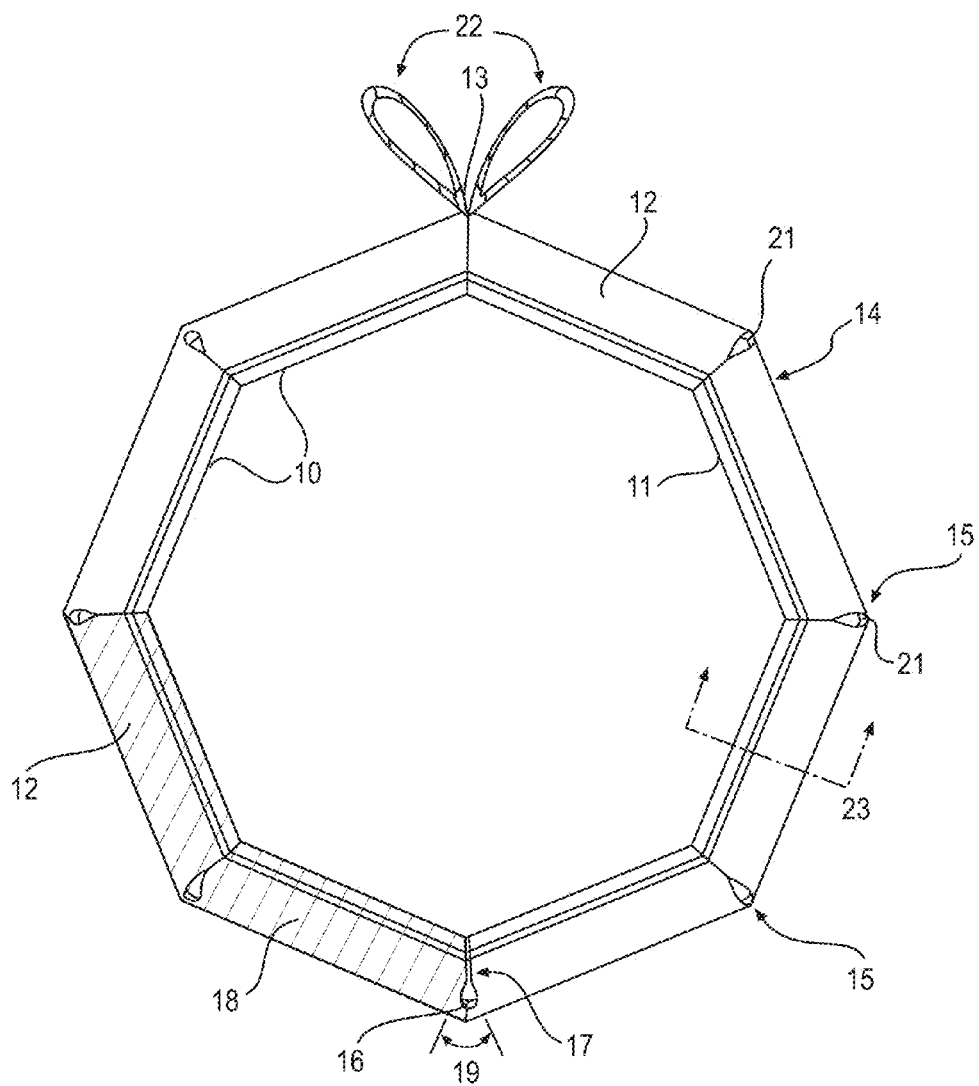
FIG. 23 is a view of an octagonal ring magnet in its deployed state.

In some embodiments, the magnetic anastomosis devices comprise shape metal, e.g., shape metal alloys (i.e. memory metal alloys) exoskeletons and mitered segments of rare earth magnets of very high coercivity, e.g., as illustrated in FIG. 23. Connecting each of the alternating dipolar segments to a single exoskeleton produces a well-behaved, self-erecting and self-closing flexible structure that can be delivered through a small orifice, such as the delivery channel of an endoscope (see, e.g., FIGS. 1 and 24). As each successive magnetic segment emerges from the end of the guiding channel into the organ lumen, the exoskeleton constrains the segment against out-of-polygonal plane deflection and the segments' mutual attractions close each miter joint in the correct inward direction, sequentially correct and, as the last segment is extruded, to close the polygonal magnetic ring. Although the exoskeletal bias and out-of-polygonal-plane stiffness is important for guiding the miter closure, the principle motive and retentive force is the magnetic attraction of the miter surfaces, by virtue of their opposite magnetic polarity. The strength of this interaction, i.e., the depth of the potential energy well into which the attracted surfaces fall, contributes to the physical integrity and stability of the polygonal ring magnet device. Furthermore, when the devices are constructed with symmetric miter joints and have their magnetic poles aligned with the annular axis of the polygon, the total magnetic force normal to the mating surfaces is maximized. The magnetic forces increase the mechanical stability of a set of coupled magnets while speeding anastomosis formation due to the intense compressive force on the trapped tissues.

During deployment, the exoskeletal hinge between magnetic segments couples the structural rigidity of individual segments similar to a cantilevered beam. In other words, the tensile modulus of the exoskeleton and the exoskeleton's resistance to out-of-plane bending allow the forces on the distal end of the structure to be distributed across the magnetic segments. The design allows a pushing force on the proximal end of the device to reliably move the distal end of the device, e.g., out of the deployment lumen. Because the exoskeleton is thin and in close contact with the magnetic segments that are long relative to the length of the miter joint, the exoskeleton can bend to accommodate miter closure with relatively small strain. However, the breadth of the exoskeleton produces a high moment of inertia (stiffness) against out-of-polygonal-plane bending, thereby giving good guidance of the growing ring and providing lateral resistance to deflection during closure. Finally, the exoskeleton also provides a tensile coupling between the magnetic segments, assuring that the segments do not go past the closure point and collapse inward or over top of one-another.

Surgical Applications

When deployed in adjacent tissues, for example adjacent organs or different regions of the same organ, the coupled magnetic devices create a compressive ring that can be surgically opened, or allowed to form an anastomosis without further intervention. When paired devices are left alone, the compressive force against the tissues collapse the vasculature and extrude fluids in the tissues, further reducing the distance between the devices and increasing the magnetic attraction. With time, the coupled devices eventually couple completely and fall away, leaving a formed anastomosis. This cascade begins when the devices approach within "capture range," whereby their mutually-attractive forces are sufficient to align the devices, trap the intervening tissue, and resist the natural pliancy of the tissues as well as the motion of the tissue under normal physiologic function.

Overall, the design specifications of the devices depend on the patient and the intended anastomosis. The design specifications may include: required capture range, desired effective inner and outer diameters of the deployed polygonal rings (e.g., as defined by the desired anastomosis size and instrument passage), thickness of the target tissue, and the inner diameter of guiding channel and the smallest radius of curvature to which the guiding channel may be bent and through which the magnets must pass. Once the design specifications are chosen, corresponding magnetic device designs can be determined, such as polygon-side-count and length, and the maximum lateral dimensions of the flexible linear magnetic structure that will be deployed through the delivery instrument.

Figure 1:
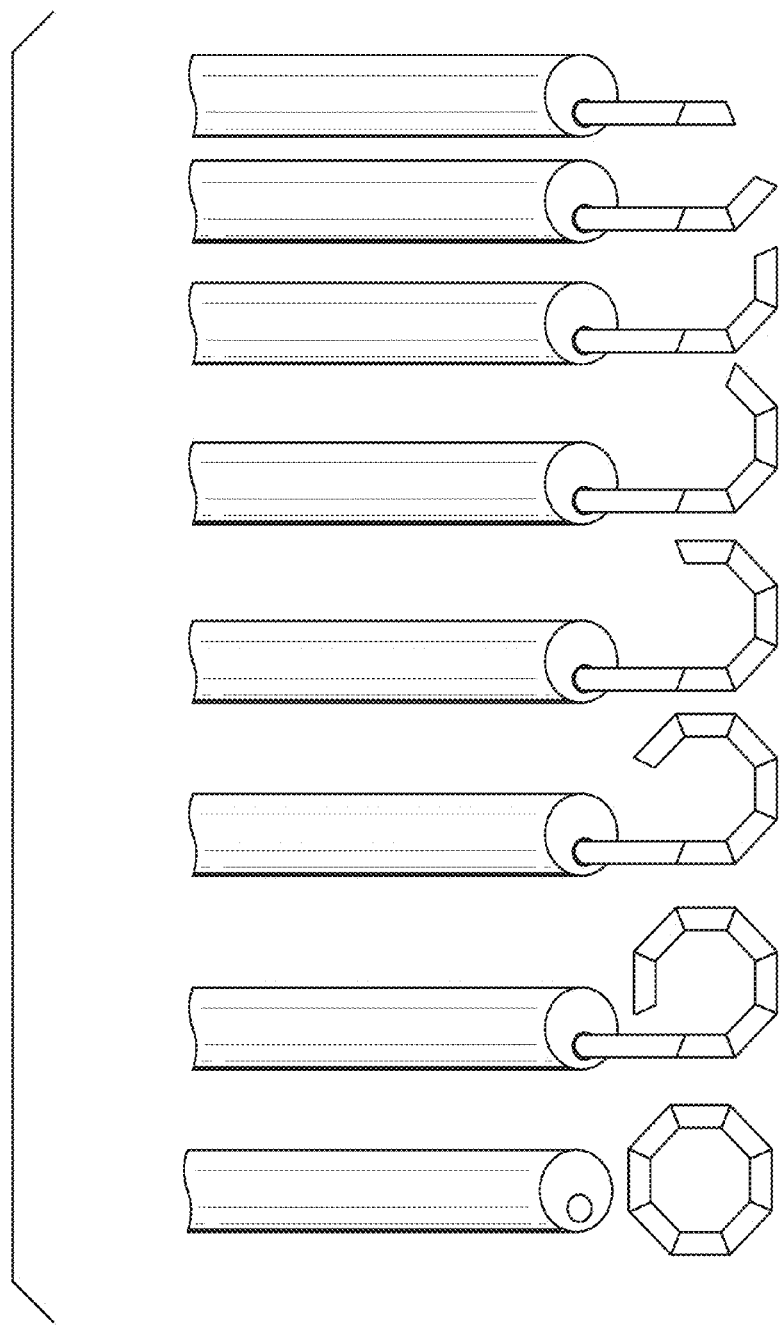
FIG. 1 shows a magnet assembly delivered through an endoscope instrument channel such that the individual magnets self-assemble into a larger magnetic structure—in this particular case, an octagon.

Deployment of a device of the invention is generally illustrated in FIG. 1. When used with the techniques described herein, the devices allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. Because the magnetic devices are radiopaque and echogenic, the devices can be positioned using fluoroscopy, direct visualization (trans-illumination or tissue indentation), and ultrasound, e.g., endoscopic ultrasound. The devices can also be ornamented with radiopaque paint or other markers to help identify the polarity of the devices during placement. In some embodiments, the devices can be positioned by use of sensors located in proximity to the delivery lumen and able to sense the position of a mating device, e.g., using a Reed switch or a Hall-effect sensor.

Figure 2A:
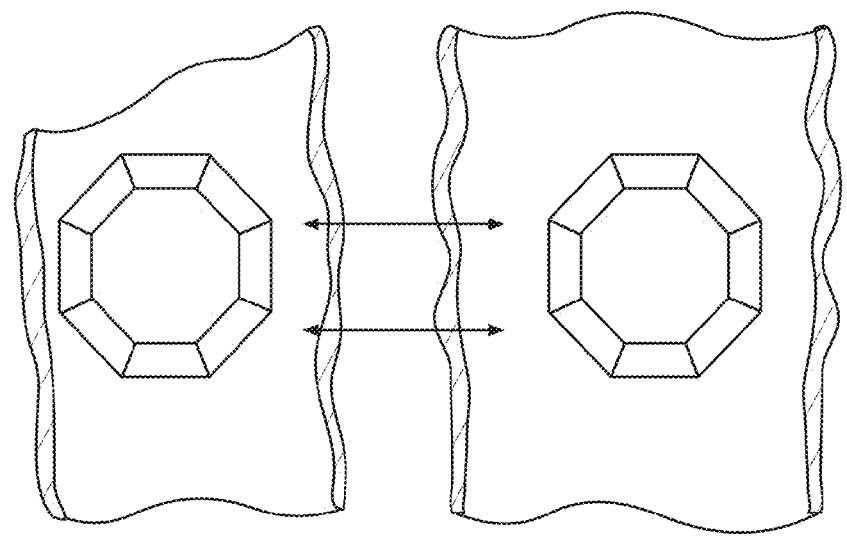
FIG. 2A shows magnet assemblies that have been delivered and deployed to adjacent tissues.
Figure 2B:
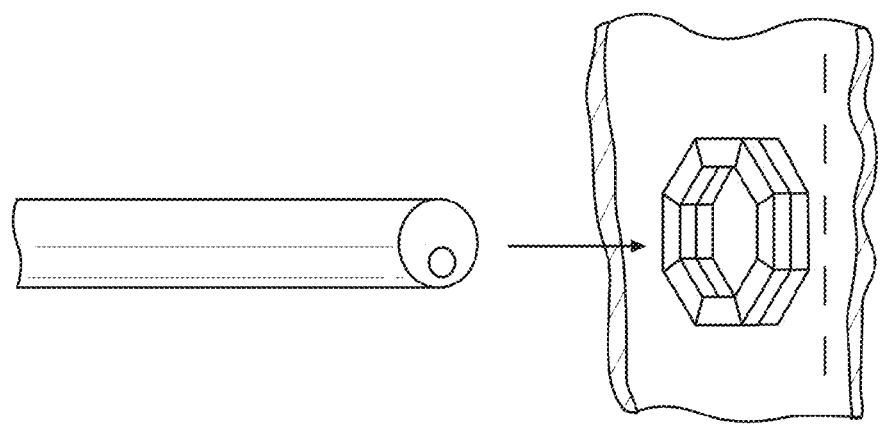
FIG. 2B shows the two magnet assemblies coupled together by magnetic attraction, capturing the intervening tissue. In some instances, the endoscope can be used to cut through the circumscribed tissue.

In general, as shown in FIG. 2A, a magnetic anastomosis procedure involves placing a first and a second magnetic structure adjacent to targeted tissues, thus causing the tissues to come together. The magnetic devices are deployed so that that opposite poles of the magnets will attract and bring the tissues together. The two devices may both be deployed inside the body, or one may be deployed inside the body and the other outside the body. Once the magnets have been deployed, the tissues circumscribed by the magnetic structures can be cut to provide an immediate anastomosis, as shown in FIG. 2B. In other embodiments, the tissues circumscribed by the devices will be allowed to necrose and degrade, providing an opening between the tissues. While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier.

As described with respect to the figures, a self-assembling magnetic anastomosis device can be placed with a number of techniques, such as endoscopy, laparoscopy, or with a catheter (e.g. not with direct visualization, fluoro, etc.). Regardless of method of device delivery, it is important to note that the procedure for creating the anastomosis can be terminated without perforation of tissue after confirmation of magnet coupling. As described previously, the compression anastomosis process can be allowed to proceed over the ensuing days, resulting in the natural formation of an opening between the tissues. The fused magnets can either be allowed to expel naturally or the magnets can be retrieved in a follow-up surgical procedure. Alternatively, if immediate bypass is required, the tissues circumscribed by the magnets can be cut or perforated. Perforation can be accomplished with a variety of techniques, such as cautery, microscalpel, or balloon dilation of tissue following needle and guidewire access.

Figure 3:
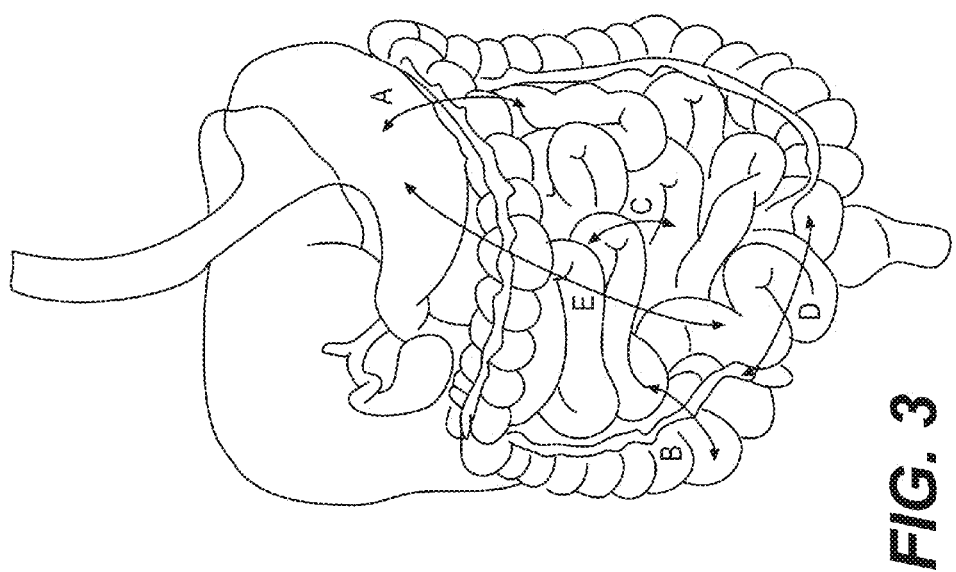
FIG. 3 shows several potential anatomical targets for anastomosis formation: Arrow A is stomach to small intestine, Arrow B is small intestine to large intestine, Arrow C is small intestine to small intestine, Arrow D is large intestine to large intestine, and Arrow E is stomach to large intestine.
Figure 4A:
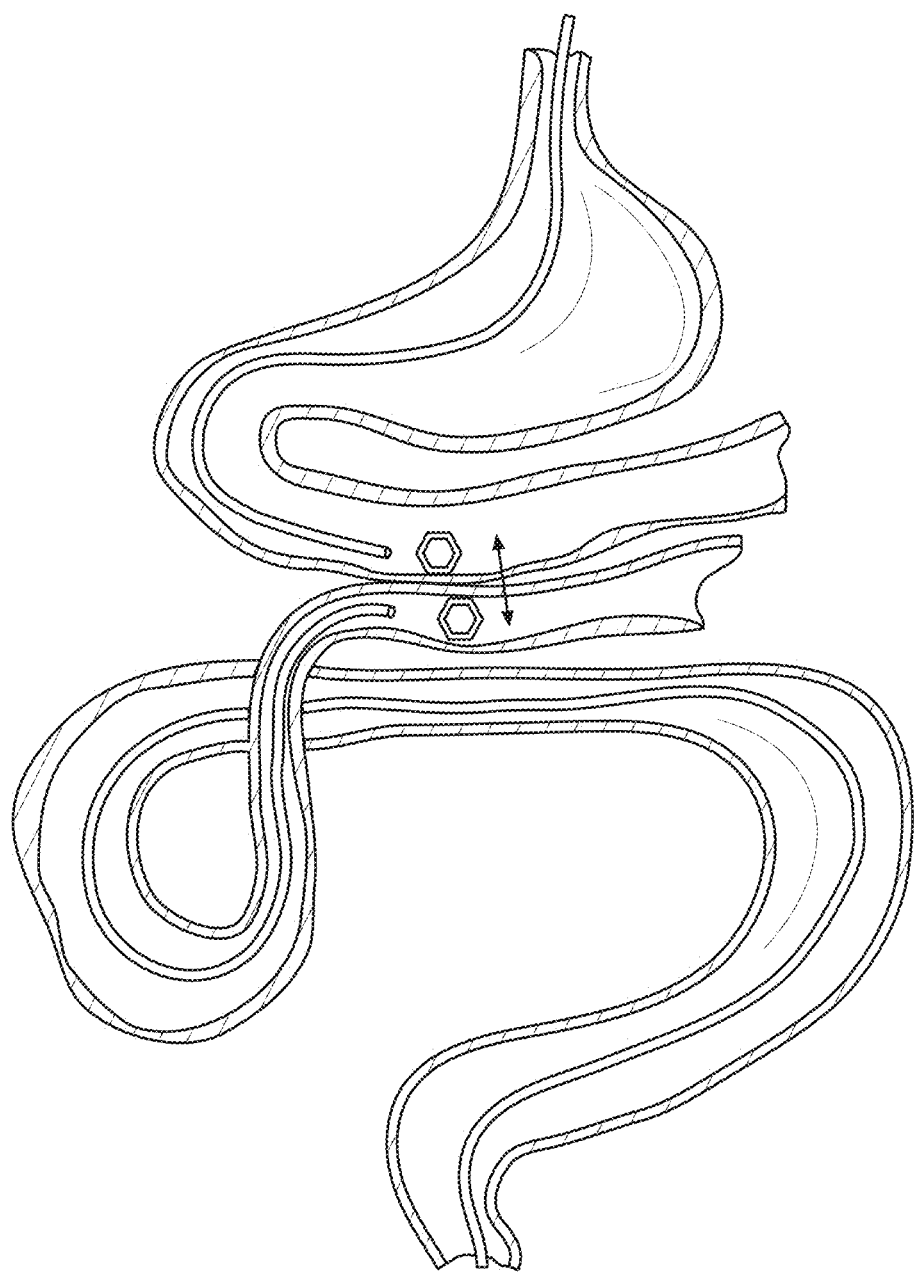
FIG. 4A shows one embodiment of delivery using two endoscopes (colonoscope and enteroscope or gastroscope) to deliver magnet assemblies.
Figure 4B:
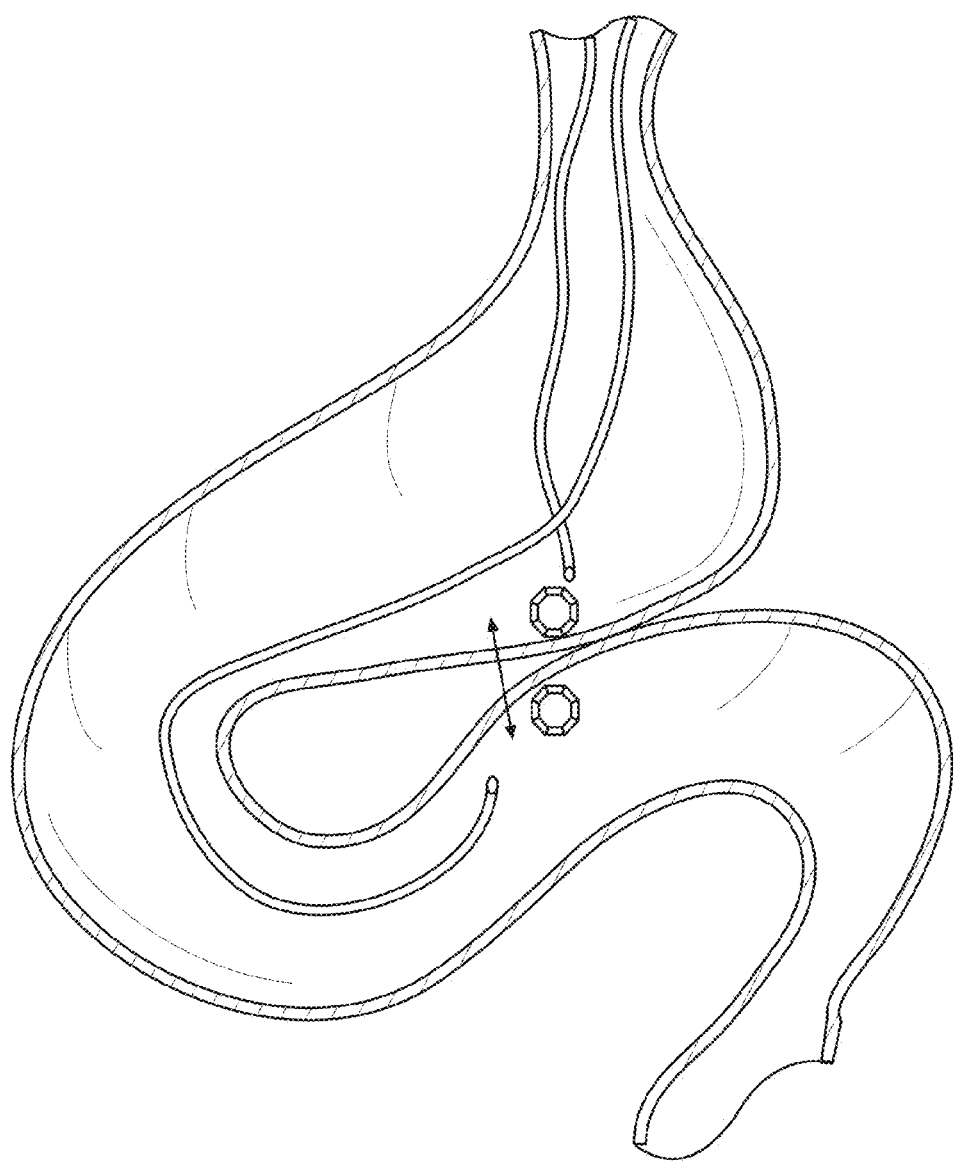
FIG. 4B shows another embodiment of delivery using two upper endoscopes both sharing per-oral entry to deliver magnet assemblies.
Figure 5:
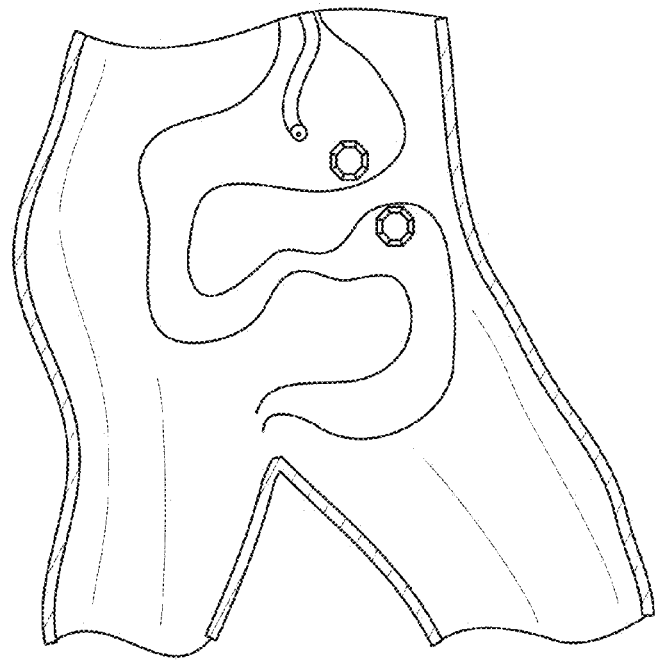
FIG. 5 shows another embodiment of delivery using a single endoscope to sequentially deliver magnet assemblies.

In some embodiments, the self-assembling magnetic devices are used to create a bypass in the gastrointestinal tract. Such bypasses can be used for the treatment of a cancerous obstruction, weight loss or bariatrics, or even treatment of diabetes and metabolic disease (i.e. metabolic surgery). Such a bypass could be created endoscopically, laparoscopically, or a combinations of both. FIG. 3 illustrates the variety of gastrointestinal anastomotic targets that may be addressed with the devices of the invention: stomach to small intestine (A), stomach to large intestine (E), small intestine to small intestine (C), small intestine to large intestine (B), and large intestine to large intestine (D). In an endoscopic procedure, the self-assembling magnetic devices can be delivered using two simultaneous endoscopes, e.g., an upper endoscope or enteroscope residing in the upper small intestine, and a colonoscope residing in the lower small intestine, as shown in FIG. 4A. Alternatively, as shown in FIG. 4B, two simultaneous upper endoscopes (one residing in the stomach and the second in the small intestine) can be used to place the devices. In other embodiments, the self-assembling magnets can be delivered sequentially through the same endoscope, which has been moved between a first deployment position and a second deployment position. For example, in FIG. 4A, a single per-oral endoscope could deliver and deploy one self-assembling magnet in the small intestine, withdraw, and then deploy the second reciprocal magnet in the stomach. Again, magnet coupling would be confirmed using fluoroscopy. FIG. 5 illustrates removal of a single endoscope after placement of two magnetic devices.

A variety of techniques can be used to detect the first deployed magnetic device to assist placement of the second mating structure. Once the first device is deployed at the desired anastomotic location, the two deployed magnetic devices need to find one another's magnetic field so that they can mate and provide the compressional force needed to prompt formation of an anastomosis. Ideally, the frames can be roughly located within several cm of one another (e.g., using ultrasound), at which point the magnets will self-capture and self-align. Where this is not possible, one of the following techniques can be used. A first location technique involves a direct contact method using two endoscopes. Here an endoscope's displacement in an adjacent lumen creates a displacement seen by another endoscope in the adjacent lumen. The displacement identifies a potential intersection point for an anastomosis location. For example, a magnetic deployment tool (described below) will be deflected by the presence of a deployed device on the other side of a tissue wall.

The second location technique involves trans-illumination, whereby high intensity light from one endoscope is directed at the lumen wall of the proposed anastomosis site. Using this technique, another endoscope in the adjacent lumen looks for the light, which diffuses through the lumen wall and projects onto the wall of the adjacent lumen. This light represents the potential intersection anastomosis point. A cap or lens can also be placed over the light emitting endoscope to further intensify and pinpoint the proposed intersection point. A similar technique could use radio-wave- or ultrasound-transducers and receivers to collocate the endoscope tips. In some embodiments, a system may include an endoscope having a sensor and a magnetic anastomosis device for deployment using the endoscope.

A third location technique involves magnetic sensing techniques to determine the proximity of the deployed ring magnet in the adjacent lumen. By maximizing the magnetic field being sensed, the minimum distance between the adjacent channels can be identified. The magnetic sensor can be carried on a probe inserted down the working channel of the endoscope and utilize common magnetic sensing technology such as a Hall Effect Sensor or Reed switch.

With trans-illumination and magnetic sensing, an additional accessory may also assist with delivering magnetic devises to a precise anastomosis site. A radially expanding ring structure can be deployed with the endoscope or laparoscope that can press fit and seat itself on the scope's outer diameter. The outer diameter of this expanding element is sized to allow the deployed device to seat itself on this expanding element (again likely a press fit). With this expanding element and magnetic device radially seated about the endoscope axis, the endoscope can be directed to the ideal anastomotic location through direct contact, trans-illumination, or magnetic sensing, and then the mating magnet device released when the anastomosis site is identified.

Figure 6:
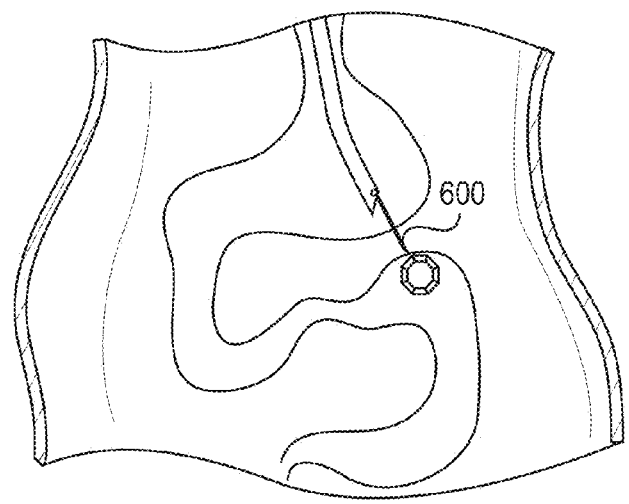
FIG. 6 shows another embodiment of delivery using endoscopic ultrasound guided needle delivery of one magnet assembly into lumen #1 followed by deployment to of the second magnet assembly in lumen #2.

In other embodiments, the self-assembling magnet devices would be delivered using ultrasound guidance, e.g., endoscopic ultrasound. For example, using an echoendoscope in the stomach, a suitable small intestine target could be identified. As shown in FIG. 6, a delivery needle 600 (e.g., an aspiration needle) or catheter can be used to access to the small intestine target and deliver the self-assembling magnets into the small intestine lumen. The delivery can be guided with fluoroscopy or endoscopic ultrasound. Following self-assembly, these small intestine magnets would couple with a second set of magnets deployed in the stomach. The two devices can be delivered with the same needle or with different needles. It is also possible to deliver the first device with an endoscope and the second device with a needle or vice versa.

Figure 7:
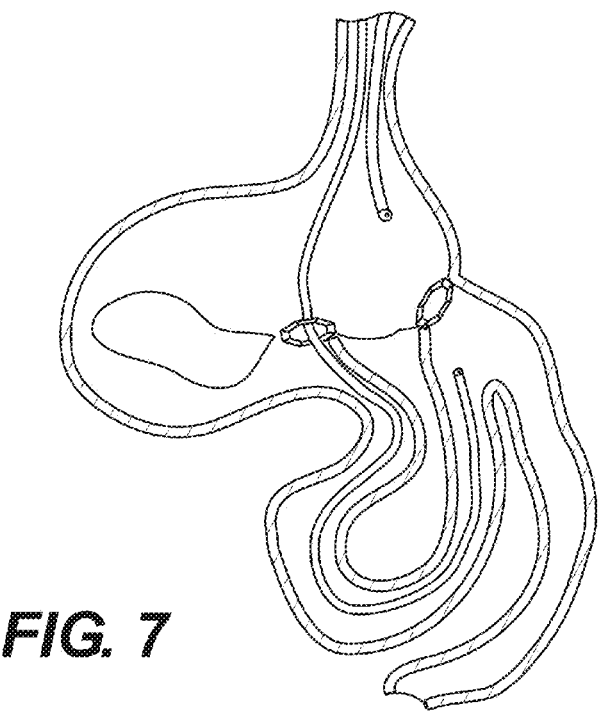
FIG. 7 shows the creation of a preliminary anastomosis to serve as a conduit for deeper endoscope delivery in order to create subsequent multiple anastomoses.

In another embodiment, illustrated in FIG. 7, a first anastomosis, created in an initial procedure, can be used to provide access for the creation of a second anastomosis. This process could theoretically be repeated multiple times to create additional anastomoses. For example, a gastrojejunal anastomosis (stomach to mid-small intestine) could serve as a conduit for the creation of a second, more distal gastrojejunal anastomosis. Ultimately, in this particular scenario, the stomach would have several bypasses to the small intestine. Additionally, in some instances, more anastomoses could be added to "titrate" to a specific clinical effect (e.g. lower glycosylated hemoglobin in type 2 diabetes). In alternative embodiments, an anastomosis may be placed to give access for a different type of surgery, e.g., tumor removal.

Figure 8:
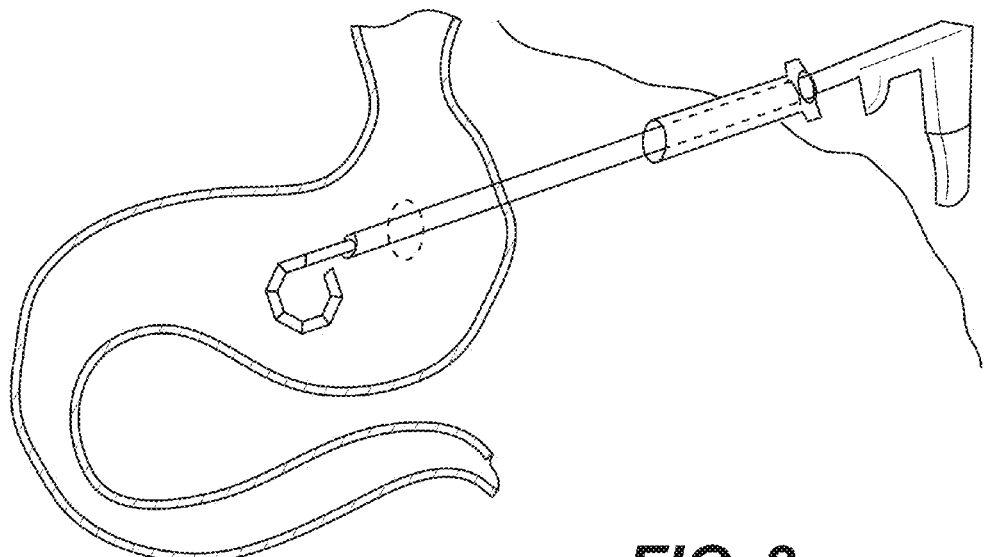
FIG. 8 shows laparoscopic magnet device delivery into a lumen (stomach, in this example)

In another embodiment of delivery, the self-assembling magnets could be delivered laparoscopically through a surgical incision into the target organs (e.g., stomach and small intestine) and allowed to couple to create an anastomosis, as shown in FIG. 8. Again, this procedure could be directed with fluoroscopy or ultrasound and the procedure can be purely laparoscopic, or a combination of endoscopic and/or laparoscopic and/or needle procedures.

Gastrointestinal anastomoses can be used to address a number of conditions. An anastomosis or series of anastomoses between the proximal bowel and distal bowel may be used for treatment of obesity and metabolic conditions, such as Type II diabetes and dyslipidemia. The procedure can also be used to induce weight loss and to improve metabolic profiles, e.g., lipid profiles. The bowel includes any segment of the alimentary canal extending from the pyloric sphincter of the stomach to the anus. In some embodiments, an anastomosis is formed to bypass diseased, mal-formed, or dys-functional tissues. In some embodiments, an anastomosis is formed to alter the "normal" digestive process in an effort to diminish or prevent other diseases, such as diabetes, hypertension, autoimmune, or musculoskeletal disease.

Using the self-assembling magnetic devices of the invention, it is possible to create a side-to-side anastomosis that does not require exclusion of the intermediate tissues, as is common with state-of-the-art bariatric procedures. That is, using the devices of the invention (or other means for creating an anastomosis) it is possible to create an alternate pathway that is a partial bypass for fluids (e.g., gastric fluids) and nutrients (e.g., food), while at least a portion of the old pathway is maintained. This design allows the ratio of "normal" to "modified" digestion to be tuned based upon the goals of the procedure. In other words, using the described procedure, a doctor can choose the ratio of food/fluids shunted down the new (partial) bypass versus food/fluids shunted down the old pathway. In most instances, the fraction shunted down the bypass limb will drive the patient toward the desired clinical endpoint (e.g. weight loss, improvement in glycosylated hemoglobin, improvement in lipid profile, etc.) The mechanism by which the endpoints are achieved may involve early macronutrient delivery to the ileum with stimulation of L-cells and increase in GLP-1 production, for example. The mechanism may also involve loss of efficiency of nutrient absorption, especially glucose, thereby reducing blood glucose levels. At the same time, however, the fraction shunted down the old pathway protects against known metabolic complications that can be associated with bariatric surgery such as excessive weight loss, malabsorptive diarrhea, electrolyte derangements, malnutrition, etc.

To achieve a desired ratio of bypass (e.g. re-routing food and secretions to flow down the new pathway, say, 70% or 80% or 90% or 100% of the time), the size, location, and possibly number of anastomoses will be important. For example, for a gastrojejunal anastomosis, it may be critical to place the anastomosis in a dependent fashion to take advantage of the effects of gravity. Also, instead of a round anastomosis, it may be better to create a long, oval-shaped anastomosis to maximize anastomotic size. Alternatively, multiple gastrojejunal anastomoses may be used to titrate to a certain clinical endpoint (e.g., glycosylated hemoglobin in Type II diabetes). Most of the procedures described herein may be used to place one or more anastomoses, as needed, to achieve the desired clinical endpoint. For example, the two endoscope procedures illustrated in FIGS. 4A and 4B can be used to create a partial bypass of a portion of the bowel. Based upon the desired ratio of bypassed and non-bypassed nutrients, the anastomoses shown in FIGS. 4A and 4B can be made larger, e.g. greater than 1 cm in open diameter, or several smaller anastomoses can be placed to achieve the desired ratio.

The procedure is also adjustable. For example, a first anastomosis may be formed and then, based upon clinical tests performed after the procedure, one or more anastomoses can be added to improve the results of the clinical tests. Based upon later clinical results, it may be necessary to add yet another anastomosis. Alternatively, it is possible to partially reverse the condition by closing one or more anastomosis. Because the partially bypassed tissues were not removed, they can return to near normal functionality with the passage of greater amounts of nutrients, etc. The anastomoses may be closed with clips, sutures, staples, etc. In other embodiments, a plug may be placed in one or more anastomoses to limit the ratio of nutrients that traverse the "normal" pathway. Furthermore, it is possible to close an anastomoses in one location in the bowel and then place a new anastomosis at a different location. Thus is possible to generally and tunably create a partial bypasses, or a series of partial bypasses, between portions of the bowel to achieve clinical endpoints, e.g., as described in FIG. 3.

The described procedures may also be used with procedures that remove or block the bypassed tissues, as is common with bariatric procedures. For example, a gastrojejunal anastomosis may be coupled with a pyloric plug (gastric obstruction) or another closure of the pylorus (e.g. sutured closure) to shunt food completely down the new bypass. Such procedures can be used, for example, to bypass tissue that is diseased, e.g., because of cancer.

In another category of procedures, endoscopic ultrasound (EUS) can be used to facilitate guided transgastric or transduodenal access into the gallbladder for placement of a self-assembling magnetic anastomosis device. Once gallbladder access is obtained, various strategies can be employed to maintain a patent portal between the stomach and the gallbladder or the duodenum and the gallbladder. In another embodiment, gallstones can be endoscopically retrieved and fluid drained. For example, using the described methods, an anastomosis can be created between the gallbladder and the stomach. Once the gallbladder is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g. ethanolamine or ethanol).

Figure 9A:
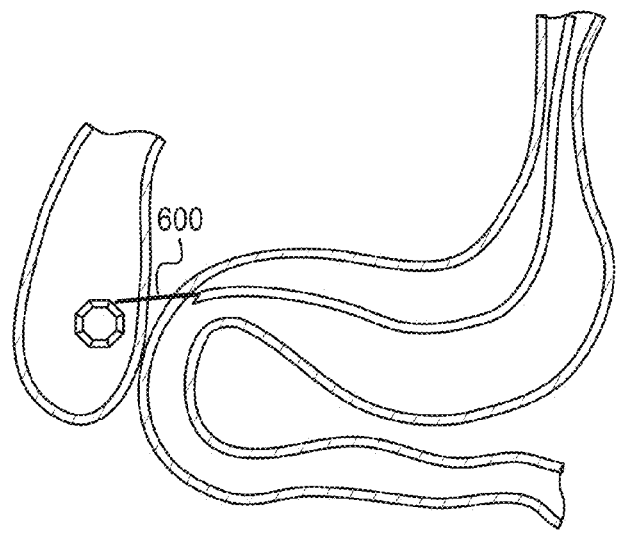
FIG. 9A shows endoscopic ultrasound guided needle delivery of a magnet assembly into the gallbladder which then couples with a second magnet assembly in the stomach or duodenum as shown in FIG. 9B.
Figure 9B:
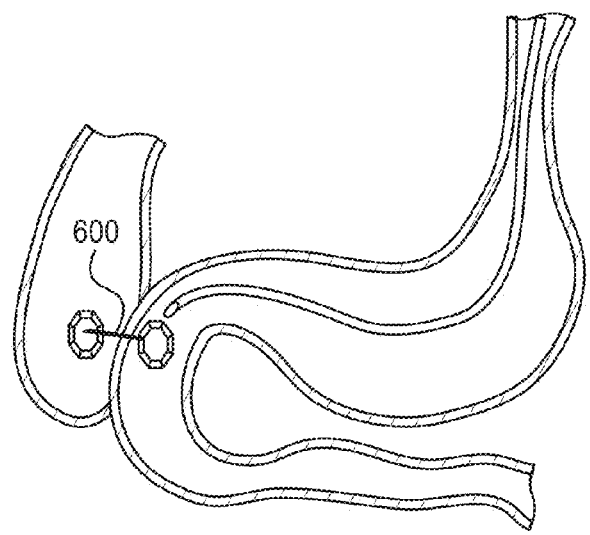

One strategy for creation of a portal is to deploy self-assembling magnets via an endoscopic needle under ultrasound guidance into the gallbladder and also into the stomach or duodenum. These magnets will mate and form a compression anastomosis or fistula. A second strategy for creation of a portal is to deploy self-assembling magnets via an endoscopic needle 600 as shown in FIGS. 9A and 9B. While the coupled magnetic assemblies are shown as octagons, the closed frame could take the shape of any polygonal structure, e.g., a square, a circle, a triangle, hexagon, heptagon, nonagon, decagon, dodecagon, etc. One such device would be deployed into the gallbladder, and the mating device would be deployed into the stomach or duodenum. In the same fashion as discussed above with respect to gastrointestinal deployment, the tissue circumscribed by the two magnetic devices can be cut with cautery, microscalpel, needle-knife, or other deployable cutting mechanism. In another embodiment, the coupled tissues can be left to necrose and form the anastomosis.

Figure 10:
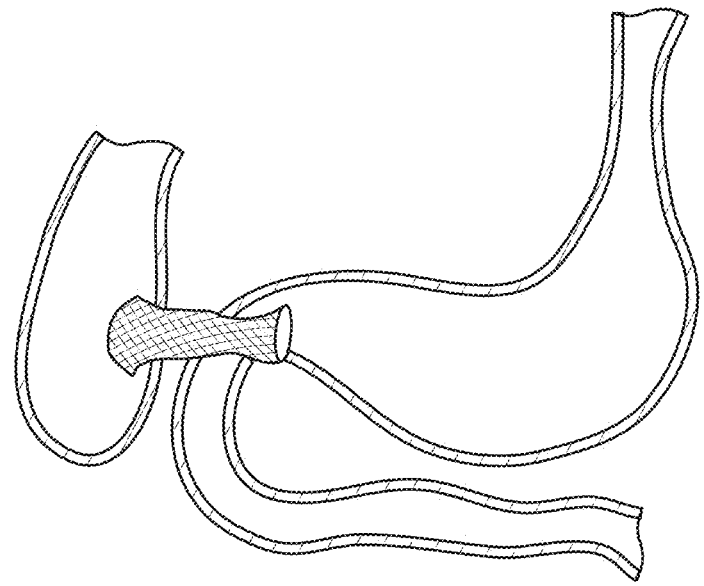
FIG. 10 shows stent deployment between the gallbladder and either the stomach or duodenum.
Figure 11:
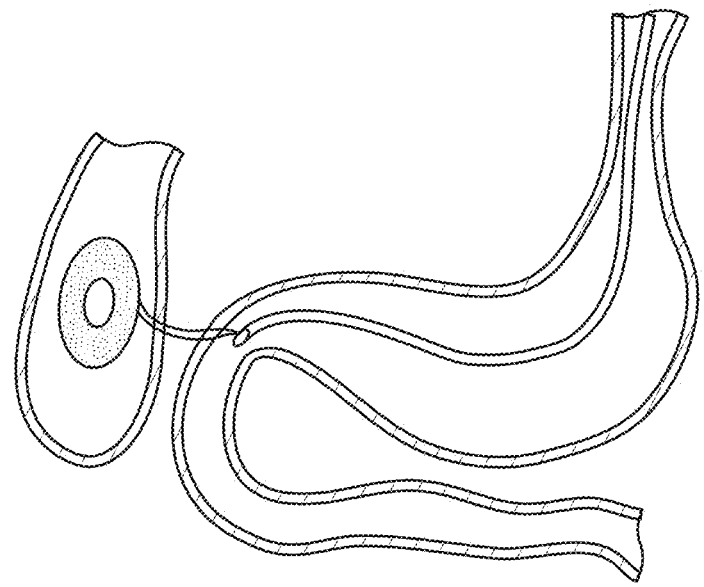
FIG. 11 shows another embodiment of an intra-gallbladder magnet assembly that is a balloon that fills with fluid, gas, or magnetic material. This balloon is tethered to the endoscope and is initially delivered through an endoscopic ultrasound guided needle.

The devices need not be limited to forming holes, however. Other structures can be coupled to one or more mating magnetic devices to created additional functionality. For example, a stent could be deployed between tissues, such as the gallbladder and the stomach, as shown in FIG. 10. Alternatively, the gallbladder magnet could be coupled to a balloon-based device that fills with air, fluid, magnetic pieces or magnetic particles. Upon inflation, the balloon would serve as an anchor in the bile duct following placement. The balloon could also have an annular configuration to allow for immediate access after coupling with the second magnet. See, e.g., FIG. 11. Regardless of embodiment, however, it is critical to contain the original access pathway within the confines of the coupled magnets, i.e., not leaving a pathway for the escape of bile. Otherwise, the opening will allow bile leakage that can result in peritonitis.

Another medical application for self-assembling magnets is direct biliary access. Currently, to achieve decompression for a malignant biliary stricture, endoscopic retrograde cholangiopancreatography (ERCP) is performed. The biliary tract is accessed endoscopically through the papilla in retrograde fashion and a stent is deployed across the stricture over a guidewire. These stents frequently require subsequent procedures for exchange, clean-out, or placement of additional overlapping stents. The need for exchange and cleaning is required to counteract the high rate of infection of the biliary tree (i.e. cholangitis) when using an ERCP procedure. Because of the high rate of morbidity, ERCP is typically limited to patients that have no other option to address pancreatic disease.

Using devices of the invention, however, it is possible to easily form an anastomosis between the bile duct (preferably the main bile duct) and either the duodenum or the stomach (choledocho-gastric and choledocho-duodenal anastomoses, respectively). This anastomosis is permanent and typically does not require intervention if located apart from the diseased tissue. In an embodiment, a biliary magnetic device is delivered directly into the bile duct under endoscopic ultrasound guidance. As described below, the self-assembling magnetic device is extruded through a needle or catheter, whereupon it deploys in the correct configuration. Using fluoroscopy or ultrasound, it is then possible to confirm that the device has self-assembled and is in the correct location. In some embodiments, the magnetic device may be tethered to the delivery needle or catheter by means of a detachable wire or suture to enable mechanical retraction until optimal positioning is confirmed.

Figure 12:
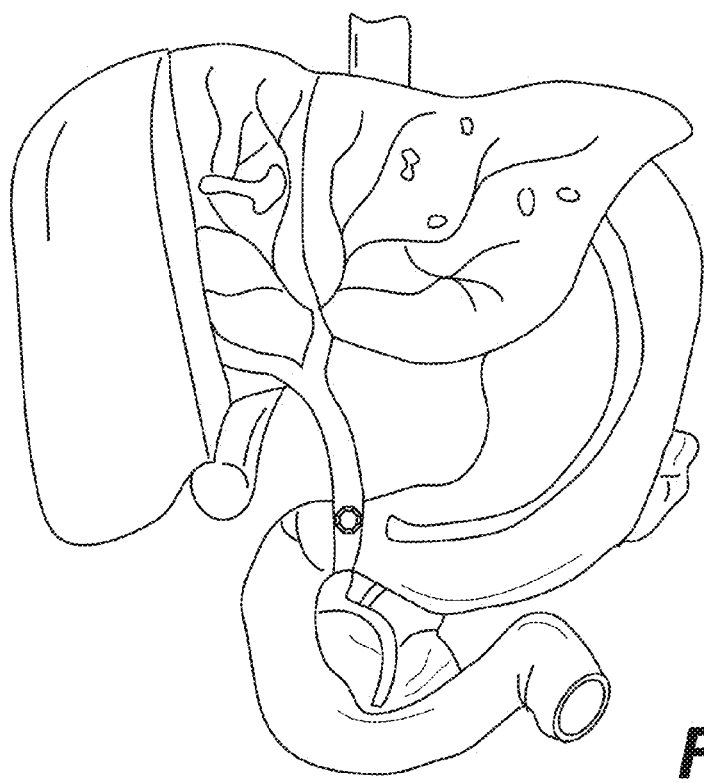
FIG. 12 shows endoscopic ultrasound guided needle delivery of a magnet assembly into the bile duct.
Figure 13:
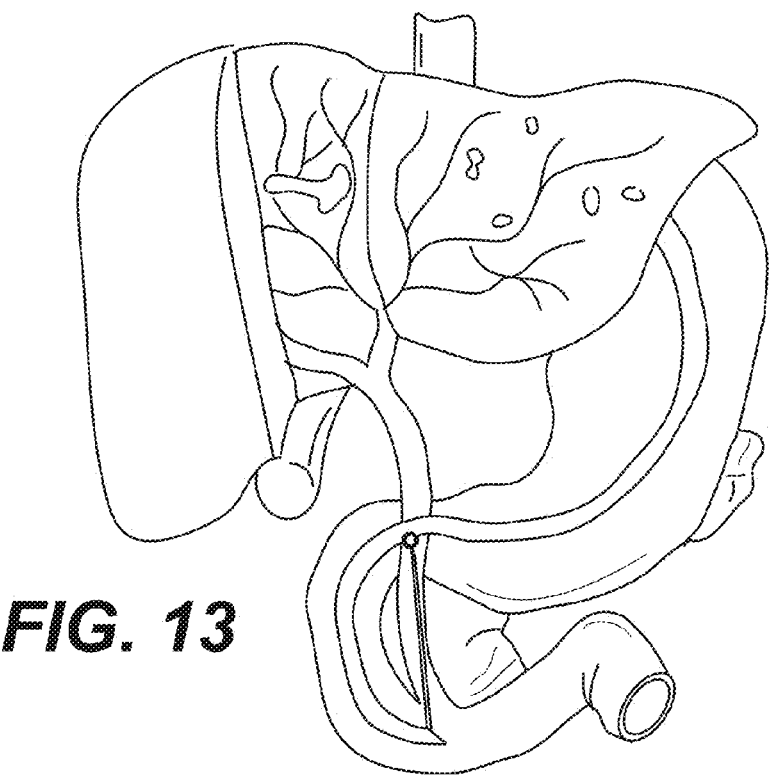
FIG. 13 shows magnet assembly delivery into the bile duct through endoscopic retrograde cholangiopancreatography techniques.
Figure 14:
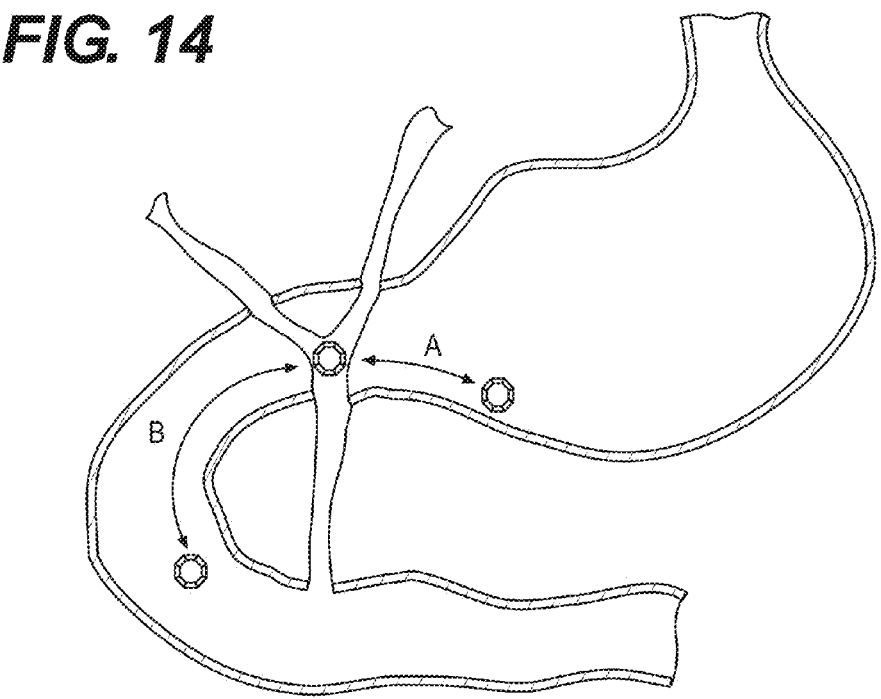
FIG. 14 shows coupling of the intra-bile duct magnet assembly with a second magnet assembly deployed either in the stomach (A) or duodenum (B)

In one embodiment, the magnetic device can be delivered endoscopically to the bile duct via wall of the duodenum, as shown in FIG. 12. In another embodiment, the biliary magnet can be delivered in conventional retrograde fashion through the ampulla into the bile duct, as shown in FIG. 13. One benefit of retrograde delivery is that it avoids needle punctures across tissue planes, as is the case with the deployment method shown in FIG. 12. Regardless of the method for delivering the biliary magnets, however, a second magnetic device is required in either the gastric (A) or duodenal (B) lumen, as shown in FIG. 14. Typically this decision is dependent upon the patient's anatomy (e.g., size of the duodenal lumen) and the location of the initial biliary magnet. In scenarios based on endoscopic ultrasound needle delivery, the second magnetic device can be connected to the biliary magnet via the aforementioned detachable wire, and therefore extruded through the same delivery needle/catheter. Alternatively, the second device can be pre-attached to the exterior of the endoscope and slid into position for coupling after biliary magnet deployment. The latter procedure may be more applicable to forward-viewing echoendoscopes but may be used with endoscopes, generally.

Figure 15:
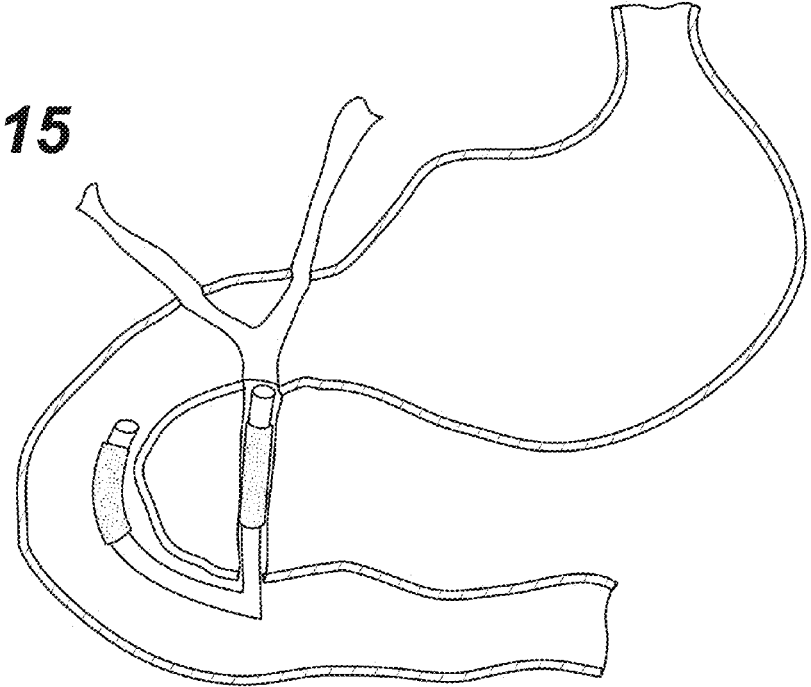
FIG. 15 shows another embodiment of bile duct magnetic anastomosis in which a hinged magnetic bile duct stent swings back onto itself by magnetic attraction to form an anastomosis between the bile duct and duodenum.

In another embodiment, the biliary magnet is a balloon-based device that fills with air, fluid, magnetic pieces or magnetic particles, similar to previously described with respect to gallbladder procedures. Upon inflation, the balloon would serve as an anchor in the bile duct following placement. In an embodiment, the balloon could have an annular configuration to allow for immediate access after coupling with the second magnet. Additionally, like the gallbladder procedures described above, a biliary magnetic device can be used with a stent form-factor. In an embodiment, the stent has an internal biliary magnet and a hinged external magnet. The stent can be inserted in retrograde fashion through the ampulla into the bile duct. The hinged external magnet can then be swung around and coupled with the internal biliary magnet to form a fistula between the bile duct and the duodenum, as shown in FIG. 15.

Figure 16:
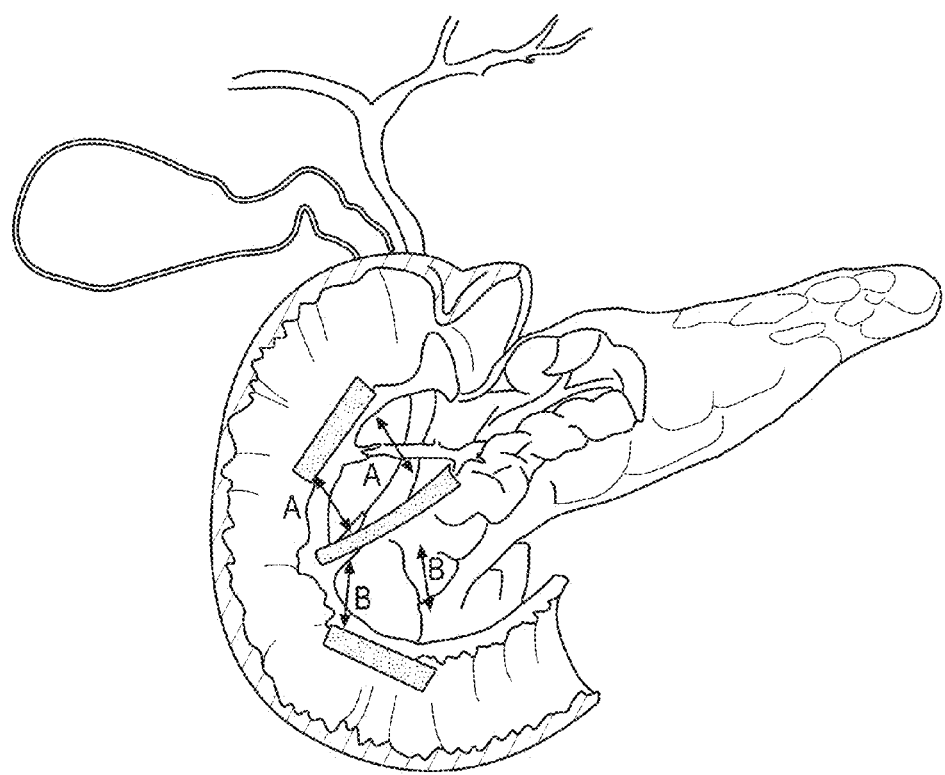
FIG. 16 shows a magnetic stent that can be delivered into the pancreatic duct. The stent can be coupled with a magnet in the stomach (A) or in the duodenum (B) to create a drainage anastomosis for the pancreatic duct.

The magnetic devices of the invention can also be used to treat pancreatic diseases. For example, the pancreatic duct requires decompression in certain disease states, such as chronic pancreatitis. Currently, extensive pancreatic duct decompression requires surgery (e.g. Peustow surgery in which the pancreas is filleted along the axis of the pancreatic duct and connected to a loop of small intestine for improved pancreatic drainage). As an alternative to Peustow surgery, extensive pancreatic duct decompression can be accomplished via creation of a large magnetic compression anastomosis between the pancreatic duct and either the stomach or duodenum using a magnetic pancreatic catheter, as shown in FIG. 16. The catheter can be magnetic along its entire length or only at certain intervals. The catheter can be in the form of a stent or straw. The pancreatic duct can be accessed using conventional ERCP methods (retrograde cannulation through the ampulla) or by direct needle access using endoscopic ultrasound (EUS). The magnetic pancreatic catheter can be delivered into the pancreatic duct and coupled with a second magnetic device in either the stomach or duodenum. As in the biliary scenario described above, the magnetic pancreatic catheter could be hinged to the second magnetic device.

Figure 17:
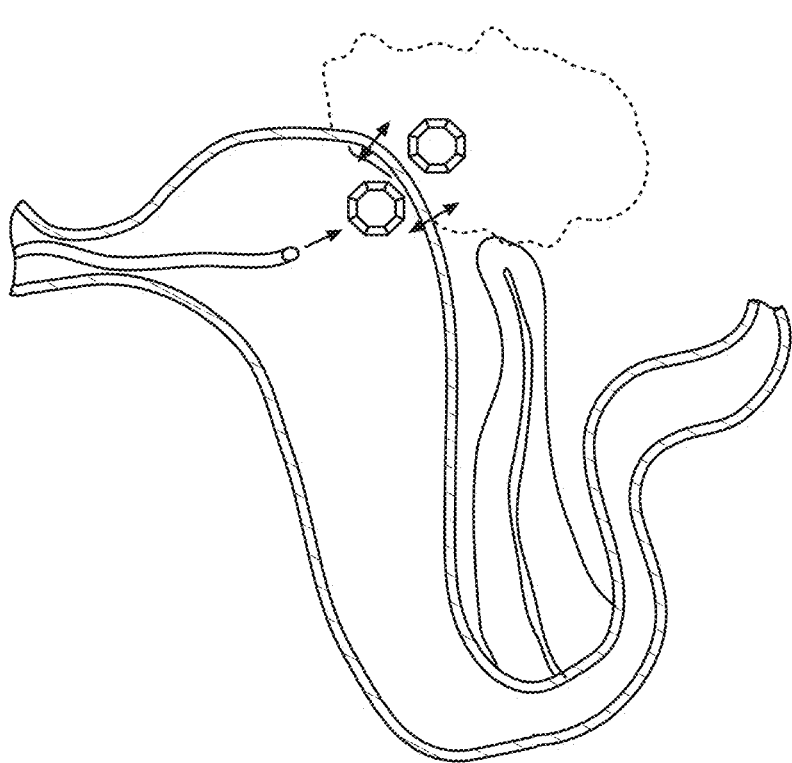
FIG. 17 shows a magnetic assembly that is delivered into a peripancreatic collection (dotted structure) using endoscopic ultrasound guided needle/catheter delivery which then couples with a second magnet assembly deployed in the stomach.

Self-assembling magnetic devices can also be used to access and drain fluid collections located adjacent to the gastrointestinal tract, as shown in FIG. 17. For example, following a bout of pancreatitis, pancreatic fluid collections can form that require drainage. While drainage can be accomplished using surgery or a percutaneous catheter, endoscopic drainage has been found to be more clinically and cost-effective, but can be complicated by bleeding, perforation, and/or inadequate drainage. As an alternative to surgical draining, magnetic devices of the invention can be delivered through a needle or sharpened catheter into the collection under endoscopic ultrasound (EUS) guidance, as shown in FIG. 17. Following assembly, the first magnetic device is coupled to the second magnetic device that has been placed in the gastrointestinal lumen (e.g. stomach). In order to speed removal after drainage, the first magnet may be tethered by a connecting wire as previously described. As described previously, the intervening tissue can be cut using electrocautery or dilation followed by needle and wire access. Additional devices, such as magnetic coupling clamps can be used to control blood flows to allow for "blood-less" endoscopic entry into the collection.

Figure 18:
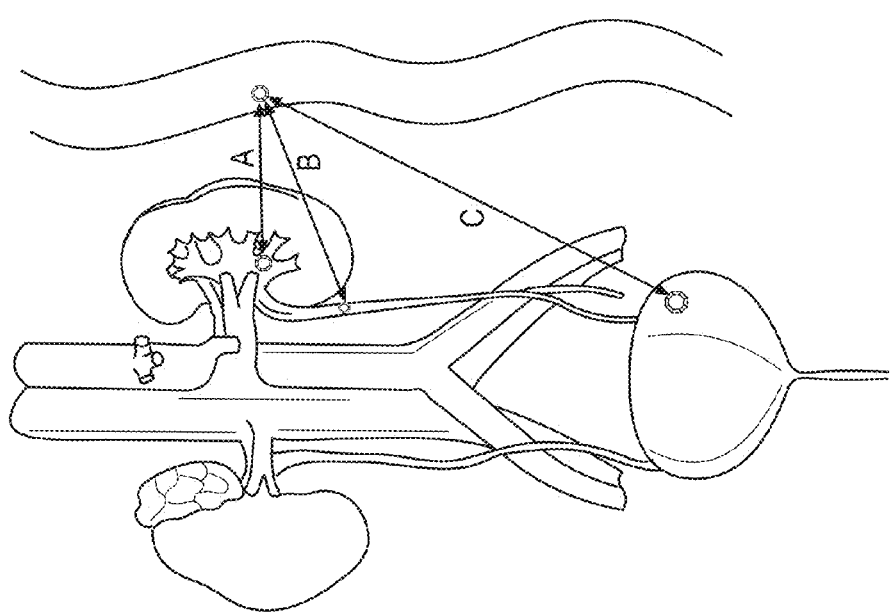
FIG. 18 shows different targets for anastomoses between the urinary system and the gastrointestinal system: renal calyx (A), ureter (B), and bladder (C)

Self-assembling magnets can also be used for urological applications such as forming bypasses to treat an obstructed urogenital tract, as shown in FIG. 18. For example a magnetic anastomosis could be created between the renal calyx and bowel (A), between the ureter and bowel (B), or between the bladder and bowel (C). Self-assembling magnetic devices of the invention can be delivered into the urological tract using an endoscope, laparoscope, or needle, as described above. The reciprocal magnetic device could be delivered into the gastrointestinal tract using an endoscope, laparoscope, or needle as previously described. In other embodiments, the devices can be used for reproductive procedures, such as bypassing a portion of obstructed fallopian tube or bypassing a vasectomy.

Figure 19:
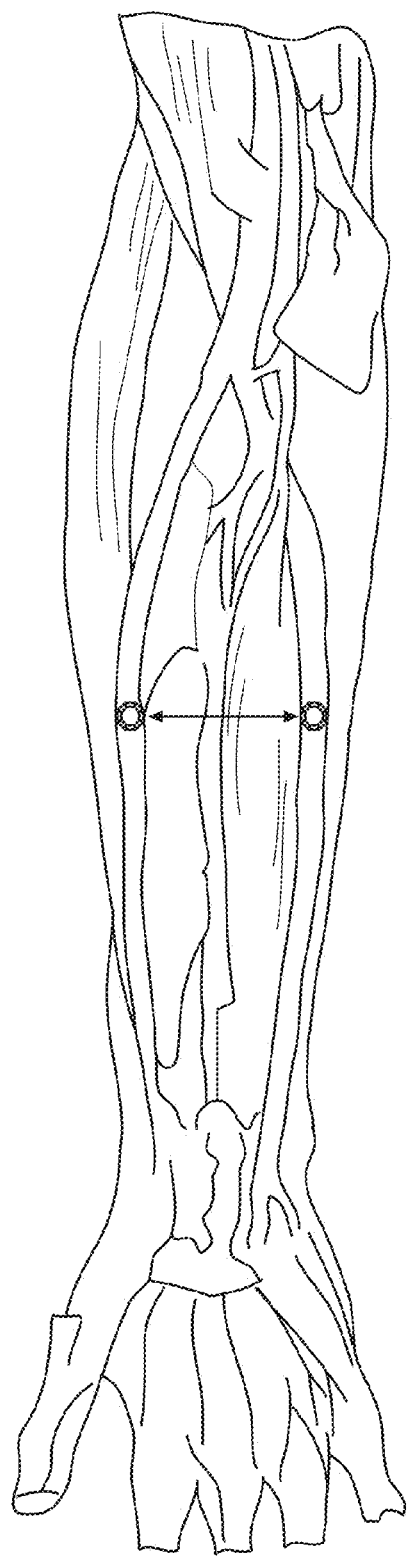
FIG. 19 shows magnet assemblies in adjacent blood vessels to couple and create a vascular anastomosis.

In yet another application, self-assembling magnetic devices can be used to create vascular anastomoses or to treat cardiac conditions. For example, a magnetic anastomosis coupling can be formed between adjacent blood vessels with magnetic devices, as shown in FIG. 19. In an embodiment, the self-assembling devices can be delivered with a vascular delivery device, such as a catheter. Additionally, as described above with respect to gallbladder and pancreatic applications, a shunt can be installed to bypass a portion of the vasculature that is weak or blocked.

Figure 20:
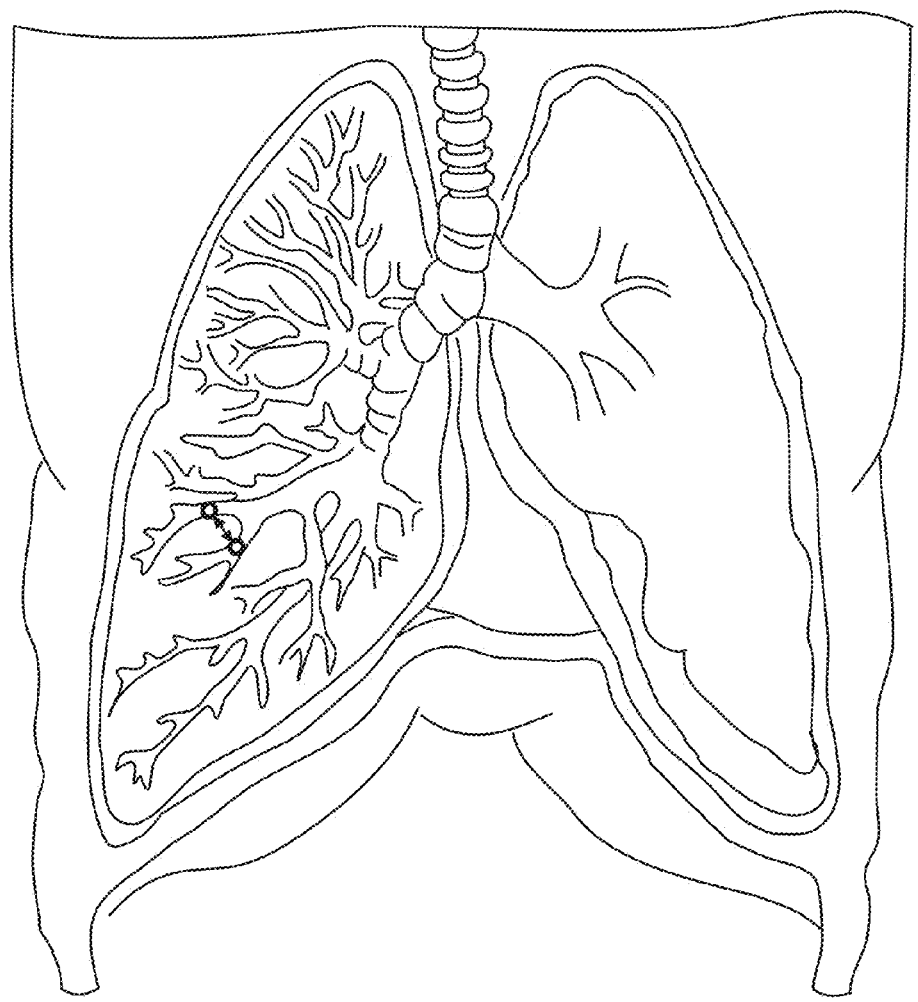
FIG. 20 shows magnet assemblies in different parts of the respiratory system to create anastomoses between adjacent bronchioles.

Self-assembling magnets can also be used for pulmonary applications such as forming bypasses in the airway to treat chronic obstructive pulmonary disease (COPD). For example, magnetic anastomoses can be created by deploying self-assembling magnetic devices into adjacent bronchioles, as shown in FIG. 20. Creation of pulmonary "bypasses" could lower airway resistance that characterizes respiratory diseases such as COPD.

Figure 21:
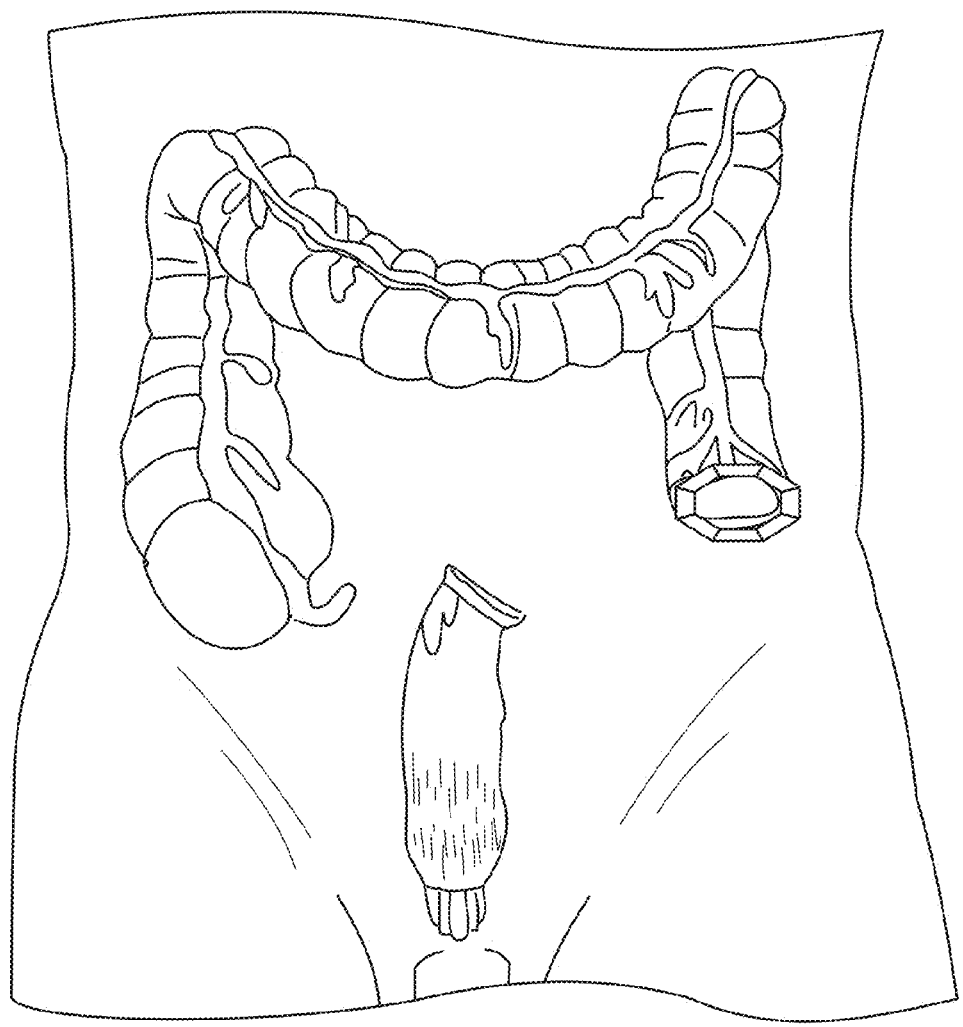
FIG. 21 shows an external magnet assembly and an internal magnet assembly within the gastrointestinal tract used to create a surgical stoma for fecal drainage.

Self-assembling magnetic devices can also be used to create surgical stomas for diversion of a fecal stream, e.g., into a colostomy bag. For example, a magnetic anastomosis can be created by deploying self-assembling magnets into the gastrointestinal tract (e.g. large intestine), as shown in FIG. 21, and then coupling the interior magnet to an external magnet worn and secured at the level of the skin. The exterior magnetic device may be coupled to yet a third magnetic device that is coupled to a collection device. Such a system allows easy removal of the collection device for cleaning, etc.

Figure 22:
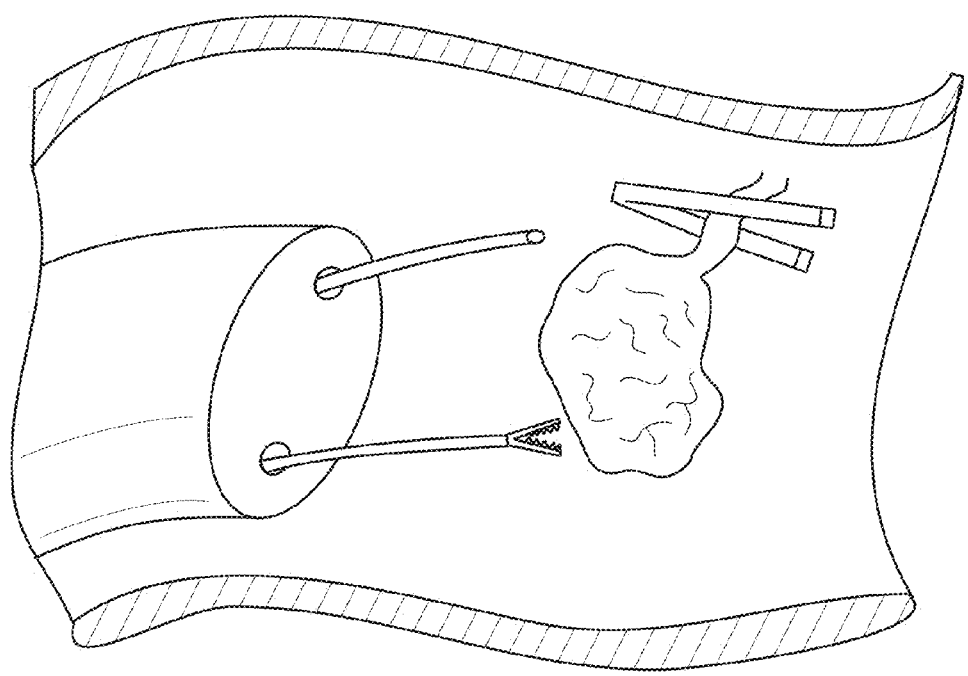
FIG. 22 shows an endoscopically delivered magnet assemblies used to clamp off the base of superficial early gastrointestinal cancer to allow for clean resection and automatic sealing of the resection site.

In other embodiments, self-assembling magnets can be used to perform deep endoscopic full-thickness resections of cancerous or pre-cancerous lesions along with simultaneous closure of the resulting defects. In some embodiments, the lesion can be tented with endoscopic traction to accommodate placement of reciprocal magnets at the base of the lesion, as shown in FIG. 22. The lesion can be resected and retrieved above the coupled magnets. The coupled magnets will eventually fuse and slough off, leaving behind a sealed resection site.

Materials and Methods of Manufacture

In general the magnetic anastomosis devices comprise shape metal exoskeletons and mitered segments of rare earth magnets of very high coercivity, e.g., as illustrated in FIG. 23. Connecting each of the alternating dipolar segments to a single exoskeleton produces a well-behaved, self-erecting and self-closing flexible structure that can be delivered through a small orifice, such as the delivery channel of an endoscope (see, e.g., FIGS. 1 and 24). As each successive magnetic segment emerges from the end of the guiding channel into the organ lumen, the exoskeleton constrains the segment against out-of-polygonal plane deflection and the segments' mutual attractions close each miter joint in the correct "inward" direction, to sequentially erect and, as the last segment is extruded, to eventually close the planar polygonal magnetic ring.

In an embodiment, the rare earth magnets comprise neodymium compounds, such as $Nd_xFe_yB_z$, and may be referred to interchangeably as "Neodymium," "NIB," or "Neo" magnets. The magnetic material is chosen to have a very high energy product $(BH_{max})$, i.e., the density of magnetic energy, which results in very strong coupling between adjacent magnets. The very high energy product allows the magnetic devices to have maximal magnetic attraction despite having a small cross-sectional size. The small sizing is required to allow the structure to be delivered down an endoscope, needle, or small lumen of a medical delivery device, e.g., as discussed above. Fortunately, neodymium magnets are both radiopaque and echogenic, which makes it easy to locate and observe the devices with medical imaging techniques such as fluoroscopy and ultrasound.

The neodymium magnets are commercially available from suppliers such as DuraMagnetics, Inc. of Sylvania, Ohio. The magnets can be ordered pre-cut and finished, or the magnets can be cut with a wire EDM machine or ID slicer and finished with a surface grinder. Typically, very high magnetic energy density magnets, such as N52 grade neodymium magnets, are used. After machining, the magnetic segments are typically plated to exclude oxygen from the reactive NIB. The plating is often predominantly nickel (either electrolytic or electroless) and often includes some amount of preplate etching, as well as an initial gold strike and a final gold finish for biocompatibility. After plating, the magnetic segments are magnetized with north and south poles on the trapezoidal faces. The magnetic segments are then assembled into a magnetic assemblage and covered with an exoskeleton, as discussed below.

Figure 25:
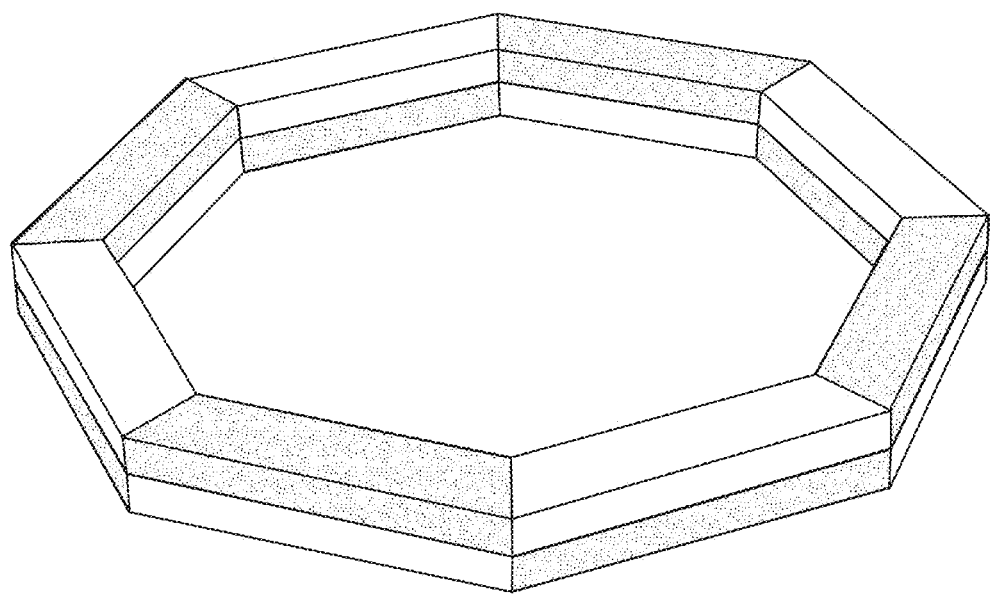
FIG. 25 is a graphic representation of the magnetic structure of the octagonal ring magnet, where shading represents opposite poles of the alternating magnetic dipole pattern of the segments.

An octagonal magnetic anastomosis device is shown in FIG. 23. The device comprises magnetic segments 10, each with the long edges chamfered, 11, and surrounded on three sides by a shape metal exoskeleton 12, e.g., a superelastic nickel titanium exoskeletal structure. The exoskeleton 12 structure has one opening gap 13, and a continuous flat band 14 surrounding the octagon's perimeter and forming a polygonal cylinder perpendicular to the plane of FIG. 23. The edge of continuous flat band 14 is visible at each miter joint 15, where the mitered edges 17 of every flange 18 abut and close to form a smooth, continuous surface. Radius 16 provides for a section 19 of adequate length to control strain to the elastic or pseudoelastic limits of the shape metal. While not shown in FIG. 23, it is understood that each segment will have two magnetic polarities (i.e., north and south) extending into and out of the page of FIG. 23. In most embodiments, the polarities of adjoining segments will be opposite, as shown in FIG. 25, however this need not be the case. As shown in FIG. 25, one pole (e.g., north) is shaded, while the other pole (e.g., south) is not.

In some embodiments, the polygon is not a regular polygon. By varying segment length and miter angle it is possible to produce complex, asymmetric shapes, although a larger volume may be needed for their deployment, erection, and closure. Additionally, it is possible to include multiple "backbones" on either side of a magnetic segment, thereby allowing for even more varied shapes, such as adjoining structures with reverse curvatures.

In some embodiments, e.g. as shown in FIG. 23, high tenacity and high tensile modulus attachment points 22 are coupled to the device. In some embodiments, the attachment points 22 are twisted or braided fibers. The fibers can be made from nitinol wire to assure that the attachment points 22 deploy from the device once the device exits the delivery instrument. The attachment points 22 will allow a surgeon to grasp, secure, enclose and/or envelope the magnetic segments 10 to provide a way to attach the flexible exoskeletal structure. The attachment points 22 can also be used to place or remove the magnetic device, as needed during the procedure.

Other features can be included in the magnetic device to provide attachment points 22. For example, holes can be placed in the exoskeleton and/or grooves placed in the magnetic segments to facilitate attaching and manipulating the magnetic devices. Furthermore, attachment points 22, such as suture loops or other securement points, can serve many purposes. For example, they can allow a deployed and assembled device to be held in place, manipulated, or moved to an alternative location. In some instances, as described with respect to FIGS. 53-55, the attachment points allow the magnetic ring to be separated, removed, or redeployed. In other embodiments, attachment points can be used by a physician to control the passage of the device(s) once an anastomosis has formed. For example, by attaching to an attachment point to tissue neighboring tissue the device is prevented from passing through an anatomical structure that may be of concern. In such embodiments, a separate procedure (e.g., endoscopy) can be used to detach the device from the neighboring tissue and remove the device(s).

Figure 23A:
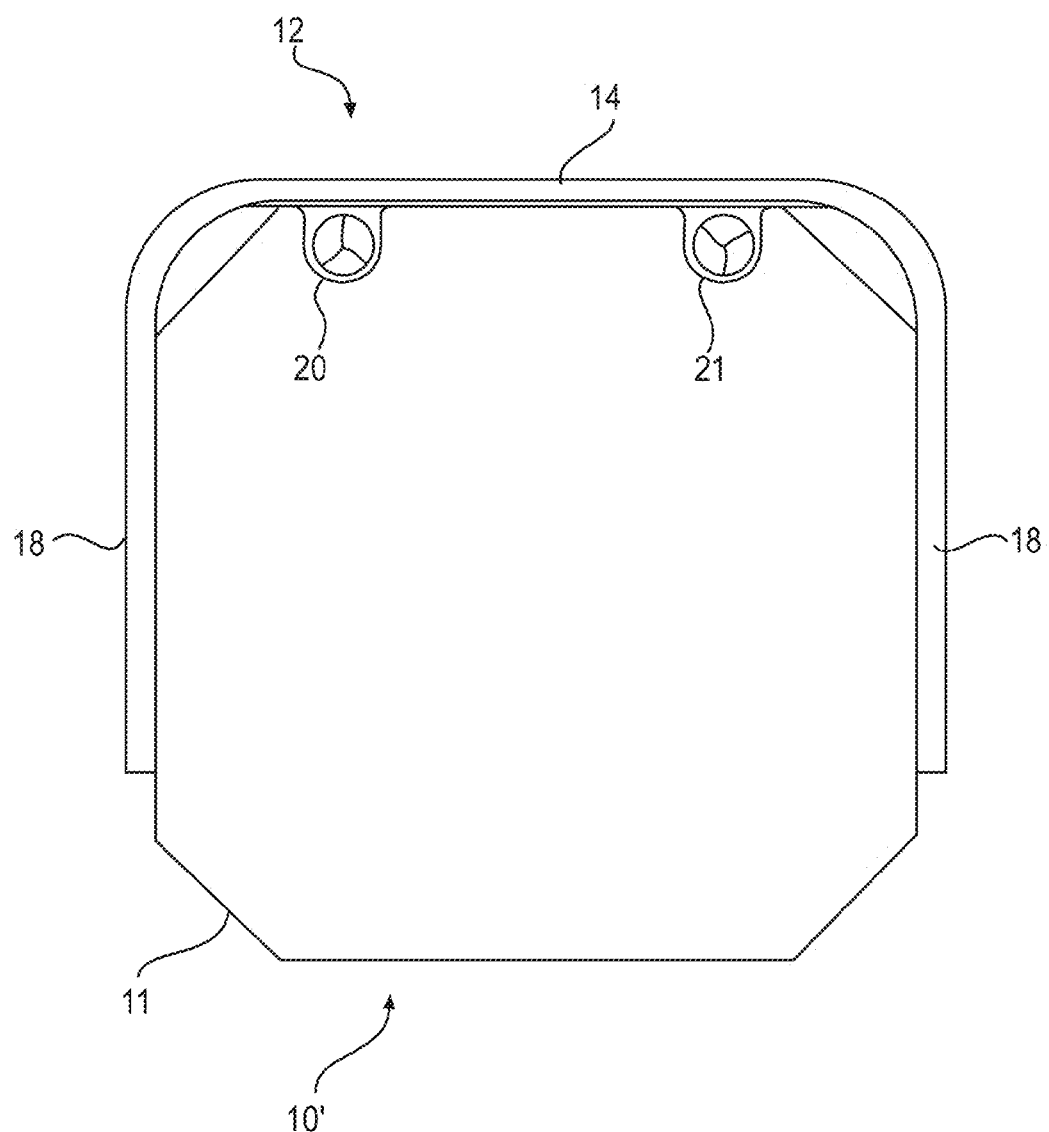
FIG. 23A is a radial section through one segment's midpoint.
Figure 23B:
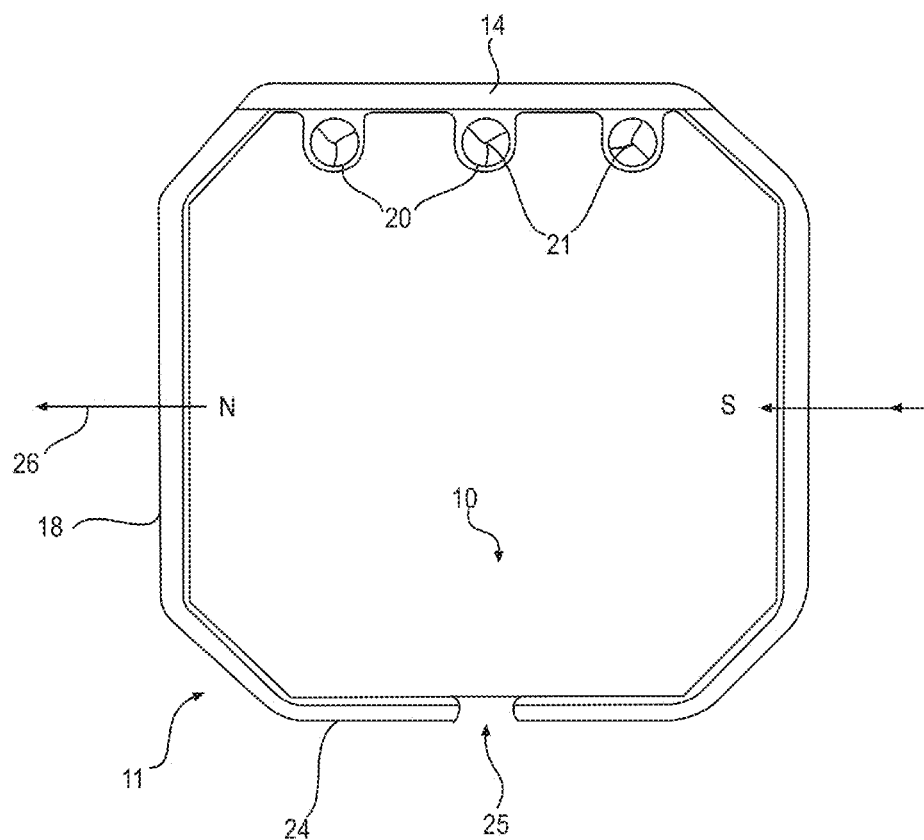
FIG. 23B is the same radial section through a segment comprising an exoskeletal member that fully envelopes the magnetic segments.

Cross sections of the magnetic device are shown in FIGS. 23A and 23B. The cross section is taken at cut-line 23 in FIG. 23. As shown in FIG. 23A, the magnetic segment 10 is surrounded on three sides by a channel formed from 0.001"-0.01" thick, e.g., 0.001-0.008" thick, preferably 0.002"-0.004" thick, more preferably 0.004"-0.006" thick superelastic nickel titanium (shape metal), i.e., making up the exoskeleton 12. The channel comprises a flat peripheral band 14 that connects adjacent segments 10, as well as lateral flanges 18 that effectively grasp the exterior of the mitered magnets that make up each segment 10. The exterior edges 11 of the mitered magnets can be radiused or, more preferably, chamfered to further improve clearance within the guiding channel, and avoid catching operative devices (e.g., needles) on the interior of the ring.

FIG. 23B depicts an alternative embodiment wherein the three-sided channel of 23A has been extended to include enveloping edges 24 that more completely couple the segments 10 to the exoskeletal structure 12. The edges 24 meet at a small gap 25 running the inside length of all segments 10. In an embodiment, small amounts of adhesive are placed in gap 25 to secure the magnetic segment to the framework. In this embodiment, the enveloping edges 24 provide robust physical protection of the magnets, and prevent the magnets from being nicked or damaged, for example as the device is extruded from the delivery device. In FIGS. 23A and 23B, the magnetic dipole axis, 26, of each segment 10 has a north and a south pole.

Figure 24:
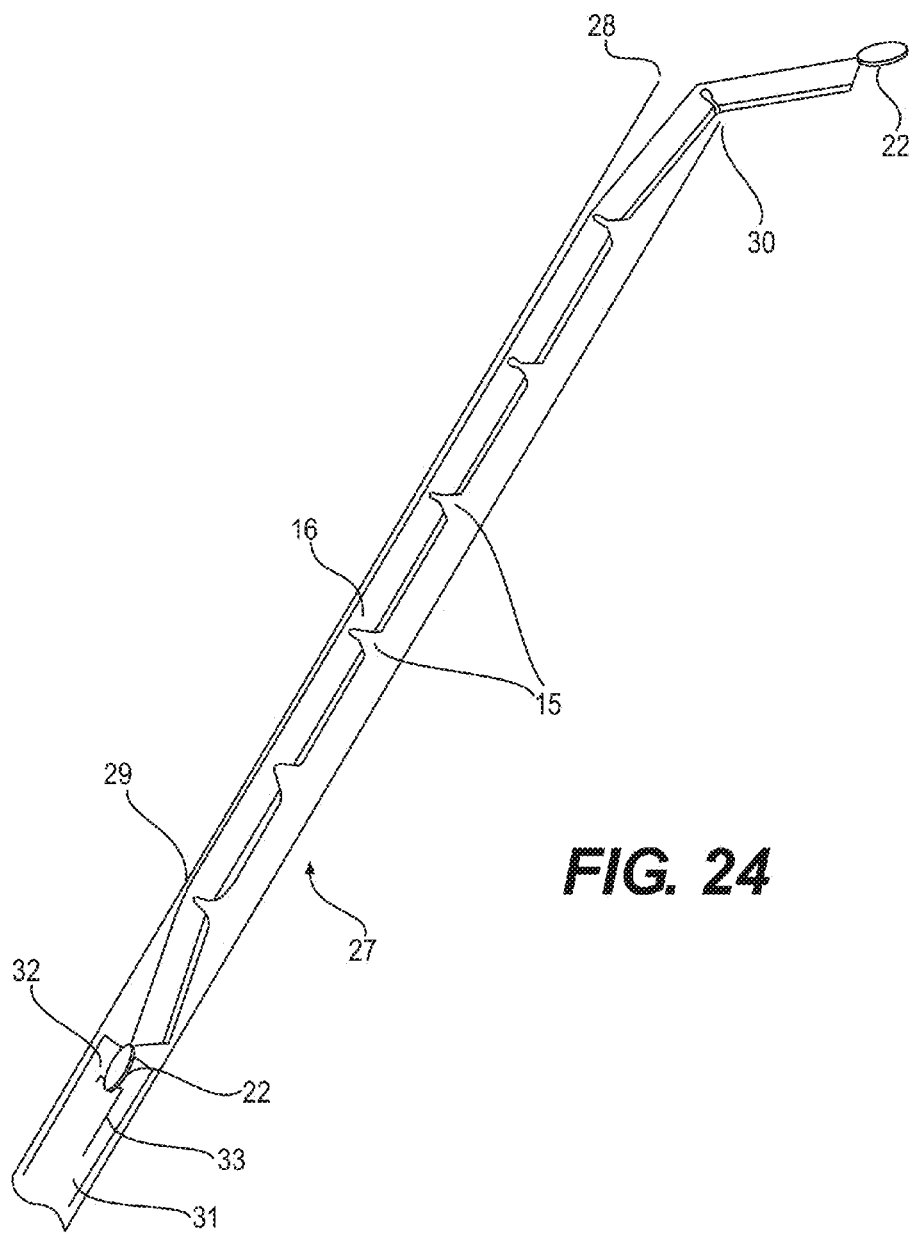
FIG. 24 is a view of an octagonal ring magnet in its delivery configuration beginning to deploy from within a delivery lumen.

FIG. 24 shows the octagonal device of FIG. 23 in an open configuration within a guiding channel 27 as the device is extruded from the channel's distal end 28. Because the exoskeleton 12 is constructed from shape metal, e.g., nitinol, the opened miter joints 15 and notch radius 16 will immediately try to close as the device leaves the guiding channel 27. The force of the shape metal is evident at both the proximal end miter 29 and the distal end miter 30 which have partially closed to their deployed configuration. In an embodiment, a central pusher 31 within the guiding channel 27 is used to extrude the device while a retaining mechanism 32, optionally controlled with a slideable element 33 reversibly engages the device's attachment point 22. For example, a suture loop passing through attachment point 22 and through a lumen within the central pusher 31 to its proximal end can be used to retain and control placement of the device.

Figure 26B:
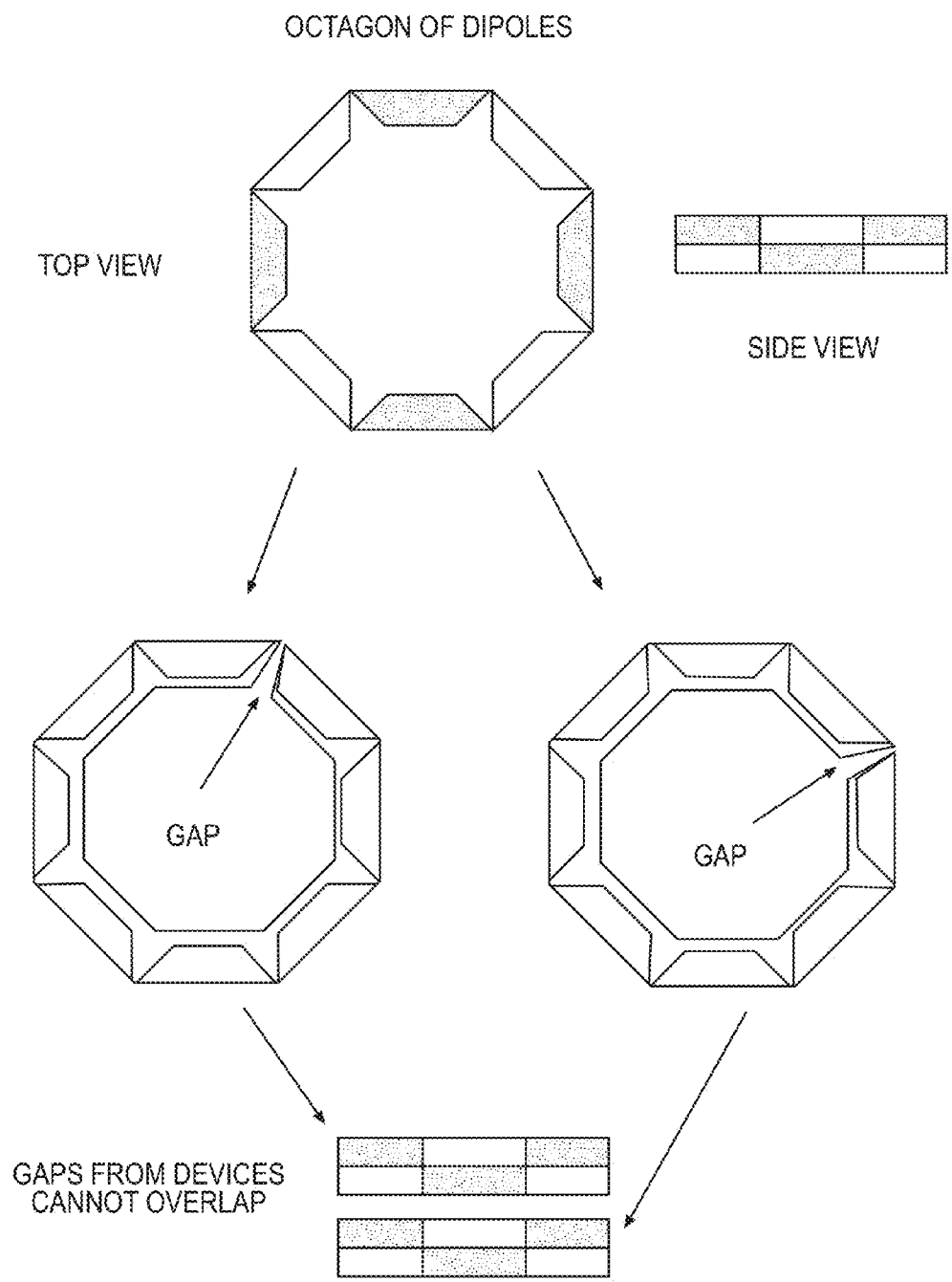
FIG. 26B illustrates that the gap in the exoskeleton can be placed in two different positions. When assembled, a matched set of two devices with gaps in different positions will not be able to have aligned openings.
Figure 26C:
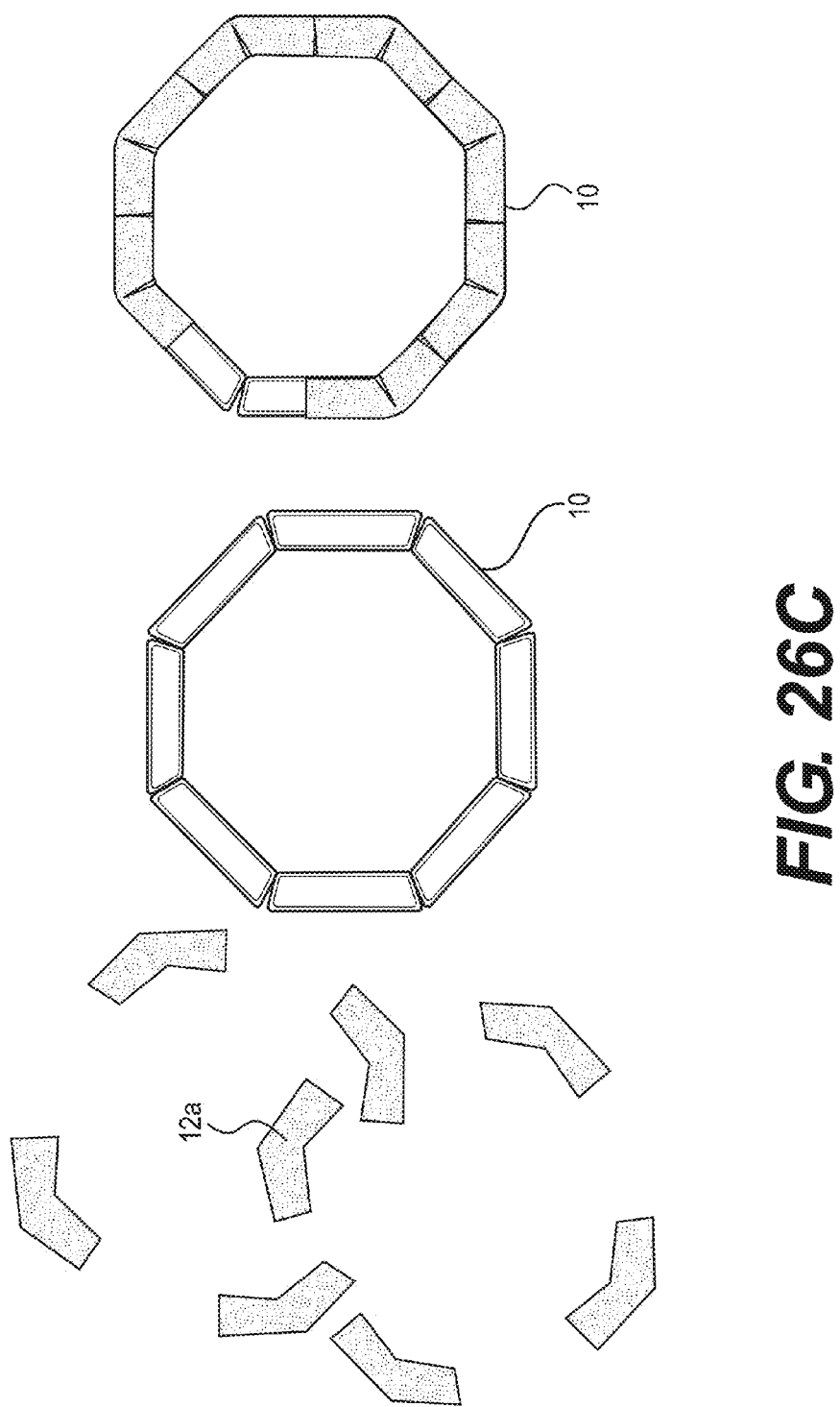
FIG. 26C shows an alternative construction in which the exoskeleton is not a continuous piece, but rather a collection of exoskeleton pieces providing structural guidance to the magnetic assemblage.
Figure 31A:
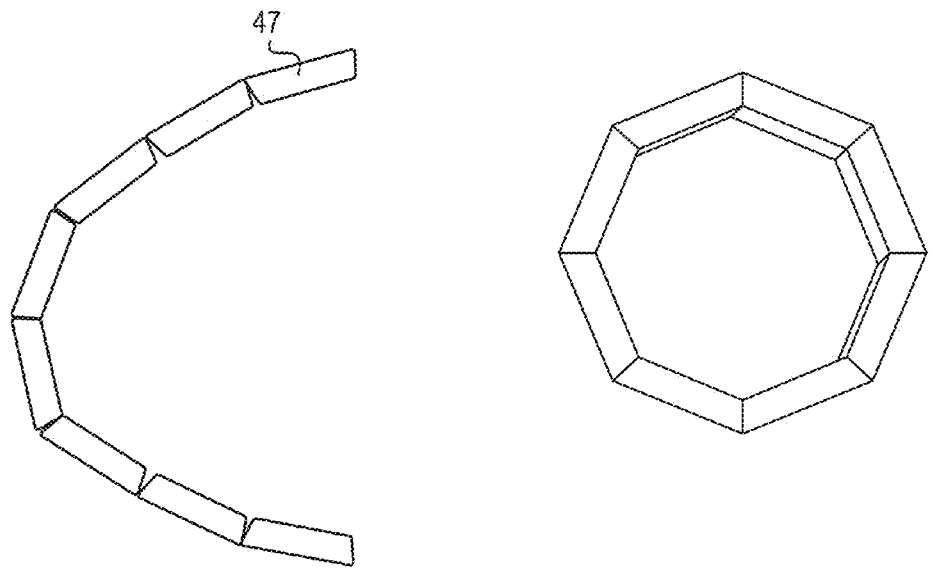
FIGS. 31A-B depict assembly of an eight segment shape metal exoskeleton and magnet assembly.

Various embodiments of the two portions of the magnetic anastomosis device, i.e., the magnet assembly and the exoskeleton are shown in FIGS. 26A-26C. On the right-hand side of FIG. 26A, a metastable assemblage of eight magnetic segments is held together by magnetic attraction alone, while on the left, a single piece, shape set, three-sided nickel titanium (nitinol) exoskeleton 12 is shown. The exoskeleton 12 has a gap 13 located at the 10:00 position, allowing the exoskeleton to be linearized for deployment with a surgical device. This octagonal NiTi exoskeleton can be channel flared and octagon opened to increase the cross-sectional clearance, and will accept into its channel the metastable magnet assemblage on its right. The devices and methods used to open the exoskeleton 12 and load the magnets are described below with respect to FIGS. 31-33.

The placement of the exoskeleton over the magnetic assemblage determines the location of the gap 13, as described in greater detail in FIG. 26B. As shown in FIG. 26B, the gap in the exoskeleton can be placed such that the there is a north pole to the left of the gap and a south pole to the right of the gap, or vice versa. The location of the gap with respect to the polarity of the magnets results in a "handedness" of the finished device in that the two devices are now non-superimposable mirror images. (There is no "right" or "left" hand for the devices, and they could as easily be termed "red" and "green", provided that the consequence of the orientation is appreciated.) One benefit of producing devices with different handedness is that when two devices of opposite handedness are assembled, it is impossible for the gaps to align. Because the gaps of the matched devices are not aligned, there is no risk that a coupled set of devices can re-open once properly deployed. Devices with handedness are not limited to octagonal dipole configurations, as other polygonal structures will also exhibit the same properties.

The exoskeletons of the magnetic anastomosis devices of the invention need not be limited to one-piece construction. For example, a device may comprise a plurality of pieces 12a as shown in FIG. 26C, that are formed into a plurality of hinge structures. As shown in FIG. 26C, a metastable octagonal dipole assembly, i.e. shown in the center of FIG. 26C, can be coupled with, e.g., seven exoskeletal segments, wherein each exoskeleton will direct self-assembly of a single miter joint. For the most part, assembly of the device would proceed as described below, that is, the exoskeleton would be opened in a cold metastable state, and then the exoskeleton would be placed over two or more magnetic segments. The construction of the invention is not limited to the configurations shown in FIGS. 26A-C, however, as a magnetic anastomosis device may have, e.g., eight magnets and only two exoskeletal pieces. Additionally, the exoskeletal pieces do not have to be identically shaped.

Furthermore the exoskeleton or exoskeletal structure is not limited to complete encapsulation around the magnet segments or a structure that traverses the entire magnetic assembly length. Rather, the exoskeleton includes any external structure that acts on the outer surface of the plurality of magnet segments, stabilizing them, keeping them aligned in plane, and ensuring the magnetic assembly assumes its predetermined deployment shape upon deployment. For example, intermittently attaching shape memory hinges around each of the magnet miter joints could achieve the desired exoskeleton effect. A "U-channel" or even less surface coverage could still achieve pre-forming, articulation, and resist non-planar bending. In some embodiments, the exoskeleton will pinch or grasp the magnetic segments. In some embodiments, the exoskeleton will be affixed to the magnetic segments, e.g., with glue or a wire or suture. In some embodiments, the exoskeletons will be affixed to the magnetic segments with a physical coupling, e.g. a screw or rivet.

Figure 27:
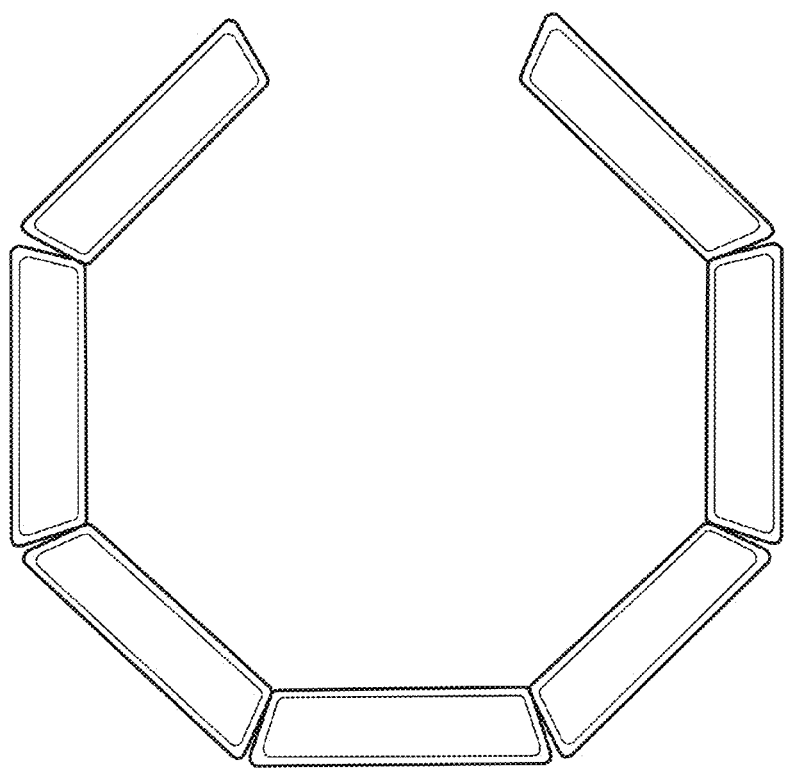
FIG. 27 shows a metastable assemblage of seven magnetic segments held by magnetic attraction at the mitered joints.

The stability of the mitered magnet configuration is further illustrated in FIG. 27. As shown in FIG. 27, a collection of only seven of the octagonal segments creates a metastable geometric structure because of the alternating N/S construction with the poles oriented normal to the face of the trapezoids (i.e., out of the plane of the figure). As shown in FIG. 27, the magnetic attraction between adjacent mitered joints is sufficient to keep the structure aligned and sufficient to overcome the repulsive forces of the two segments on either side of the opening. If one were to instead choose to keep the magnetization vector within the polygonal plane, i.e., rotated 90° and running parallel to the plane of the polygon, the magnetization could not be optimally orthogonal to all the segment ends in anything higher than a square. In other words, the structure would only be stable with poles aligned up/down and left/right on the figure. However, with the dipoles oriented N/S into and out of the page (normal to all the trapezoidal faces) not only are the device-to-device attractive forces optimized, but the balanced magnetic attraction between mitered segments stabilizes the magnet assembly. Additionally, the same segment-to-segment attraction provides the self-assembly forces that cause the device to properly curl into a polygon upon exiting the delivery device.

Figure 28:
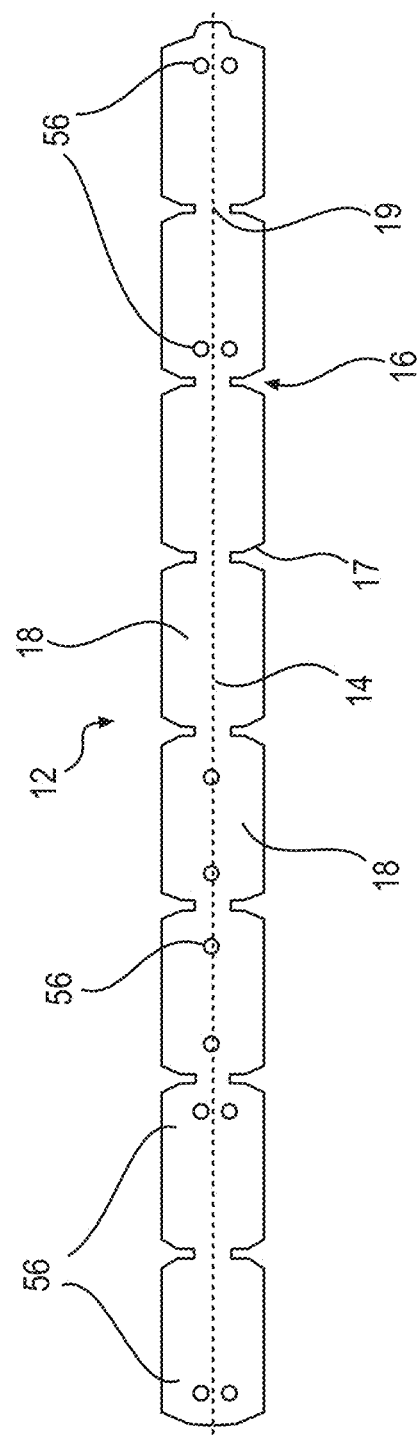
FIG. 28 shows an initial shape photoetched from 0.1 mm thick nitinol sheet.

Details of construction of the shape metal exoskeleton are shown in FIGS. 28 and 30-32. FIG. 28 shows a photoetch pattern for a thin walled tubular structure that will be modified to form the exoskeleton of an octagonal magnetic device, such as shown in FIG. 23. Using known photoetch techniques, the starting material, which may be any biocompatible shape metal such as Nitinol, is etched to provide the needed miter clearances 15 and notch radii 16 to allow the etched piece to be shaped into an exoskeleton, as described below. The photoetched material may also include holes 56 as needed to attach fiber loops to create attachment points 22, described above. Alternatively, nitinol sheets can be cut into strips and then photoetched or stamped to create a pattern similar to FIG. 28. Alternatively, stacks of NiTi sheets can be wire EDMed in an appropriate clamping fixture to produce a stack of exoskeleton blanks with the required initial external shape. Holes can be drilled in the resulting stack or in separate pieces by either EDM or laser, respectively.

Starting from the photoetched or otherwise machined pattern of FIG. 28, the exoskeleton is formed by a sequence of fixtured shape settings accomplished most commonly by holding the part in the desired shape and briefly heating to 900° F. (480° C.), most preferably in a bed of chromatographic silica fluidized by either air, argon or nitrogen and heated by immersed resistance elements. Alternatively, shape setting can be carried out in vacuo. The first step in the sequence is to shape an elongated 'square' channel (side flanges 90 degrees from backbone), the second to shape this linear square channel into a closed polygon, and the third is to pinch the sides of this polygonal square channel inward toward the central polygonal plane. The final shape looks similar to a small polygonal beveled picture frame (see FIG. 26A). If nitinol sheet is the starting material the angles of the flanges are folded to achieve an angle less than 90 degrees so that the exoskeleton, after being 'cold-opened,' as described below (see FIGS. 32A-33B), to angles of approximately 135 degrees and having the magnets placed, can, upon rewarming, properly pinch the magnetic assemblage. After machining and shape setting, the resulting exoskeleton 47 is sufficiently robust and has a natural tendency to curl up into a polygonal structure, 12 as shown in FIG. 26A.

Figure 29:
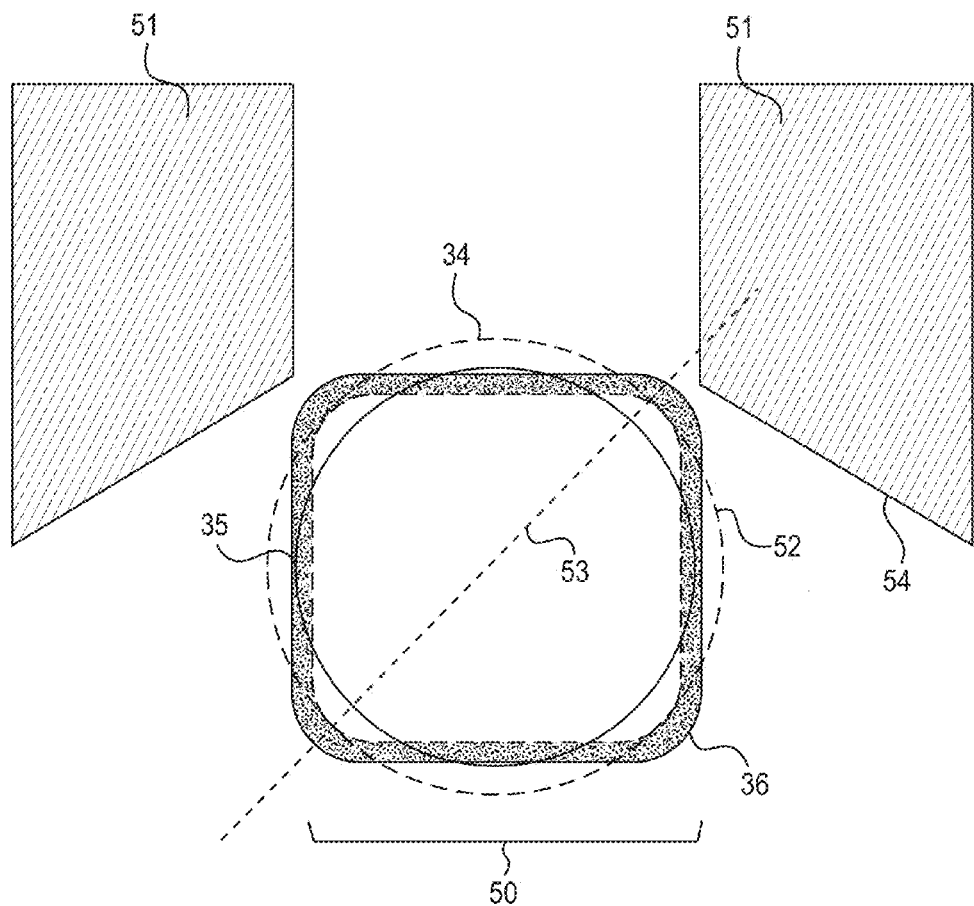
FIG. 29 shows the deformation of a patterned nitinol piece formed from a thin-walled circular tube. The newly shaped exoskeleton has a roughly square cross section.

FIG. 29 shows the deformation of a thin-walled nickel titanium round cylindrical tube 34 formed by a die 51 into a thin-walled square tube 35. The cylindrical diameter is chosen such that the total circumference of the cylinder's neutral axis 49 has the same length as the analogous neutral axis 50 in the required square tube. Sharper corner radii can be achieved by this method than when 'channel forming' sheet material given the much smaller bending strain when measured from an already small tube radius. Forming at elevated temperatures can also increase tolerable bending strain. In some embodiments, the bottom of the square tube can be removed, e.g., with EDM, to produce a square channel. One advantage of a square channel is that it is not necessary to "unpinch" the shape metal. A device of the invention can be formed by merely inserting the magnetic segments and then securing them to the exoskeleton with adhesive, e.g., cyanoacrylate glue.

In many instances, the channel of the exoskeleton will be shape set such that, at temperatures above its Austenite finish ($A_f$) temperature, the exoskeleton returns naturally to a pinched configuration with some amount of force (see FIG. 33A), which allows the exoskeleton to grab the magnetic segments, e.g., as detailed with respect to FIG. 23A.

Prior to placing the magnetic assemblage inside the exoskeleton, it is necessary to open up the pinched channel. The shape metal exoskeleton is cooled whereupon it becomes very soft and deformable, said deformation being perfectly recoverable upon warming. While the required temperatures will vary depending upon the particular alloy used, a sufficient temperature to work the material is typically around −30° C. Opening the exoskeleton is accomplished using the device shown in FIGS. 32A and 32B, described below, operated in a bath having a temperature typically less than about −30° C., e.g., less than −35° C., e.g., less than −40° C.

Figure 31B:
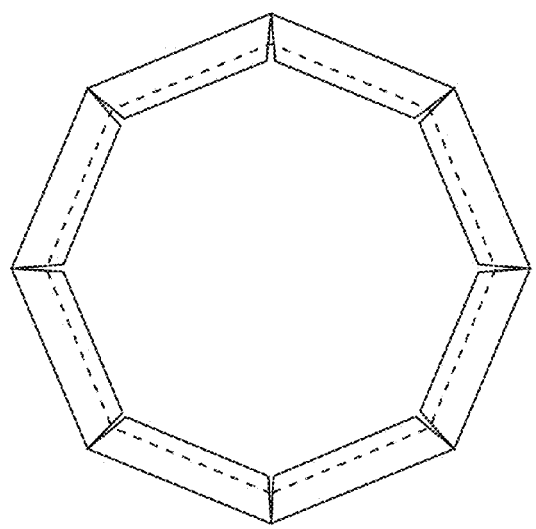

After the channel has been flared, the cold closed octagonal frame is removed from the bath, and four of the eight segments are swung open, two on either side of the gap, so as to form a "C" shaped structure shown to the left of 31A. This still cold C shape can then receive the magnetic assemblage within itself, most preferably with the magnetic assemblage on an octagonal mandrel that gives the assemblage more mechanical stability during manipulation. The two segments on either side of the gap, four in all, are then bent back into their initial closed octagonal shape while they are still cold and their sides are still open or flared and able to envelope the magnetic assemblage (right side of FIG. 31A). After placing the octagonal exoskeleton over the magnetic assemblage, the exoskeleton is allowed to rewarm. Upon warming the exoskeleton above the metal $A_f$ temperature, the channel returns to its pinched shape, thereby clamping the magnets, and resulting in a complete magnetic anastomosis device, as shown in FIG. 31B.

Figure 32A:
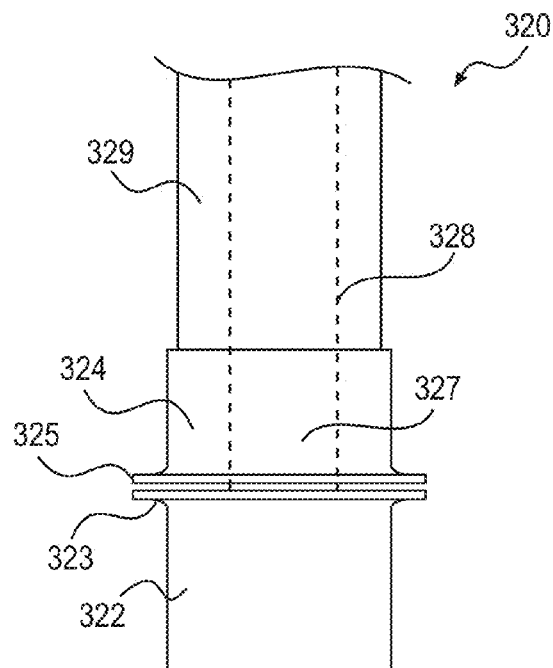
FIGS. 32A-B show an exemplary opening device for opening the shape metal exoskeleton to allow the exoskeleton to be placed over the magnet assembly.
Figure 32B:
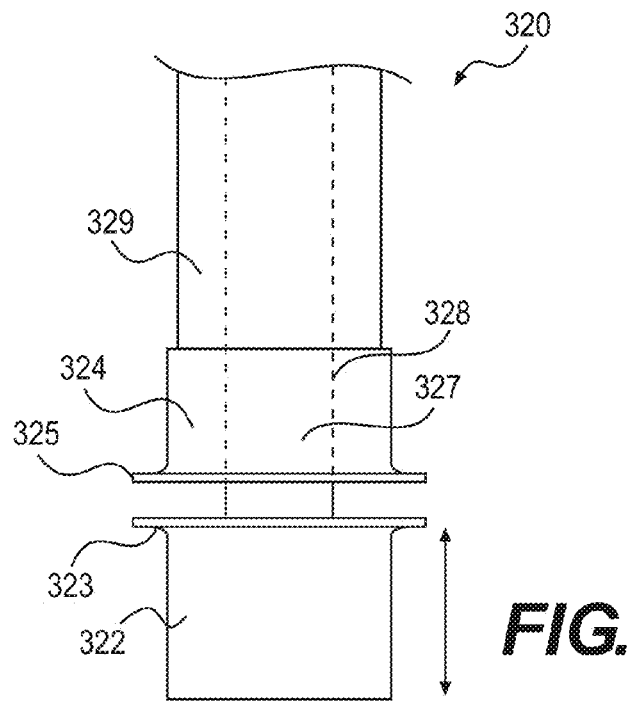
Figure 33A:
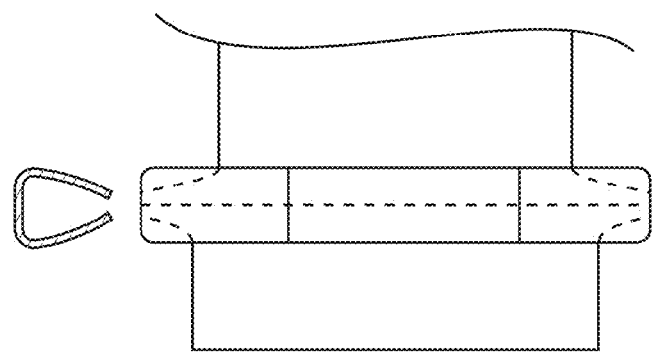
FIGS. 33A-B show the process of opening a formed shape metal exoskeleton prior to placing it on a magnet assembly.

An opening tool 320 is shown in FIGS. 32A and 32B. The opening tool 320 comprises a distal segment 322 and a proximal segment 324. The distal segment 322 is attached to a shaft 327 that fits though a channel 328 inside the stem 329 connected to the proximal segment 324. Both the distal segment 322 and the proximal segment 324 comprise edges 323 and 325, respectively, that interface with the channel of the exoskeleton, allowing it to be opened. In practice, the exoskeleton in a pinched configuration is loaded onto the closed opening tool 320, as shown in FIG. 33A. A retaining mold (not shown) is placed over the exoskeleton on the opening tool to assure that the exoskeleton does not jump off the opening device during the opening process. The retaining mold has a tapered octagonal cavity such that downward force on the opening tool 320 pushes the exoskeleton against the edges 323 and 325 to increase the effectiveness of the opening procedure. Other methods of opening the channel of the exoskeleton can include, for example using hydraulic or pneumatic pressure in a bladder placed in the channel to open the edges of the exoskeleton to allow the exoskeleton to accept the magnetic segments.

Figure 33B:
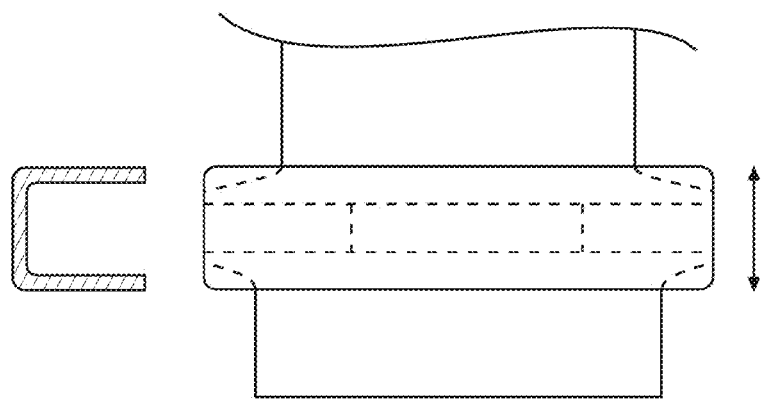

At the next step the opening tool 320, in the closed position with the exoskeleton attached and the retaining mold over the exoskeleton, is submerged in a bath of cold ethanol (−60° F.). While ethanol is the preferred solution, it is also possible to use other biocompatible fluids that will achieve the desired temperature, such as isopropanol. Once the exoskeleton is sufficiently cool (about 1 minute), the channel of the exoskeleton is opened with the opening device in the cold ethanol bath, to achieve an open channel, such as shown in FIG. 33B. The opening tool and exoskeleton are then removed from the bath, the open-channel exoskeleton removed from the opener, and then the open channel exoskeleton is returned to the cold ethanol bath until the magnet assemblage is ready for loading. While in the cold bath, the exoskeleton is in a metastable state and can even be removed from the bath for short periods of time before the shape metal will warm sufficiently to return to its natural pinched condition.

Prior to assembly, the magnetic assemblage is also placed in the cold bath to cool. The magnetic assemblage typically only requires a few minutes to cool sufficiently. Once the magnetic assemblage is cooled and ready for the exoskeleton, the magnetic assemblage and the exoskeleton are removed from the cold bath, and the exoskeleton placed on the magnetic assemblage. See FIGS. 31A and 32B. Care must be taken to place the gap in the correct position with respect to the north and south poles to achieve the desired "handedness" as discussed below. Furthermore, the assembly process must be completed in about 30 seconds, otherwise the exoskeleton will return to its pinched configuration. The completed magnetic anastomosis device is then allowed to warm to room temperature.

Once the completed magnet and exoskeleton assembly has warmed to room temperature, some amount of cyanoacrylate glue is applied to various points along the assembly (center of segments) and allowed to be wicked between the exoskeleton and the magnetic segments. In some embodiments, the additional glue is not necessary because the assembly is sufficiently robust. Once finished, the devices are sterilized and packaged in the elongated configuration (see FIG. 51) in sterile packaging for loading into a delivery device in the operating room.

Figure 30:
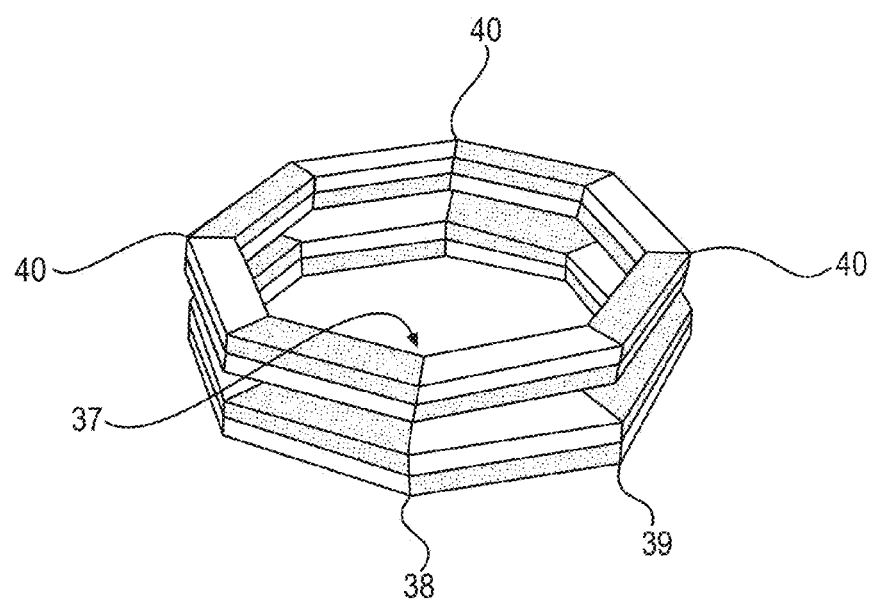
FIG. 30 shows two octagonal ring magnets interacting and demonstrates the various configurations of ring opening arrangement.

A detailed view of coupling octagonal magnetic devices is shown in FIG. 30. Essentially the two devices align so that the N face of each segment of the bottom device aligns with a S face of each segment of the top device. One concern with this arrangement is that it is possible that the gap 37 of the exoskeleton of the top device could align with the gap 38 of the exoskeleton of the bottom device, thereby allowing the coupled ring to open at the aligned gaps 37 and 38. This coincidence can be lessened by assuring that the exoskeletons and the magnet assemblies are constructed to give a "handedness" to each device, i.e., the gap 37 is to the left or right of the first N segment when view from above, and then assuring that one of each hand is deployed to create an anastomosis. This concept is explained above in greater detail with respect to FIG. 26B. By only coupling devices with different handedness, the gaps will never be coincident in a coupled device because that orientation (i.e., overlapping gaps) would be in full repulsion. Additionally, it is notable that a coupled device, i.e., as shown in FIG. 30, is remarkably non-magnetic when approached with another magnetic structure. Because all of the strong magnetic fields are coupled between the two devices, the lines of magnetic flux mostly wrap around and reenter the coupled device elsewhere. By this design, coupled octagons show almost no interaction with an external magnet. Of course, alternative device designs can be used to allow magnetic coupling to coupled devices, e.g., to a shunt.

Figure 34:
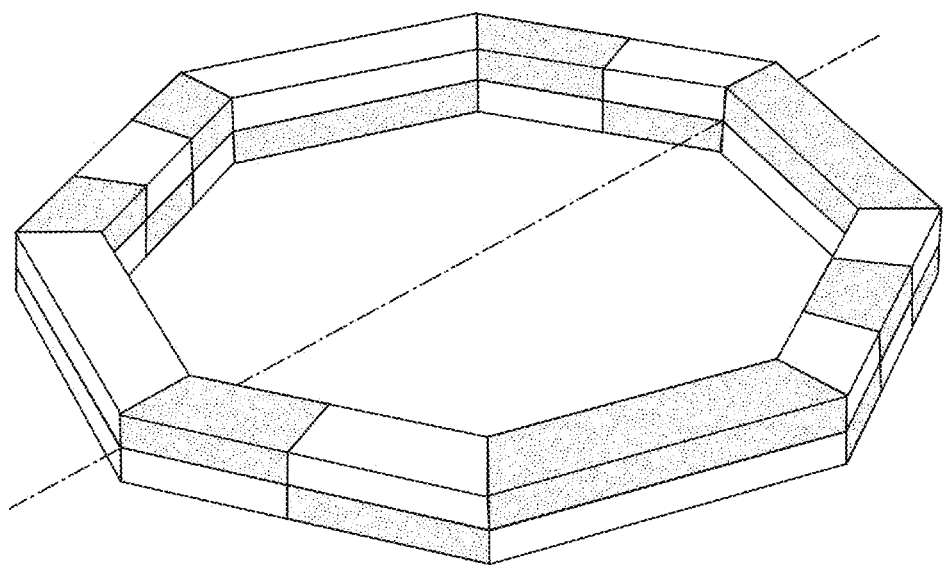
FIG. 34 shows an octagonal ring magnet with dipole, quadrupole and hexapole segments.

While a simple device can be constructed from a collection of identically-shaped magnets, it is also possible to construct self-assembling anastomosis devices containing unequal numbers of miters or miters of different sizes and configurations. For example, FIG. 34 shows a complex octagonal multipolar ring magnet comprising dipoles, quadrupoles and hexapoles with attractive forces at all miters. In this design each miter is still magnetically attracted to the adjacent segment helping the device to self-assemble. However because of the asymmetries in the design, from a distance the deployed ring has a wider magnetic signature and a tendency to align in only one configuration. In other embodiments, the structure can be a square with 2 dipoles and 2 quadrupoles, i.e. as shown in FIG. 35.

Figure 35:
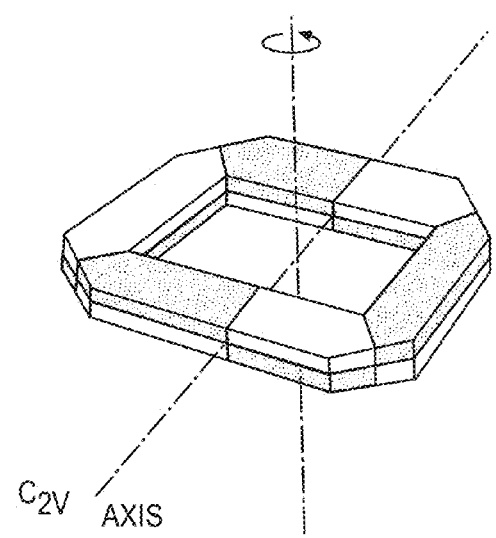
FIG. 35 shows a square of dipoles and quadrupoles.
Figure 36:
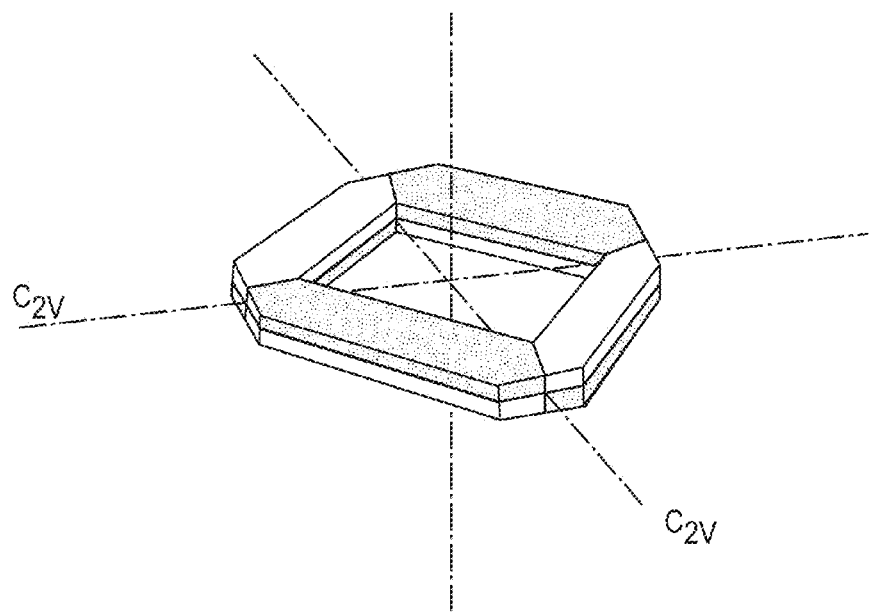
FIG. 36 shows a square of alternating dipoles.
Figure 44:
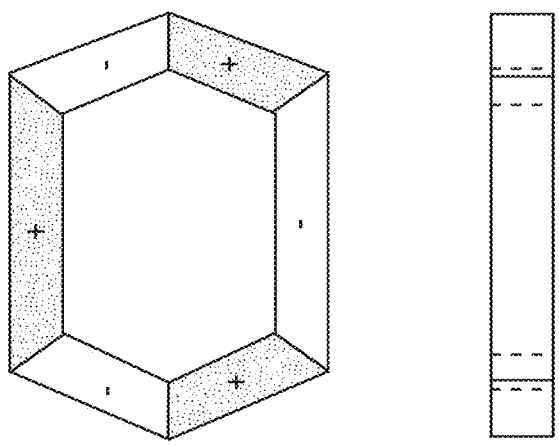
FIG. 44 shows a magnetically regular, physically irregular hexagonal ring magnet.

In the device of FIG. 35, the magnetic potential will drive azimuthal alignment of two matched rings into a unique and reliable orientation. In this configuration, the first 90 degrees of rotation takes a pair of devices from full attraction to zero. The second 90 degrees takes the pair from zero to full repulsion, and the third 90 degrees rotation takes it back through a zero. Thus, the configuration of FIG. 35 allows a user to confidently choose between assured coincidence of ring opening (if desired) and assured lack of coincidence (typically desired). This is a notable advantage over square design having identical dipoles, as shown in FIG. 36. The design of FIG. 35 is beneficial if one device is easily visualized and oriented, e.g. because it is against the stomach wall, while the matching device is difficult to orient because it is in an inaccessible location, e.g., the bile duct. The confidence in orientation of the square design of FIG. 34 is not available in all polygonal structures, however. For example, the orientation is not available to regular hexagons because each dipole-quadrupole pair reverses polarity and there must be an even number of such dipole-quadrupole pairs for the ring to attract itself closed, i.e., in order for the ends to have opposite polarity across the opening. Nonetheless, the square design of FIG. 35, with small changes in miter angles and segment length, can clearly morph into an irregular hexagon with alternating simple dipole segments such as, for example, shown in FIG. 44.

As is clear from the previous example, irregular geometry and segment size can contribute greatly to azimuthal control. Nonetheless, elongated segments can make it difficult to deploy the device through a curved channel (e.g., the contours of an endoscope), and the elongated segments can complicate self-assembly at the deployment site.

Figure 37:
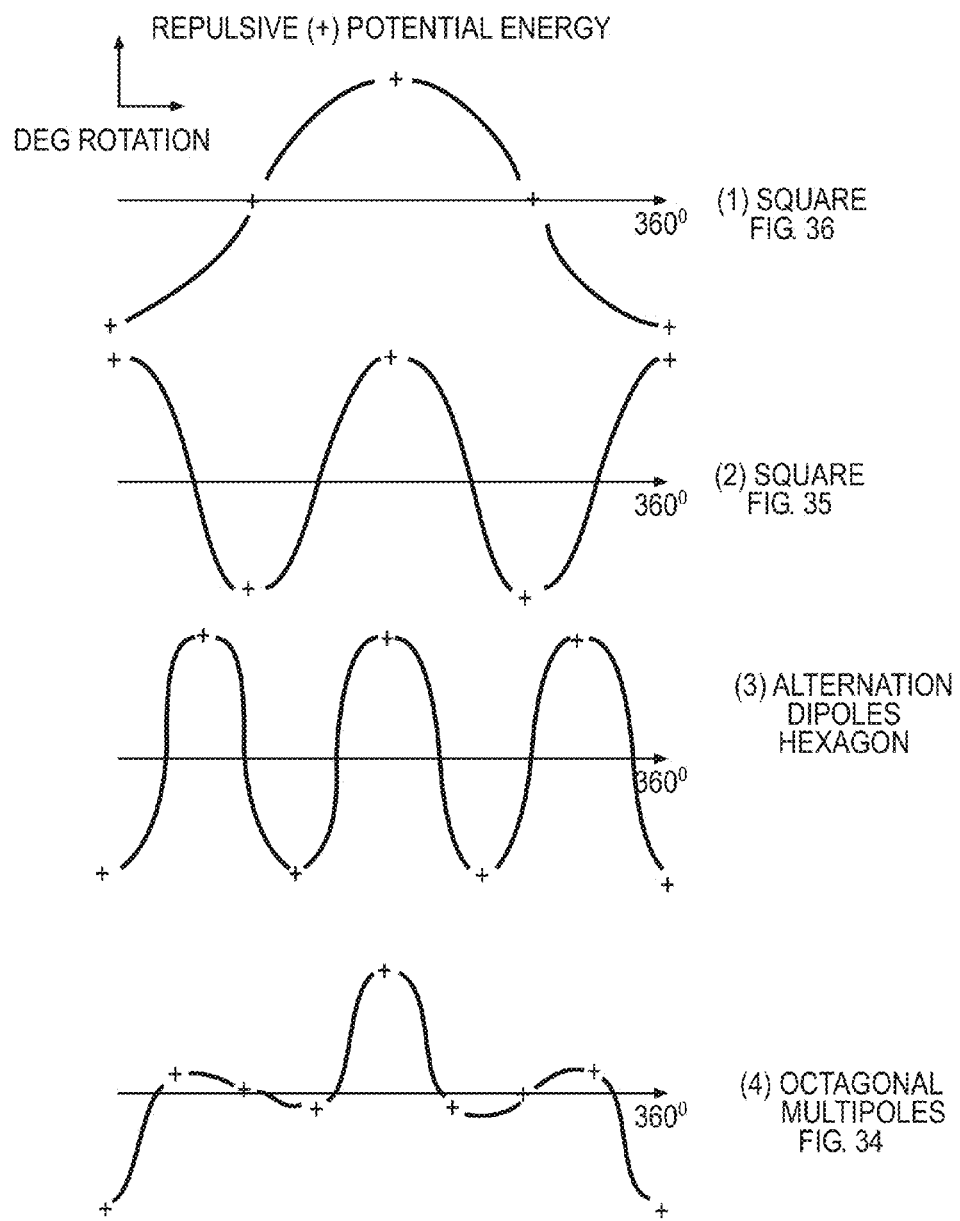
FIG. 37 shows potential energy plots for the juxtaposition of various magnetic polygons.
Figure 46:
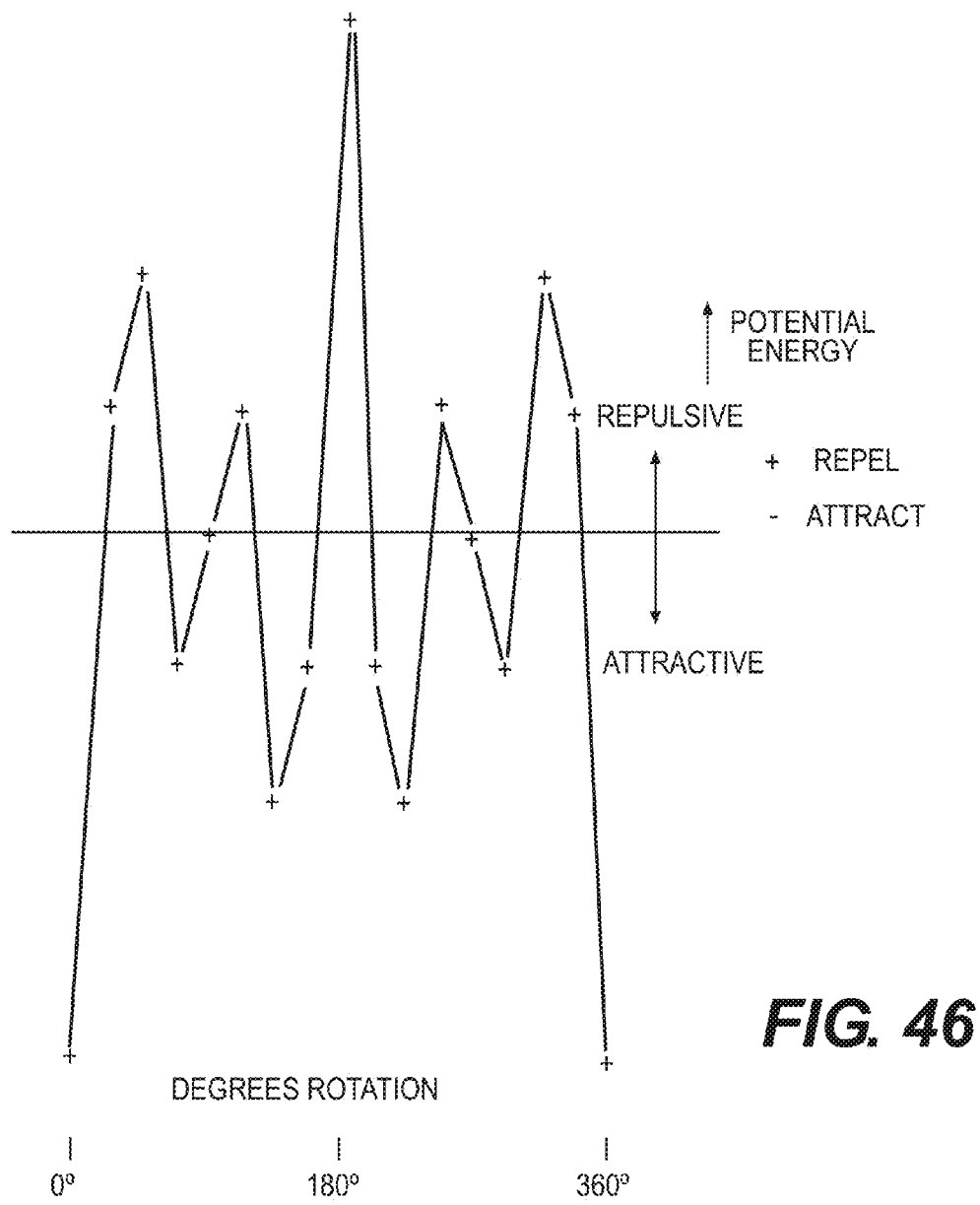
FIG. 46 shows potential energy variations as a function of rotational orientation of two octagonal ring magnets in FIG. 45.

By using potential energy diagrams, it is easy to identify the orientations available with a device of the invention. For example, FIG. 37 and FIG. 46 show magnetic potential energy curves of two mating polygons as a function of their relative azimuthal angle of rotation. FIG. 37 (1) shows that the square design of FIG. 35 couples in only one orientation at 0 degrees. FIG. 37 (2) shows that the square design of FIG. 36 is equally comfortable at both 0 and 180 degrees, thus it is equally likely that the two devices will be aligned or anti-aligned. Similarly, FIG. 37 (3) shows the potential energy profile of a regular hexagon only comprising dipole segments. In the instance of (3), it is actually more likely than not that the two devices will not be correctly aligned if the two devices are merely placed in proximity.

Figure 45:
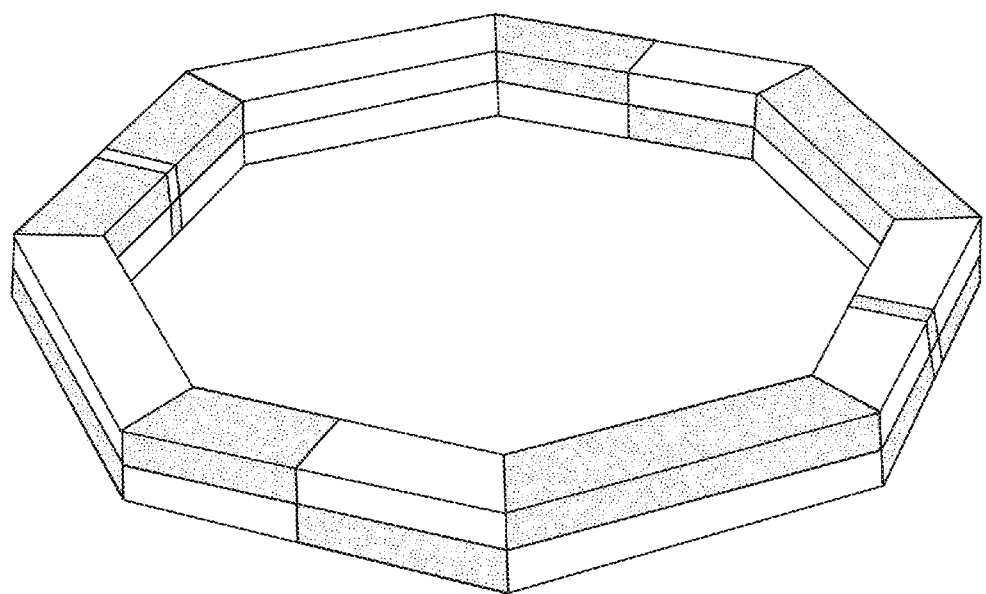
FIG. 45 shows a complex octagonal ring magnet comprising dipoles, quadrupoles and hexapoles.

Nonetheless, it is not difficult to use the methods of construction to produce more elaborate structures, such as the structure corresponding to FIG. 37 (4), i.e., the structure of FIG. 34 having dipole, quadrupole, and hexapole segments. Like the structure of FIG. 37 (1), the structure corresponding to FIG. 37 (4) can only be coupled in one configuration. More irregular shapes will give rise to highly erratic energy states, such as shown in FIG. 46, corresponding to the octagon structure of FIG. 45, having very short transitions in the hexapole segment. Regarding the octagonal embodiment of FIG. 34, it is clear that higher order polygon devices can be constructed having only a single orientation of interlock with a mating device. Such arrangements assure that the gaps of the two devices are not aligned in the final assembly, and additionally allow orientation of peripheral devices, such as shunts. As shown in FIG. 37 (4), the eight different states this system can occupy include states with intermediate energy levels which represent energy wells between which the system could move. However, with small amounts of manipulation, the paired devices will tend to fall into the lowest given potential energy configuration.

Figure 38:
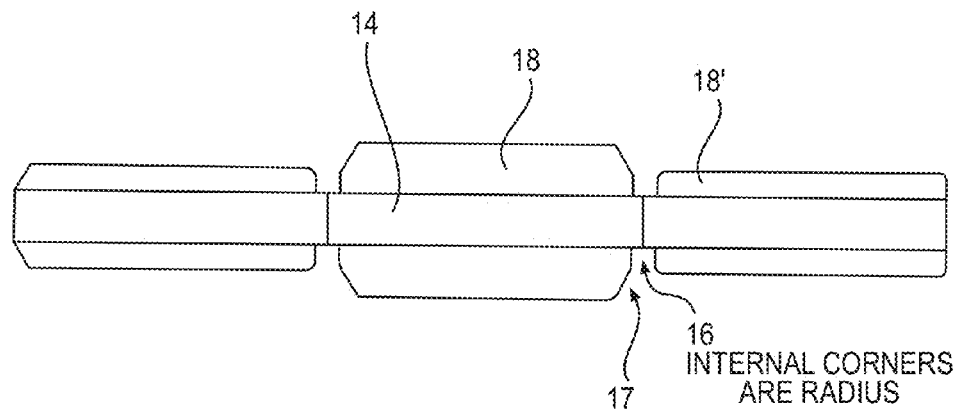
FIG. 38 shows the photoetch pattern for a segmented exoskeleton.
Figure 39:
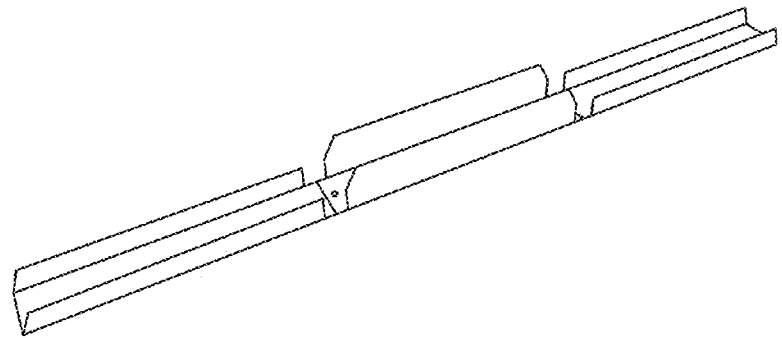
FIG. 39 shows FIG. 38 shape set into a channel by heating the material in an inert atmosphere and then quenching.

In some embodiments, it may be beneficial to use a multi-piece exoskeleton to fabricate a magnetic anastomosis device. When preparing larger anastomoses requiring larger structures, it may be easier to deliver two or three separate pieces per polygon because the entire polygon cannot be negotiated through the delivery device in an uncurled state, similar to FIG. 24. FIG. 38 shows a photoetch pattern for a 0.004" nitinol sheet that is shape-set for use as a portion of the external exoskeletal structure for the magnetic ring of FIG. 41. In the design of FIG. 38, short flanges 18' are half as wide as regular flanges 18, allowing two exoskeletal structures to share a single magnetic segment when assembled. FIG. 39 shows FIG. 38 after channel shape setting the patterned nitinol sheet for several minutes at 900° F. (480° C.). In alternative embodiments, the patterned nitinol may be formed with laser cutting or stamping.

Figure 40:
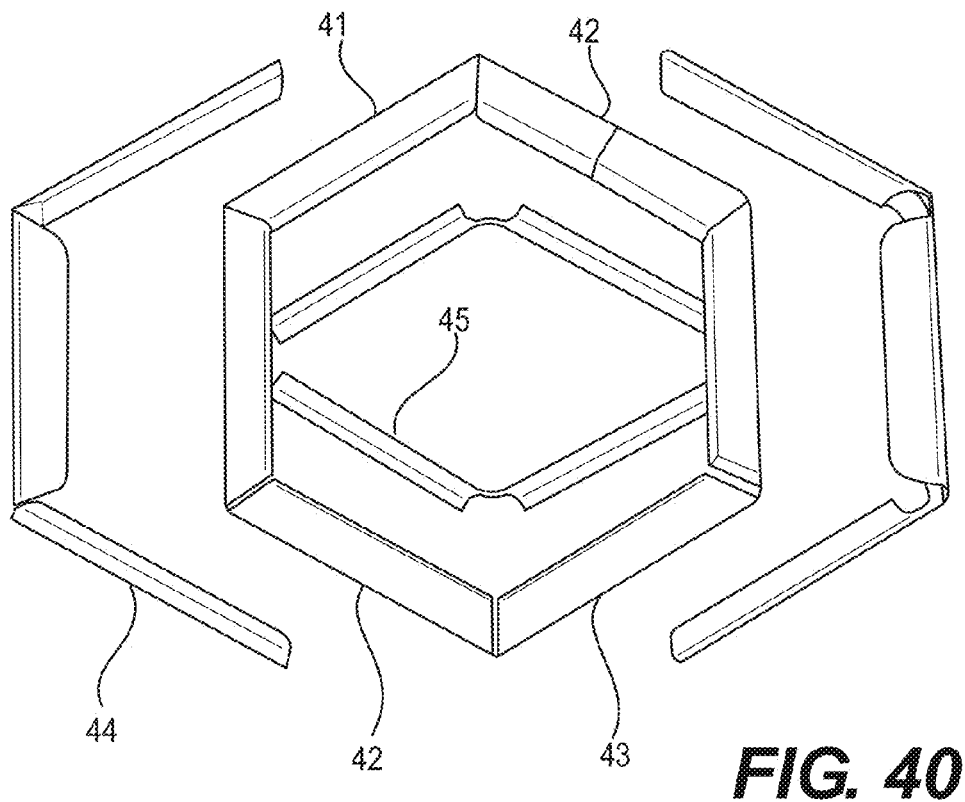
FIG. 40 shows two external NiTi exoskeletal and two internal NiTi exoskeletal structures before adhesive assembly to magnet segments.
Figure 41:
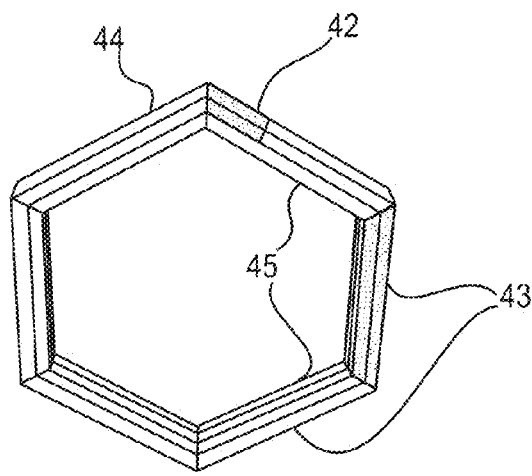
FIG. 41 shows exoskeletal structures with various magnetic polarities in the six polygonal multipolar segments.

FIG. 40 shows a magnet assembly 44, comprising two symmetric quadrupolar sides 42 and four dipolar segments 43 ready for adhesive assembly with two external 44 and two internal 45 exoskeletal structures. Alternative designs may use asymmetric exoskeleton components to assure that a device self-assembles in a particular way or with one portion folding before the other portion. See, e.g., FIG. 26C. FIG. 41 shows a variety of external and internal exoskeletal structures depicting magnetization through the trapezoidal faces of each segment, normal to the polygonal plane.

Figure 42:
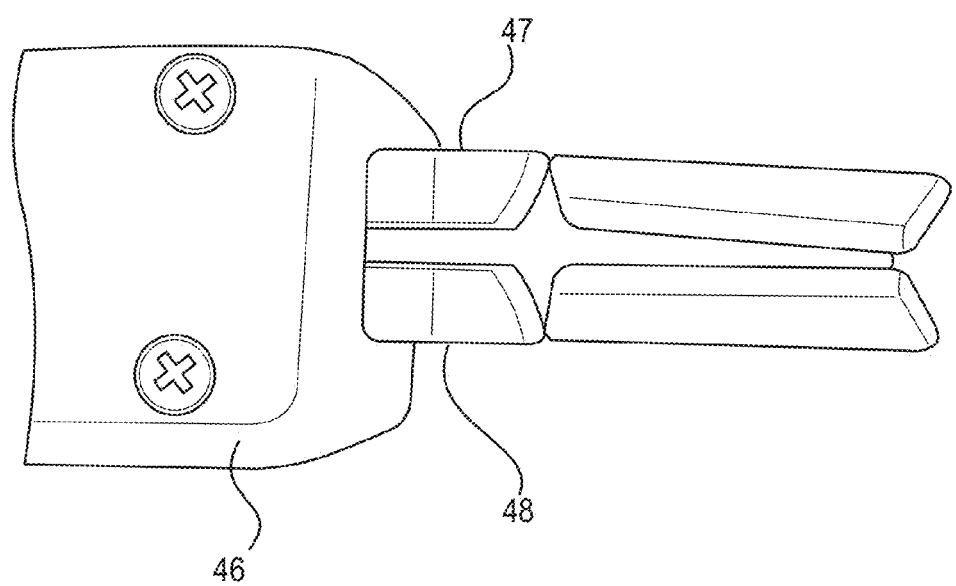
FIG. 42 shows an assembly as in FIG. 39 emerging from a rectangular channel.
Figure 43:
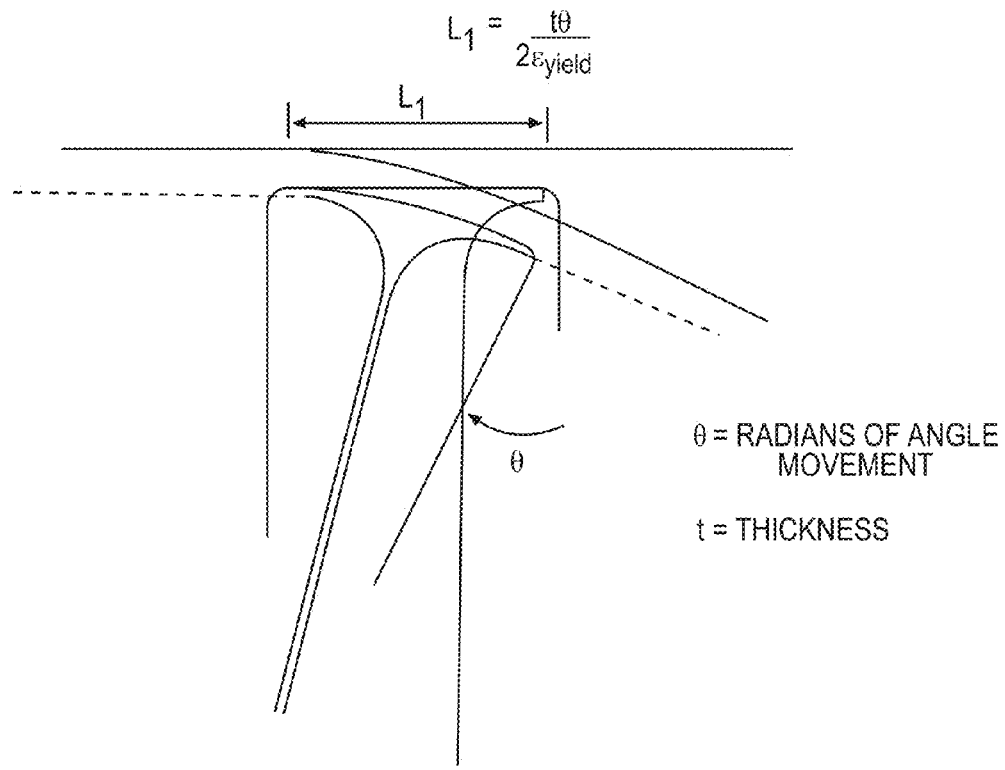
FIG. 43 depicts the geometry of the peripheral metallic ring of the exoskeleton at one miter joint between magnetic segments in both delivery and deployed configuration.

In some embodiments, a self-assembling device can have a living hinge that allows the device to be deployed in a folded arrangement, e.g., as shown in FIG. 42. FIG. 42 shows the extrusion of the hexagonal structure of FIG. 41 from a rigid rectangular channel 46. Though segments 47 and 48 repel each other in the channel, there is a strong magnetic force on segment 47 to move upward, out of the paper, and on segment 48 to move downward into the paper and attract at their bottom and top surfaces respectively. As shown in FIG. 43, it is possible to roughly calculate the distortions that result in the exoskeletal structure in the regions between polygonal segments during deployment, i.e., during the change from stowed to deployed configuration. The formulas for calculating strain as a function of angular excursion, material thickness and intersegmental "free length," ($L_1$) are well known. Based upon these calculations, it can be determined ahead of time whether a particular configuration of self-assembling magnetic device is likely to survive deployment from an endoscope, for example.

Figure 47:
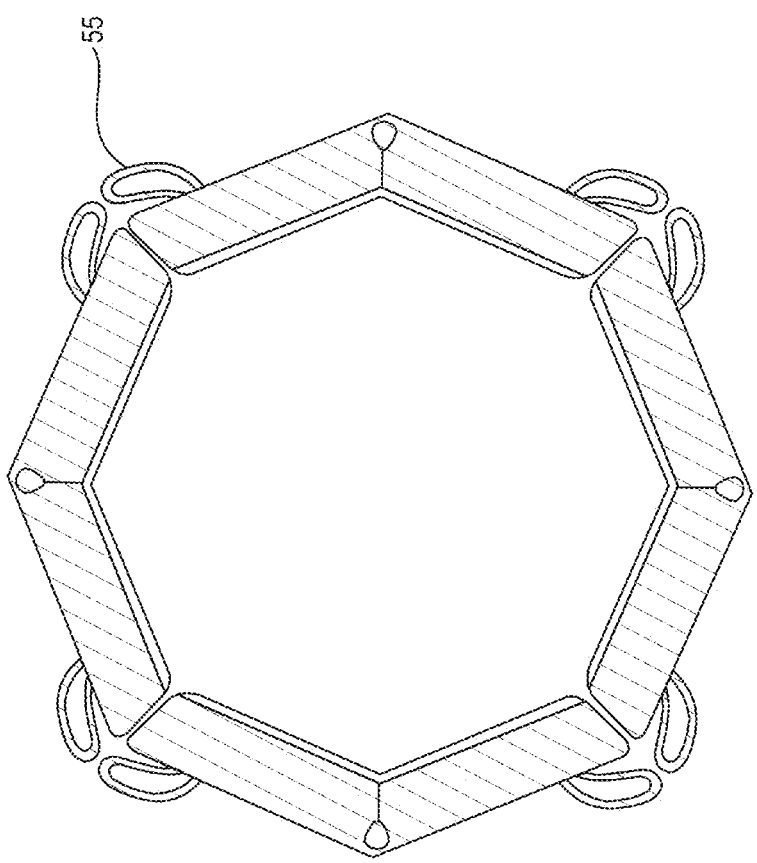
FIG. 47 shows an octagonal device constructed from four shorter pieces comprising only two linked magnetic segments each. Integral loop structures reinforce the exoskeleton and provide means for manipulation the device during deployment.
Figure 48:
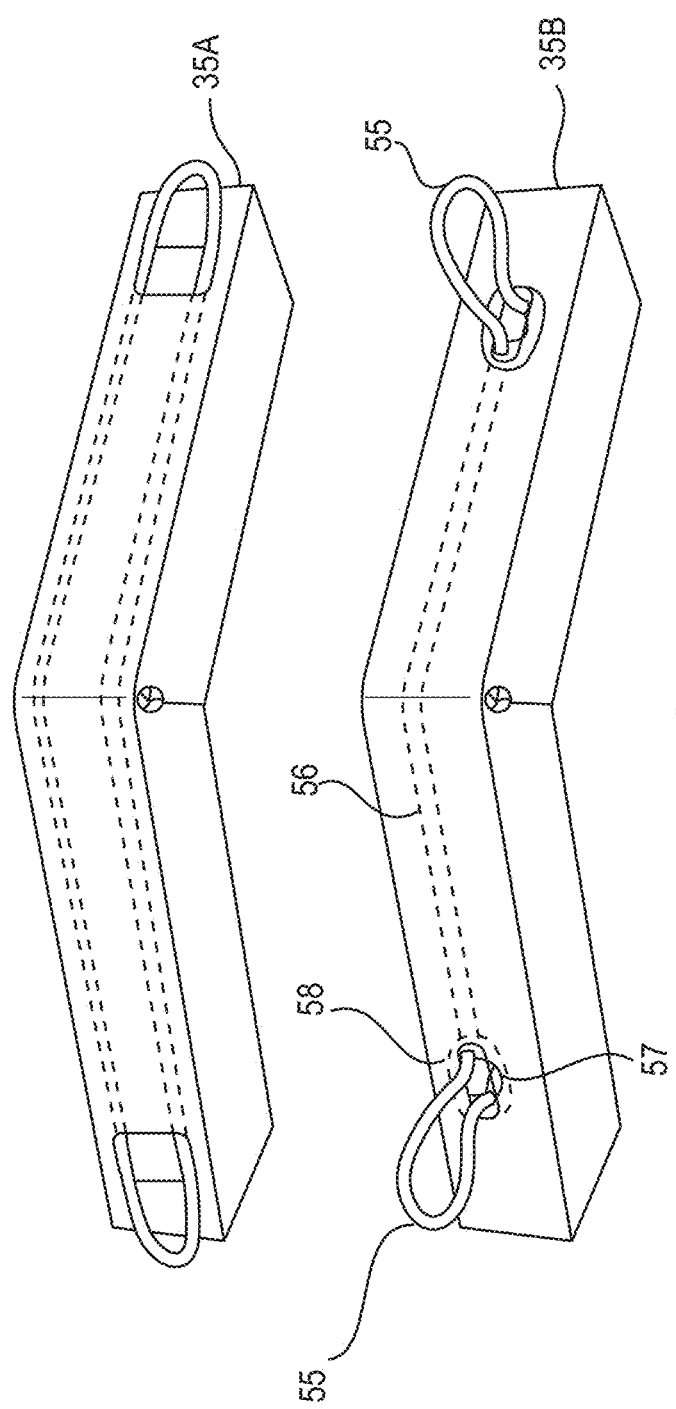
FIG. 48 depicts two embodiments showing use of nitinol wire or braided Dyneema™ or polyester to provide tensile reinforcement and means of manipulation.

As shown in FIG. 47, an octagonal device can be constructed by sequentially deploying four separate pieces, each consisting of two linked segments, mutually attracted to each other. As shown in FIG. 47, each segment has at least one attachment point (loop) of high-tenacity material for manipulation. These loops can be simple suture loops emerging through holes in the exoskeletal structure, e.g., as described above with respect to FIGS. 23 and 28. Alternatively, the loops can be external manifestations of high tenacity strands running between magnetic segments and providing tensile reinforcement to the exoskeletal structure against tearing at the intersegmental regions 19, as shown in FIG. 48. In embodiments having the tensile reinforcement, a cross section of the exoskeleton may have regular guide loops (elements 20 and 21 of FIGS. 23A and 23B) to maintain the tensile members in place. The reinforcing elements can be solid, stranded, twisted or braided and can be comprise stainless steel, titanium, aramid fibers, oriented polyesters of various chemistries, gel-spun UHMW polyethylene (Dyneema™, Spectra™) or superelastic (37C) nickel titanium wires. Loops therein can be created with knots, braid splicing, brazing, welding, or adhesive bonding. In some embodiments, the attachment points (e.g., loops 55) emerging through holes 56 photoetched through the patterned shape metal 14 prior to shape setting. See the discussion with respect to FIG. 28. The attachment points can be engaged by retaining means such as sutures or staples, as needed during the procedure. The attachment points can also be manipulated, e.g., with forceps or a robotic grabber during deployment.

As a further exemplary embodiment, FIG. 48 shows an isometric view of two different "two-segment" designs. Depending upon the miter, a collection of such two-segment designs can form a regular hexagon or a regular octagon. The top embodiment of FIG. 48 depicts a version comprising a loop of nickel titanium wire, between 0.003" and 0.010" diameter, preferably 0.004-0.006" diameter. The loop emerges through openings in the back of the exoskeleton and runs in grooves, 20, in the outer surface of the magnetic segments to the other end loop or other fixation means, thereby providing additional strength and integrity to the exoskeletal structure. The bottom embodiment of FIG. 48 shows an alternative construction comprising two attachment points 55 (i.e., suture loops) on the ends of a suture length 56 that runs along the spine of the two-segment piece. In the bottom embodiment of FIG. 48, two knots 57 are trapped within a depression in the magnetic segment 58, allowing the exoskeleton to sit flush against the magnetic segment 58. In either of these embodiments adhesive can be wicked into these holes, and/or other holes elsewhere in the exoskeleton, to achieve magnet segment immobilization.

In alternative embodiments, the magnetic segments can be connected with a resilient hinged material. For example, a central exoskeletal band can be achieved with either pseudoelastic materials or fiber reinforced composite structures or a combination of both. In some embodiments the hinges can be formed from Dyneema®, Spectra®, Vectran®, Kevlar® or similar materials. These fibers have especially high-tensile moduli, and can be fabricated to provide the tensile integrity and out-of-polygonal-plane stiffness similar to the parallel flat exoskeletal members, described above. In an embodiment, multiple tensile fibers are bonded to the backbone and sides of the magnetic segments, thereby maximizing the out-of-polygonal-plane stiffness and reinforcing the miter joint. In other embodiments, the magnetic devices can comprise a combination of shape metals and tensile fibers. In some embodiments, the structure could include a nitinol exoskeleton and nitinol wire reinforcement, e.g., 0.002"-0.010", preferably 0.004-0.006", diameter. As discussed previously, the nitinol wire can also be used to create attachment points along the structure.

In some embodiments, the exoskeletal structures are coated with a biocompatible coating. This coating could be applied in a variety of ways, including plating, vapor deposition, dipping, or spraying. In an embodiment, the coating is polytetrafluoroethylene (PTFE), a.k.a. Teflon. In some embodiments, the exoskeletal structures are gold, silver, or platinum plated. In some embodiments the exoskeleton is coated prior to assembly with the magnetic segments. In other embodiments, the exoskeleton is coated after the exoskeleton has been mated with the magnetic assemblage. It is also possible to coat the structures with a drug-eluting coating, such as Parylene™, that can be used to deliver drugs in a localized and controlled fashion. Drugs suitable for elusion include anti-angiogenic and anti-clotting coatings that discourage the attachment of tissues to the magnetic devices.

Figure 49:
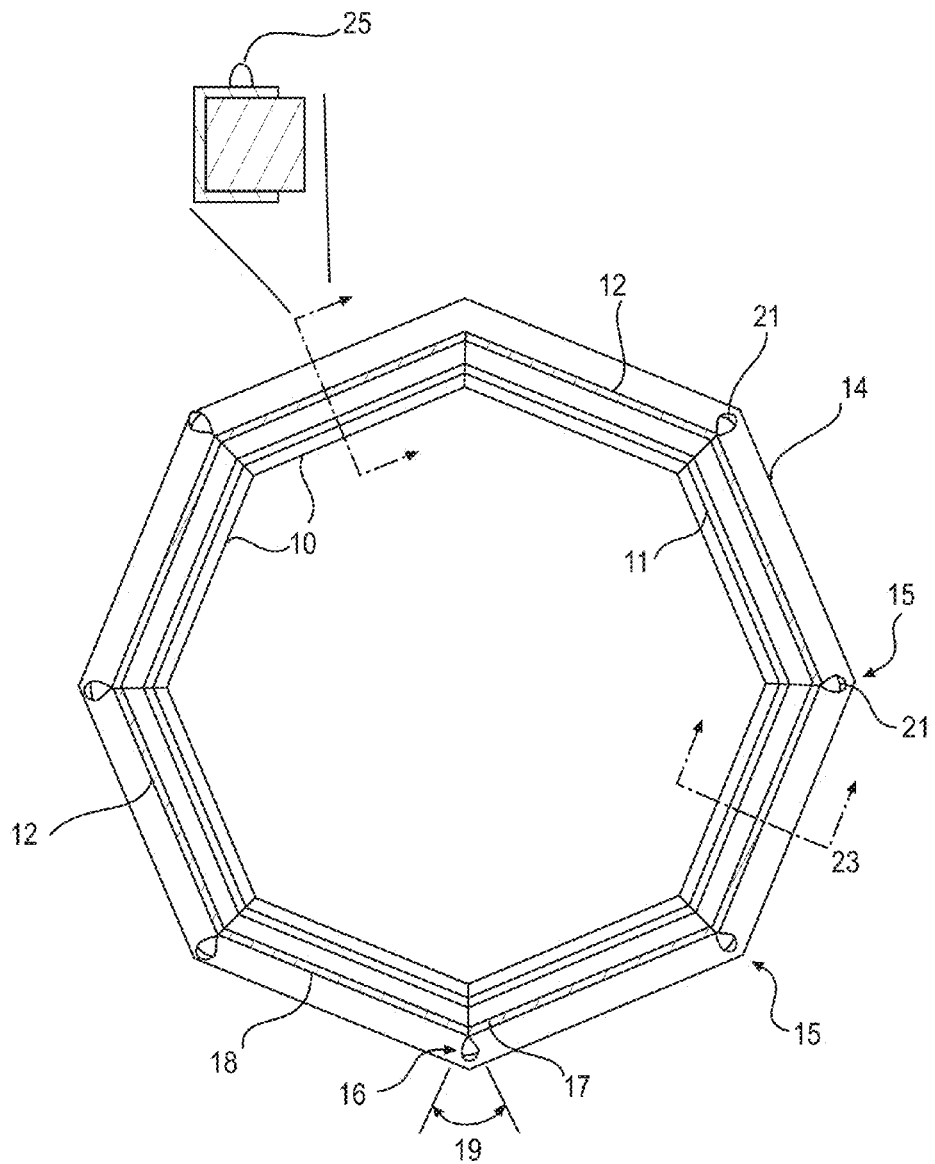
FIG. 49 shows a raised feature or protruding element (25) that can be incorporated to increase pressure on a tissue by reducing the contact area against the tissue.

A device of the invention may also include features or protrusions, as necessary. Such elements can be incorporated into the structures to increase pressure at certain contact points by reducing contact area. In some instances, protrusions will assist in placement and retention of a coupled device. Other features may include a raised channel or radius formed into the exoskeletal frame prior to assembly. In some embodiments, a raised feature on one magnetic device is matched with a channel on the mating magnetic device. A magnetic anastomosis device having a raised feature is shown in FIG. 49.

Figure 50A:
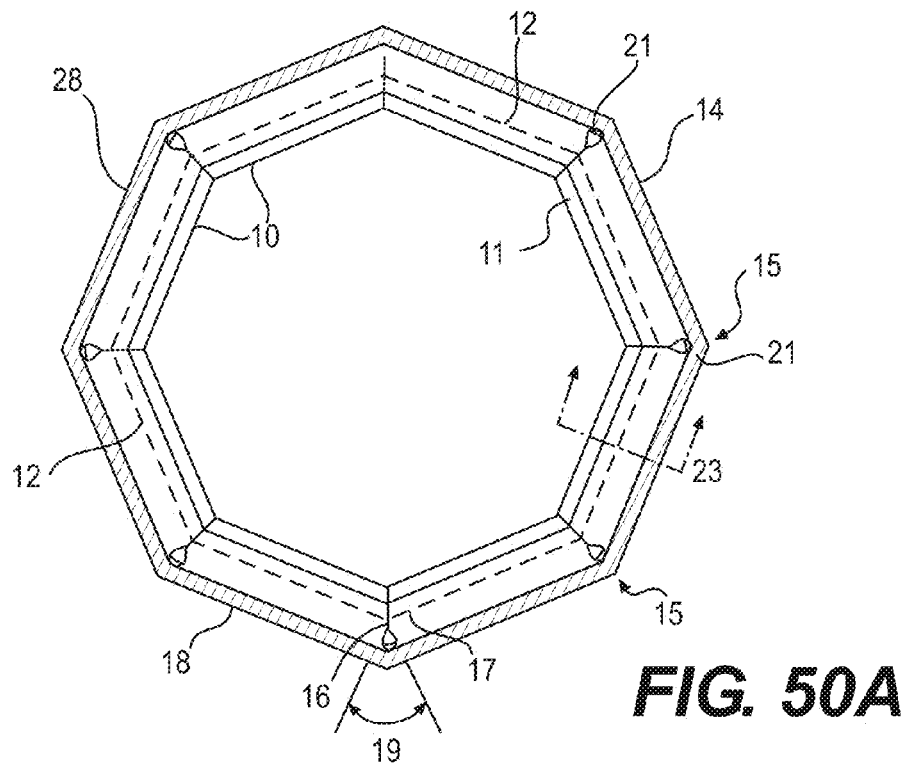
FIG. 50A shows an embodiment, where the exoskeletal structure on the preferred side of passage is slightly larger in size than its mating exoskeletal structure. Additional material (28) has been added to establish this as the preferred side of passage as the devices disengage from the tissue.
Figure 50B:
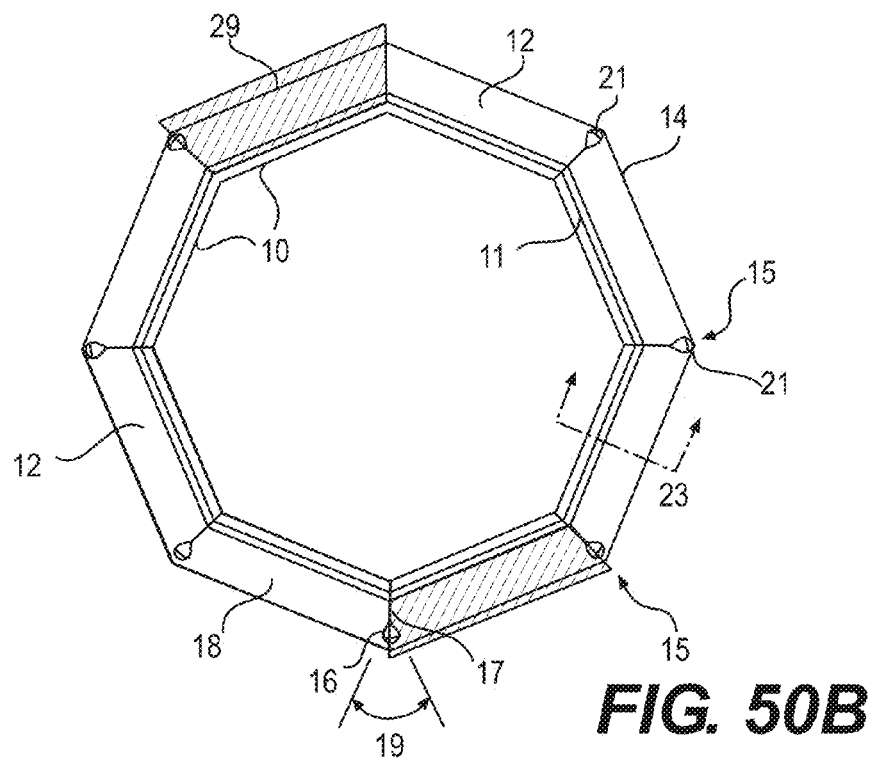
FIG. 50B illustrates that additional magnetic material (29) can be added to determine the direction in which the coupled assembly disengages from the tissue.

In addition to features that assist with placement and retention of the structures, other features can be added to assist with detachment and passage of coupled devices. As discussed above, when an anastomosis has sufficiently formed, and the surrounding tissue has necrosed, the coupling of magnetic devices will fall away from the tissue and pass naturally through the body. Preferably the used structures will pass posteriorly, in the direction of normal peristaltic motion, thus ensuring proper passage. In other embodiments, it is desirable to direct the coupled devices move toward a larger lumen (e.g., the small intestine) as the coupled devices disengage the tissue. Various design features can be added to ensure the direction of exoskeletal structure passage. For example, FIGS. 50A and 50B show a preferred embodiment, where the device on the preferred side of passage is slightly larger in size than the mating device. This additional material (indicated by the dotted lines) provides enough resistance that the devices will pass into this preferred lumen, and not pass through to the unintended lumen. Additionally, by introducing additional material attached to magnets, the same effect can be achieved, in situations where no additional size or lumen delivery space is available.

In another embodiment, portions of the exoskeleton can modified to facilitate planned or emergency disassembly of the device. For example, biodegradable components can be incorporated into the exoskeleton to assist in self-removal after anastomosis formation. PLA, PLGA, or PVA, or copolymers comprising these polymers, can be included to encourage the structure to break down over time and pass naturally in small, atraumatic segments. In other embodiments, the exoskeleton will be fabricated with a "ripcord" or other structure that can be cut or detached with an endoscopic or laparoscopic instrument, thereby causing the assembled device to fall into several pieces that can be passed harmlessly through the body.

Figure 51A:
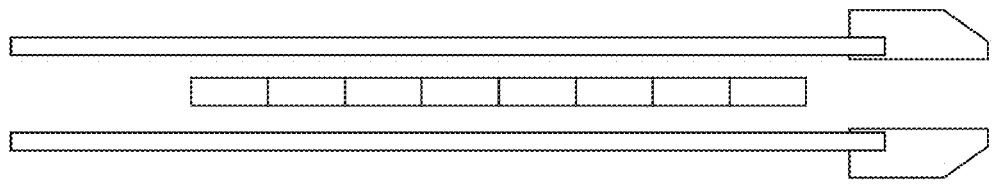
FIG. 51A shows the containment tube packaging with pre-loaded exoskeletal structure to facilitate easy channel insertion.
Figure 51B:
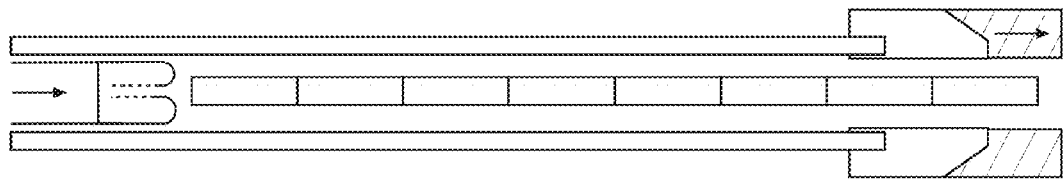
FIG. 51B shows a deployment rod pushing the exoskeletal structure into an endoscope port.

Packaging and introducer tools are also important in facilitating easy and effective placement of self-assembling magnetic devices. Without proper packaging and introduction into the delivery device, the magnetic device may become damaged and take on an unintended configuration upon deployment. Prior to loading into a delivery device, the exoskeletal structure is packaged in a sterile containment tube, which prevents the exoskeletal structure from opening and self-assembling. This containment tube also facilitates easy introduction into the endoscope or catheter delivery system with external dimensions compatible with the proximal port to which it is being introduced. FIG. 51A shows a containment tube with an exoskeletal structure pre-loaded. FIG. 51B shows the exoskeletal structure being pushed into the channel using a deployment rod. The details of the deployment rod are shown in FIG. 52.

In one embodiment, octagon magnetic devices are stored and shipped in an approximately 6 inch polyethylene tube with caps on each end. The insertion end (the end that is eventually loaded into the scope channel or proximal scope connector) has a cap that is removed immediately prior to insertion into the scope. The end of the tube may be tapered as shown in FIG. 51A. The proximal end of the insertion tube has a cap with a hole drilled in it to accommodate a Teflon rod. The rod may be shaped as shown in FIG. 52. When loading the octagon, the Teflon rod is advanced into the insertion tube, thereby pushing the octagon outside of the tube and into the endoscope, as shown in FIG. 51B. The insertion tube and advancement rod allows for a convenient and sterile method for octagon insertion into the endoscope.

In some embodiments, the magnetic devices are stored and shipped in a final assembled state, i.e., as completed polygons. Because this configuration is lower energy, it provides a longer shelf life, e.g., because the exoskeleton are not be strained over long periods of time. This strain could also weaken adhesive (if used). The lower energy configuration will also be more robust during shipping, especially when the devices may be accidentally exposed to cold temperatures, such as in the cargo hold of a plane. If an extended device having a shape metal exoskeleton were exposed to sufficient cold, the shape metal could become pliable enough that the magnetic segments will come loose or move toward one another and cause imperfections in the exoskeleton.

In some embodiments, multiple exoskeletal structures can be loaded into the endoscope or delivery device. Loading multiple structures can potentially simplify and shorten the procedure due to reduced exchanges, complexities, and intubations. For example, as discussed with respect to FIG. 4B, a first device can be placed endoscopically within the GI tract, and then the second device can be placed at a different location within the GI tract using the same endoscope. Additionally, paired magnetic devices can be loaded into a single tube such that a matched set, or set having the desired handedness are deployed.

Figure 52A:
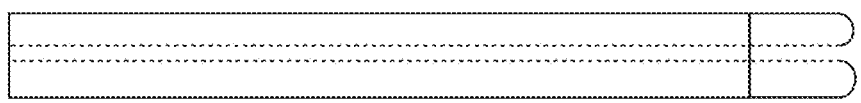
FIG. 52A shows a deployment rod with an internal channel through which the exoskeletal structure sutures can be passed.

In some embodiments, a deployment tool is required to push a magnetic device out from the deployment lumen, e.g., an endoscope channel. One embodiment of a deployment tool is shown in FIG. 52A. The deployment rod should be incompressible so as to provide adequate pushability against a device within a delivery lumen, e.g., and endoscope delivery channel. It should also be flexible and lubricious, so that the deployment tool is easily advanced through the endoscope channel after the endoscope has been moved to the site of the anastomosis. The deployment tool preferably has a rigid distal tip, either magnetic or non-magnetic. In some embodiments, the deployment tool comprises a magnetic (preferably neodymium) tip that helps to deploy a magnetic anastomosis device and helps to guide the distal end of the device to avoid pinching tissue (see FIG. 52B). Furthermore a magnetic tip allows the deployed magnetic device to be easily manipulated with the deployment tool. In other embodiments, a non-magnetic distal tip (stainless steel or similar) allows the deployment rod to manipulate the magnetic device without becoming inadvertently attached to the device.

Figure 52B:
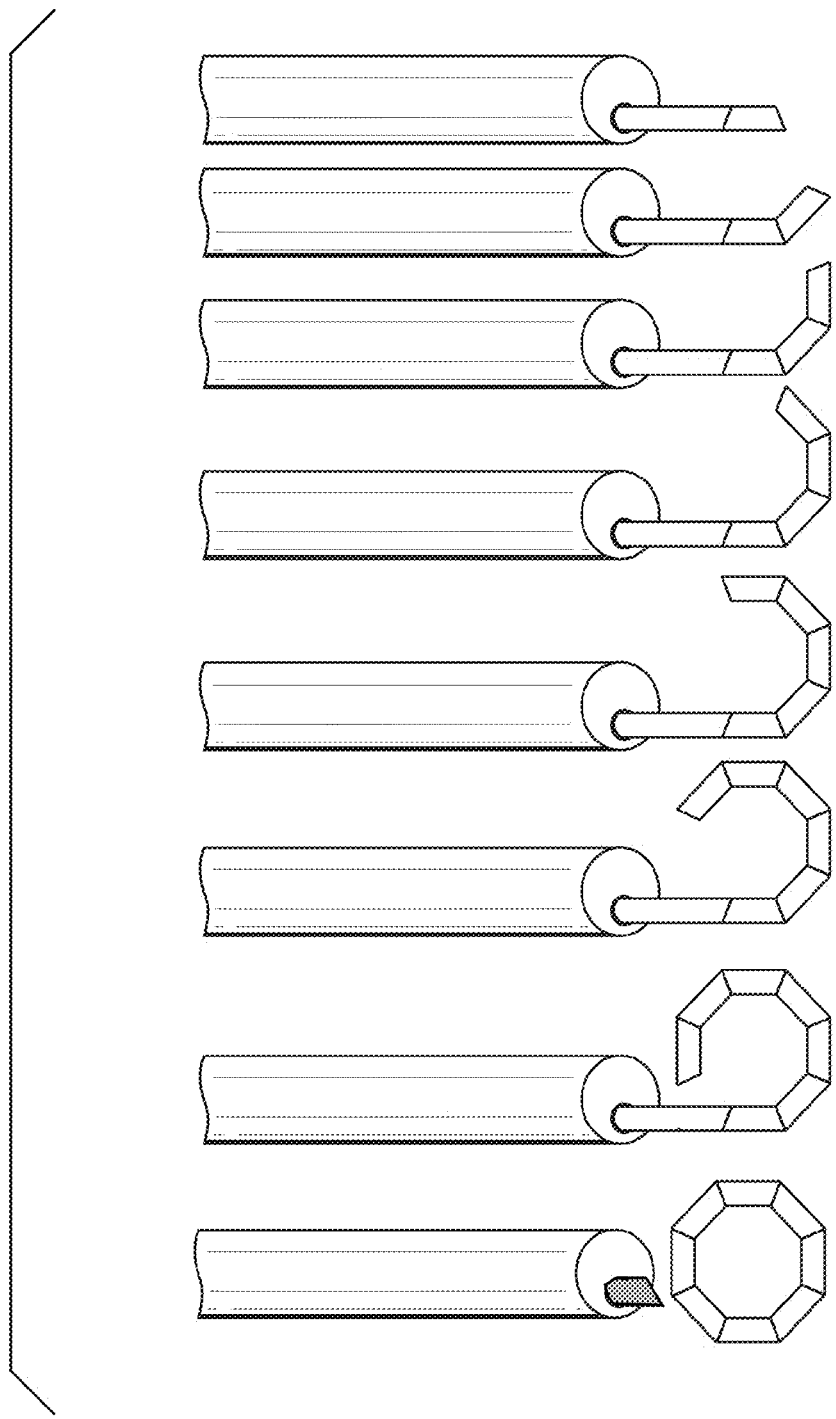
FIG. 52B shows a deployment rod with a mitered end that reversibly attaches to the proximal end of a magnetic anastomosis device during deployment.

Once deployed, magnetic anastomosis devices can be precisely delivered to the appropriate anatomical location using the deployment tool. In some embodiments, this will be accomplished with a deployment tool providing additional degrees of freedom, specifically axial displacement and rotation, about the scope axis. As described above, the distal tip of the deployment tool may be magnetic or ferromagnetic, to provide control of the magnetic device before, during, and after deployment. In some embodiments, the deployment tool tip is shaped with a miter that matches the magnetic device's proximal end, to maximize surface area and magnetic attraction, as shown in FIG. 52B. This tip profile also helps to prevent tissue from getting caught as the magnetic ring closes, because the deployment rod covers the proximal ring surface and gracefully hands the space off to the awaiting distal end of the magnetic ring, waiting to close off and complete the magnetic ring formation. To release the deployed ring from the deployment tool, the deployment tool is simply withdrawn, or the endoscope advanced, until the delivery tool pulls into the endoscopes working channel and the endoscope tip pushes on, and releases, the magnetic ring. In some procedures the deployment tool may be redeployed after it has been decoupled from the magnetic device, for example to manipulate a deployed magnetic device into the proper location. Alternatively, the deployment device can be used to locate a magnetic structure that has been place on the other side of a tissue plane, but is not visible through the endoscope.

In some embodiments, the distal tip of this deployment rod will have a heavily radiused opening that allows suture materials to pass through, e.g., as shown in FIG. 52A. The channel will typically run the length of the deployment rod. The channel can be used, for example to allow high tensile sutures to be accessed at the proximal end of the endoscope, as discussed in detail below with respect to FIGS. 53 and 54. In some embodiments, the deployment rod may comprise a radiopaque or echogenic marker to facilitate location with fluoroscopy or ultrasound, respectively.

In some embodiments, a target marker can be delivered and anchored to a precise location in the organ, structure, or lumen, where the exoskeletal structure is to be delivered. Preferably this target marker can be easily identified through endoscopic visualization, fluoroscopy, and ultrasound. Ideally this target can also be used to guide the deployed exoskeletal structure precisely into place.

Additionally, it may be necessary in some procedures to control bodily structures and/or tissues so that the device can be deployed and successfully self-assembled. That is, prior to device deployment, a region should be identified with a sufficient landing zone and sufficient deployment space. If tissue or bodily appendages come in between a structure that has not completed self-assembled, the assembly may not adequately close and properly form. In such instances, it is helpful to have a delivery device that provides isolation from a potentially challenging environment where the self-assembling device may otherwise have trouble closing. In an embodiment, a balloon can be used to provide the needed isolation, thus providing control over an otherwise challenging environment.

Figure 53:
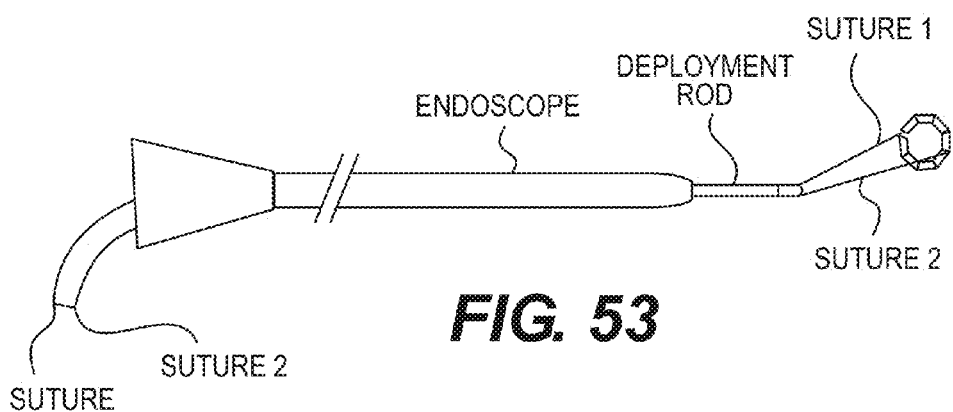
FIG. 53 illustrates how device placement can be directed by applying tension to sutures 1 and 2.
Figure 54:
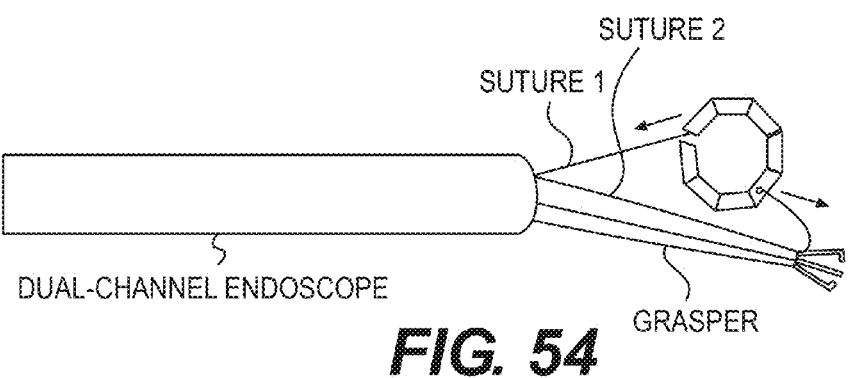
FIG. 54 shows a dual channel endoscope and the use of a grasper to remove a device by exerting force against the opposing suture attachment points.

An external structure embodiment that allows for significant maneuverability and delivery of the exoskeletal structures to precise locations is shown in FIGS. 53 and 54. As shown in FIG. 53, two high tensile sutures members are attached and integrated into the exoskeletal structure. The two tensile members are attached to the device at points 180 degrees apart. Each suture then runs through the tip of the deployment rod, through the deployment rod length, and is accessible at the proximal end of the endoscope. The tensile members can be attached to a handle or tension wheel on the proximal end, to simplify placement of the deployed device. For example, pulling on both sutures will allow a surgeon to center the deployed device. The device can also be moved left/right and rotated by manipulating the tensile members. Also, when the magnetic frame is deployed through a needle or catheter into a different organ, structure, or lumen, these integrated sutures provide the ability to pull back and assist in magnetic frame capture between two different and separated anatomical structures.

As appreciated by those of skill in the art, device placement is especially critical in certain applications, such as creation of a gallbladder anastomosis. In this situation, it is critical that the captured magnetic assembles encompass the puncture site, to ensure the area is sealed and not leaking. To ensure that the device is delivered approximately on center of the puncture site, the tensile members can be used to pull the device back and center the device to assure that the puncture site is sealed. Once the exoskeletal structure is deployed at the desired target location, the sutures can be cut.

Additionally, should an exoskeletal structure need to be removed, one or more graspers can be introduced (endoscopically or otherwise), allowing the two tensile members to be used to provide an opening force as shown in FIG. 54. As shown in FIG. 54, the lateral force created by pulling on one or more attachment points causes a reorientation of the magnetic segments with respect to each other, thereby causing the ring to open up. For example, one of the sutures can be pulled through the deployment tube while the other is pulled through a grasper, thus providing the needed opposing force. In this instance, the deployment tube can be pulled back into the endoscopic channel, thereby pulling the un-self-assembled device back into the deployment channel.

Figure 55:
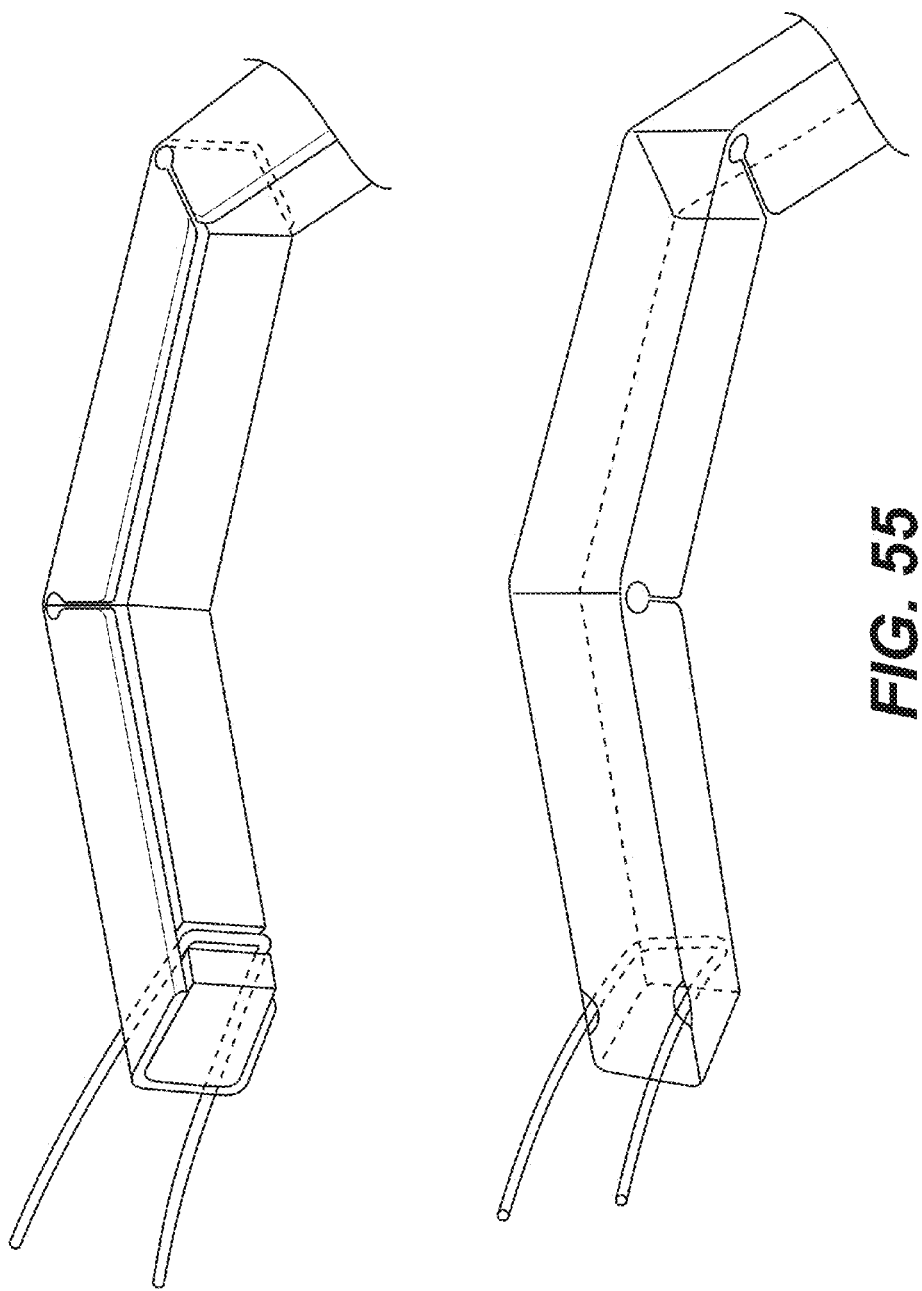
FIG. 55 shows an embodiment of a device having channels in the terminal magnet segment and holes in the exoskeleton to allow passage of a high-strength suture or other connection to provide better opening leverage.

As described above, the attachment points can be used to open a deployed and coupled magnetic anastomosis device. Because of the intense local forces required to decouple the paired magnets, the attachment points may be looped around the magnetic segments as shown in FIG. 55. As shown in FIG. 55, a channel has been cut into the magnetic segment at the proximal end of the device (distal end would look identical). The channel can be cut with, for example, a wire EDM device. The channel assures that a high-strength suture loop (e.g., Dyneema™ or Spectra™) does not move from the magnetic segment once it has been placed. The channel also assures that the force is against the magnetic segment and does not cause the end of the exoskeleton to pull free of the magnetic segment. In the design shown in FIG. 55, holes are also provided in the exoskeleton to allow passage of the suture. Other designs are also possible, for example running the suture around the exterior of the exoskeleton. In some embodiments, the suture will be knotted to form a loop, e.g., as shown in FIG. 23.

An alternative technique for separating a deployed magnetic device involves a spreading tool. The tool engages the inner surface of the ring formed by the magnetic segments. The tool can have a small amount of magnet attraction to facilitate seating on the ring magnet's inner surface. Once in place, the spreading tool expands in diameter, causing the magnetic ring to open. Once opened, securement points on the magnetic ring can be engaged, allowing the opened ring magnet to be pulled back into the endoscope channel or retrieved by a retrieval basket.

Figure 56:
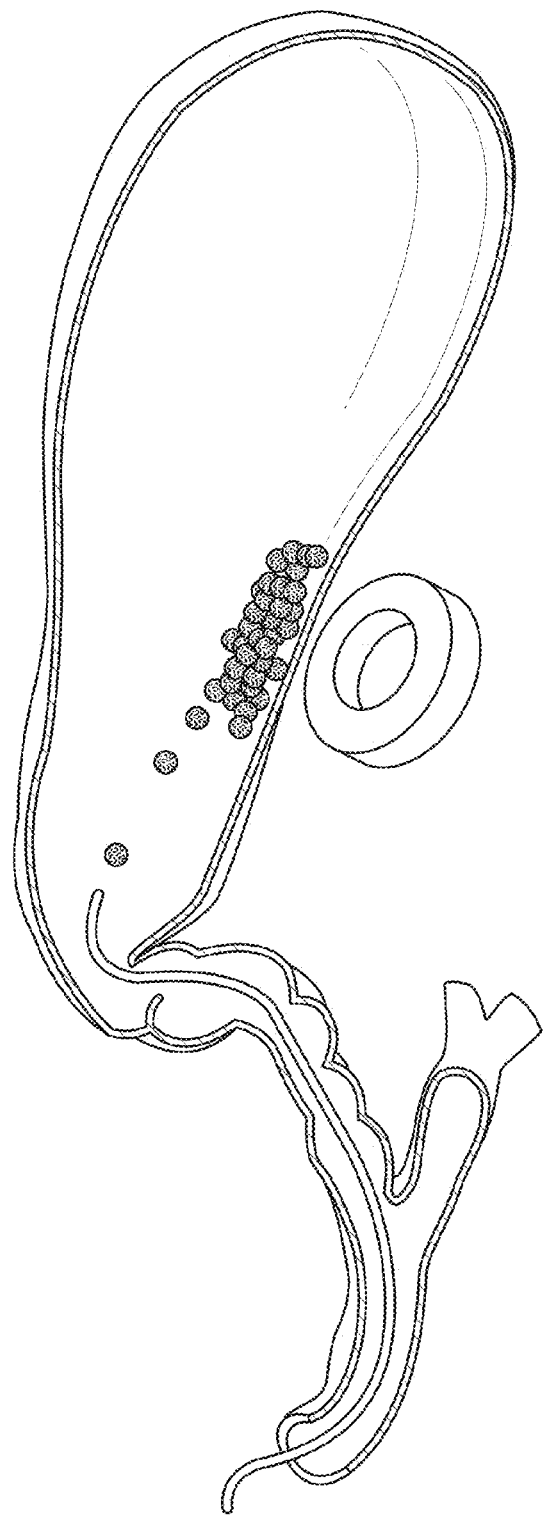
FIG. 56 is a schematic illustration of the gallbladder, generally illustrating the positioning of parent and daughter magnets to create a compression anastomosis, and particularly, the delivery of daughter magnetic material through a biliary catheter to the gallbladder.

Additional devices and procedures are discussed below. FIG. 56 is a schematic illustration of the gallbladder, showing a parent magnet on one side of the organ wall and a daughter magnet, made of a paramagnetic or ferromagnetic material, on the other side of the organ wall. In the illustrated scenario, the parent magnet resides on or is secured to the stomach wall not shown in FIG. 56). Once installed, the parent magnet and daughter magnet are left in place, with the magnetic attractive forces between them compressing the organ wall or walls, until an opening or anastomosis is created.

The parent magnet may, for example, comprise a permanent magnet such as a rare-earth disc or ring magnet (e.g., neodymium-boron-iron (NdBFe) or samarium-cobalt (SmCo) attached to a means of mucosal or tissue fixation, such as an endoscopic clip (Olympus QuickClip 2 Hemostatic Clip device, Olympus Corporation, Tokyo, Japan), via a connection, such as suture. In some embodiments, the parent magnet is large enough and of a shape appropriate to create an opening of a size and shape sufficient for an endoscope, catheter, or other surgical instrument to pass through. For example, in the embodiment of FIG. 56, the parent magnet is in the form of a disc with a diameter between 0.5 cm to 6 cm, but with a preferable diameter of 1 cm to 3 cm. This range of diametric sizes creates an anastomosis large enough to avoid stricture formation that may prohibit endoscopic access.

One advantage of systems, methods, and kits according to embodiments of the invention is that the parent magnet and the daughter magnet need not be of the same shape, size, or characteristics. For example, the parent magnet may be relatively larger and adapted for delivery using one type or size of instrument, while the daughter magnet or magnets may be of a different form and adapted for delivery using a different type of instrument.

The one or more daughter magnets or magnetic materials can include a plurality of paramagnetic or ferromagnetic steel ball-bearings or discs having a sufficient size and/or shape for delivery by syringe using air or water pressure through an endoscopic biliary catheter, or a fine needle aspiration needle. For example, the bearings or discs may small enough to be deployed endoluminally via the cystic duct or can be endoscopically injected directly into the gallbladder from an adjacent organ (e.g., the stomach) with the aid of endoscopic ultrasound (EUS) techniques, such as, for example, Endoscopic Ultrasound, Fine Needle Aspiration (EUS FNA). This technique differs from a conventional cholecystogastrostomy using T-tags because the fistula is created by means of magnetic anastomosis rather than endoscopic suturing. In an alternative embodiment, the one or more daughter magnets or magnetic materials can include a magnetic slurry or paste.

The parent and daughter magnets or magnetic materials would generally be made of a biocompatible material or coated with a biocompatible coating, such as Parylene (Specialty Coating Services (SCS), Indianapolis, Ind.) or other biocompatible coating materials, known to persons skilled in the art.

Figure 57A:
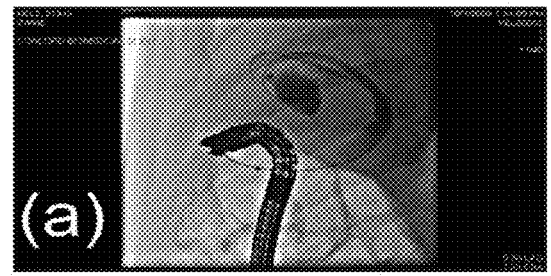
FIGS. 57A-57E are radiographic views illustrating the deployment and retrieval of parent and daughter magnets to create an anastomosis between the gallbladder and the stomach.
Figure 57B:
Figure 57C:
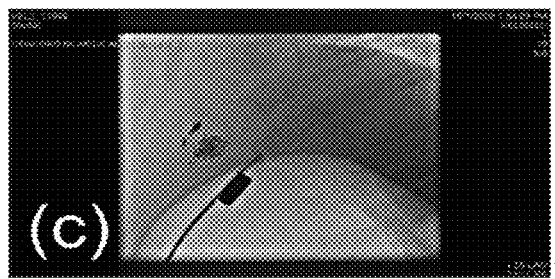
Figure 57D:
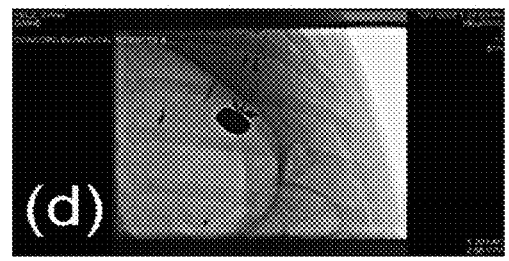
Figure 57E:
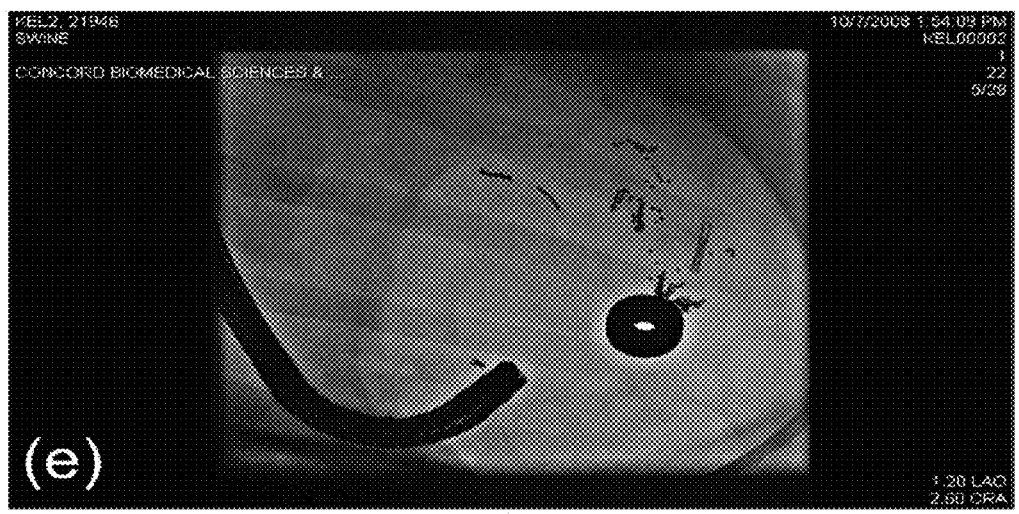

The drawings depicted in FIGS. 57A-57E are views illustrating by example, the deployment and retrieval of parent and daughter magnets to create an anastomosis between the gallbladder and the stomach. Specifically, FIGS. 57A and 57B show deployment of paramagnetic steel ball-bearings into the gallbladder via a biliary catheter. FIG. 57C shows deployment of a NdBFe parent magnet which is endoscopically clipped to the stomach wall. Capture of the bearings, shown in FIGS. 57D and 57E, by the parent magnet, results in apposition of the daughter and parent magnets for the anastomosis.

In another embodiment of the invention, the daughter magnet or magnetic material, which may be used as the intra-gallbladder component in a stomach-gallbladder anastomosis, comprises a second rare-earth magnet that can be delivered by syringe using air or water pressure through an endoscopic biliary catheter or endoscopically injected into the gallbladder from an adjacent organ (e.g., the stomach) with the aid of EUS FNA methodologies. Since the size of any one daughter element is limited by the cystic duct diameter, this embodiment may utilize a "self-assembling" structure for the magnetic elements, such that after deployment into the gallbladder, the daughter magnet's elements combine to form a larger structure, thus creating sufficient force between the parent and daughter magnets to result in anastomosis. This type of magnetic self-assembly is schematically illustrated in FIGS. 58A-58D, in which a train of daughter magnet components are injected into the gallbladder.

Figure 58C:
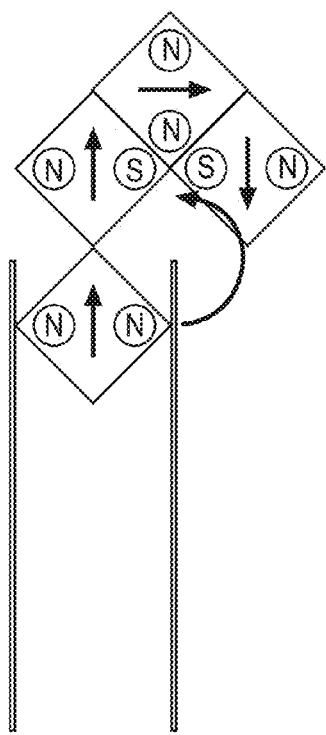
Figure 58D:
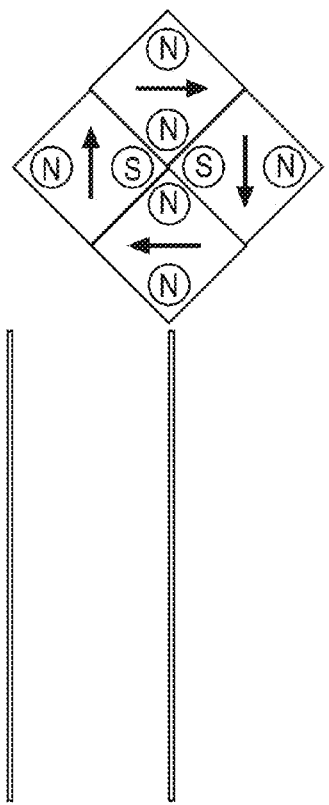

The components each carry two miniature magnets of variable magnetic polarity (e.g., north (N) or south (S)) In the case of quadrapolar magnets, three magnet component combinations are possible: (i) N-N, (ii) S-S and (iii) N-S (which is equivalent to S-N upon rotation by 180° for symmetric components). The daughter magnet components are small enough to fit through the inner diameter of the biliary catheter or EUS FNA device or FNA needle, Careful selection of the injection sequence can yield a larger planar surface upon self-assembly within the gallbladder than would be possible with any single component. The large daughter magnet in FIG. 58D is assembled by means of the following magnet component sequence (leftmost polarity first): N-S, NN, N-S, N-N. FIGS. 58A-58D represent the simplest example of magnetic self-assembly, and a much larger number of daughter magnet components can be used in practice to provide sufficient mating area with the parent magnet in the small intestine or stomach wall for effective anastomosis.

Figure 59:
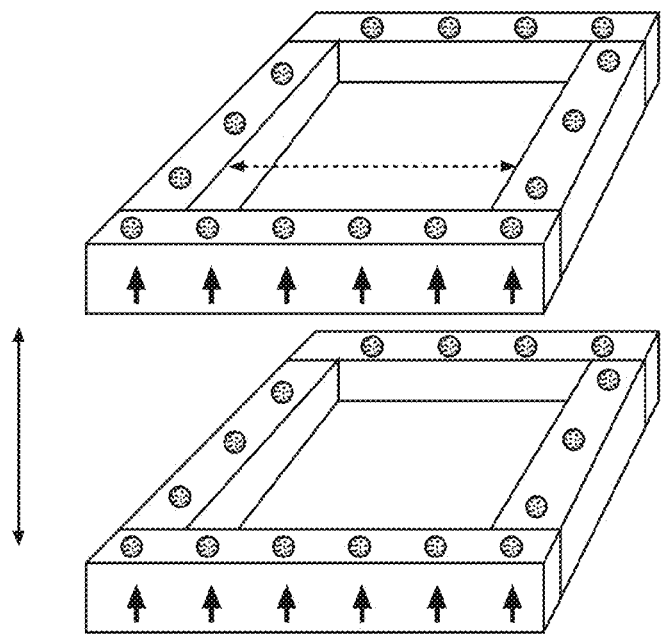
FIG. 59 depicts the arrangement for self-alignment between assembled parent and daughter magnets using north/south attractive magnet forces.

The simplest embodiment of a self-assembling magnet results from a dipolar train of free (i.e. unconnected) rectangular or cylindrical magnets extruded into space where the direction of magnetic polarization is perpendicular to the direction of extrusion and the magnetization direction increases in consecutive components by 90° with each. For four rectangular components, where the direction of magnetization of consecutive components is 0°, 90°, 180° and 270° in the plane perpendicular to extrusion, the resultant assembly will be a four-sided rectangle (or a square in the case of identical components), as shown in FIG. 59. If this first magnetic train comprises the daughter magnet and a second, identical magnetic assembly comprises the parent magnet then mating occurs when the two opposing pole faces (i.e., north and south in the case of FIG. 59) come into proximity and the magnetic attractive forces between the two assemblies cause compressive attraction between the parent and daughter magnets. This compressive attraction which acts to compress the intervening gastric and gall bladder walls is theoretically sufficient to produce a leak-free magnetic anastomosis within a period of three to five days. The resultant window of access is accessed by means of needle-knife incision or similar endoscopic cautery, known to persons skilled in the art.

FIG. 59 shows the arrangement for self-alignment between assembled parent and daughter magnets, using purely north/south attractive magnet mating. This configuration is suitable for generating significant compressive force sufficient for the creation of magnetic anastomosis using NdFeB magnetic components. However, to avoid repulsion between the parent and daughter assemblies, the opposing faces (i.e., north/south) need to be in closest contact.

Figure 60:
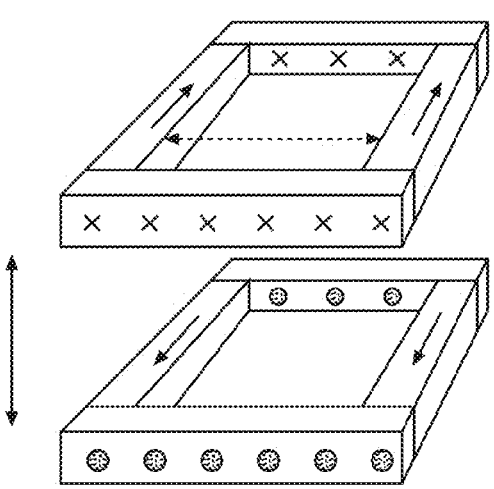
FIG. 60 depicts the arrangement for self-alignment between assembled parent and daughter magnets, using "east/west" attractive magnetic forces.
Figure 61A:
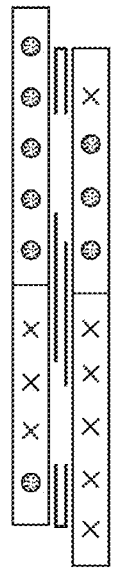
FIGS. 61A-61D illustrates the concept of "Magnet Self Assembly" in a connected train of magnetic components including a combination of quadruple and dipole components.
Figure 61B:
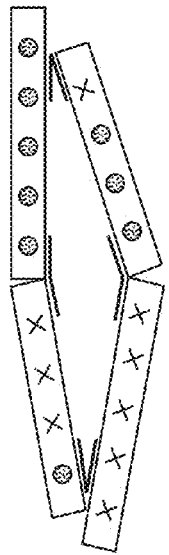
Figure 61C:
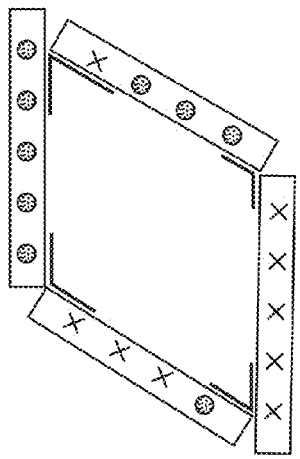
Figure 61D:
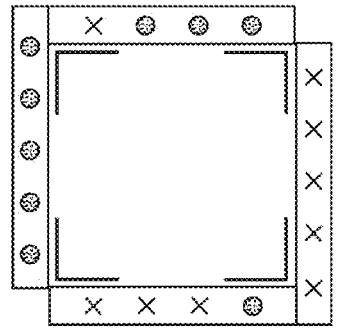

FIG. 60 shows the arrangement for self-alignment between assembled parent and daughter magnets, using what we term "east/west" attractive magnetic forces. This attraction takes advantage of the necessity for magnetic flux lines to form closed paths leading to a strong compressive force between the parent and daughter assemblies. While necessarily less than the compressive force for purely N/S attraction, this configuration may also be suitable for generating significant compressive force sufficient for the creation of magnetic anastomosis using NdFeB magnetic components when the separation distance is small (<1 mm) and high grade magnetic components (e.g., N50 or higher) are employed. The advantage of this configuration is that compression occurs independent of which faces are in contact and self-alignment is again achieved.

FIG. 61 illustrates the concept of "Magnet Self Assembly" in a connected train of magnetic components. When a combination of quadruple and dipole components are employed, a repulsive magnetic force can be used to ensure self-assembly. As shown in FIG. 61, the self-assembly is due to the repulsive forces associated with neighboring S poles (indicated by the solid circles) in the upper two components and the neighboring N poles (indicated by the crosses) in the lower two components which, together, drive the assembly into the final four-sided window.

In an alternate embodiment of the present invention, the intra-gallbladder daughter material may comprise a (super) paramagnetic fluid consisting of iron-oxide particles or a suspension of iron filings. In the presence of the parent magnet, the (super)paramagnetic fluid would be strongly attracted to the parent magnet again, resulting in anastomosis due to the pressure between the two surfaces.

When external magnets are applied to the ferromagnetic daughter material they can be permanently magnetized to enhance the force of attraction between the parent magnet and the daughter material.

In the case of a stomach-gallbladder anastomosis, the parent magnet may be placed on the lumen of the small intestine or on the stomach wall using an endoscope that is introduced per-orally. The parent magnet may be fixed to the mucosa of the small intestine or stomach using an endoscopic clip.

One method for deploying the daughter magnet or magnetic material would involve using the standard Endoscopic Retrograde Cholangiopancreatography (ERCP) technique and fluoroscopy, in which a biliary catheter is introduced over a guidewire into the gallbladder. The ball-bearings or other daughter magnetic material would be delivered to the gallbladder through the biliary catheter using air pressure or liquid pressure provided by syringe. Alternatively, the daughter magnet or magnetic material may be deployed by direct injection from an adjacent organ into the gallbladder with the aid of EUS FNA type systems.

Figure 62:
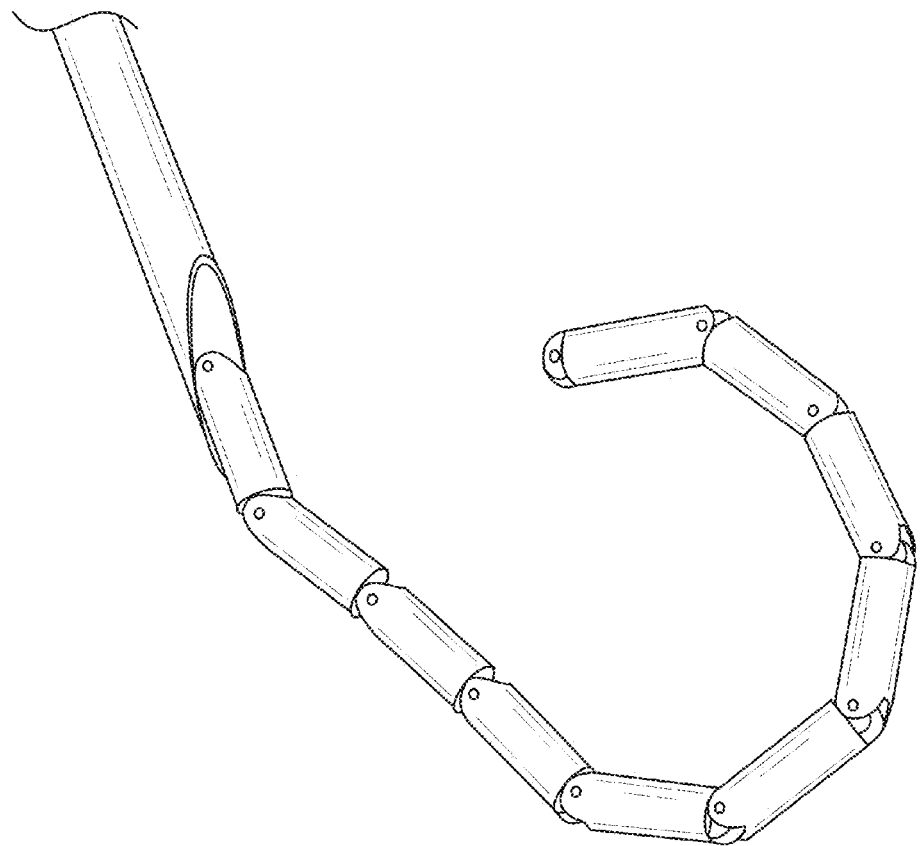
FIG. 62 depicts the extrusion of magnet components arranged in "North-South" arrangement from a fine needle aspiration (FNA) needle.
Figure 63:
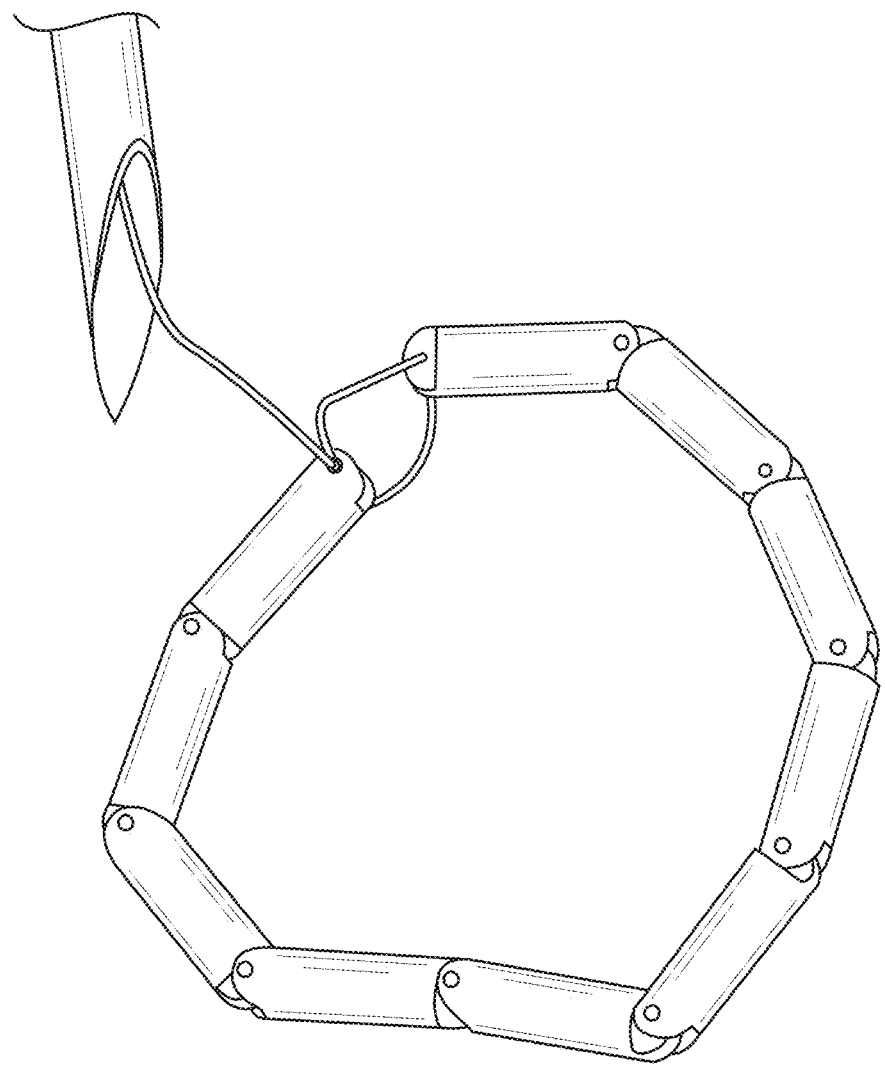
FIG. 63 depicts the self-assembly of the magnetic components depicted in FIG. 62 after extrusion from FNA needle and the use of a suture to connect the magnetic components.
Figure 64:
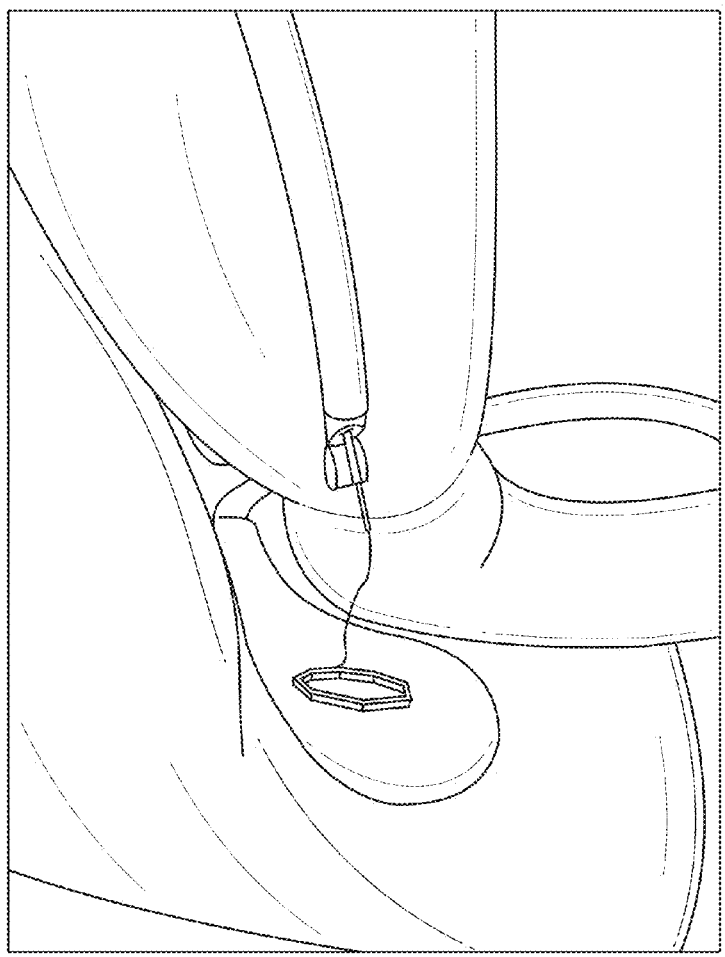
FIG. 64 depicts the deployment of daughter magnets from the stomach into the gallbladder using endoscopic ultrasound, the assembly of the daughter magnets in the gallbladder, and the positioning of a suture in the stomach upon retraction of the endoscopic ultrasound scope.
Figure 65:
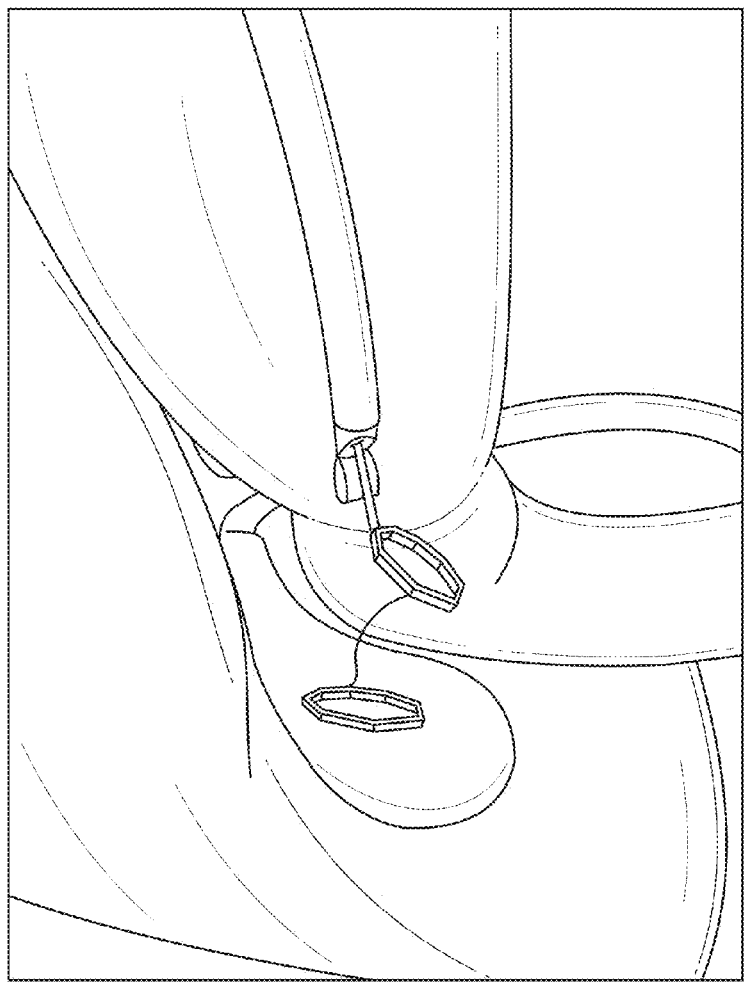
FIG. 65 depicts the assembly of daughter magnets in the gallbladder, the deployment and assembly of a parent magnet in the stomach, and the positioning of a suture connecting the daughter magnet assembly and the parent magnet assembly.
Figure 66:
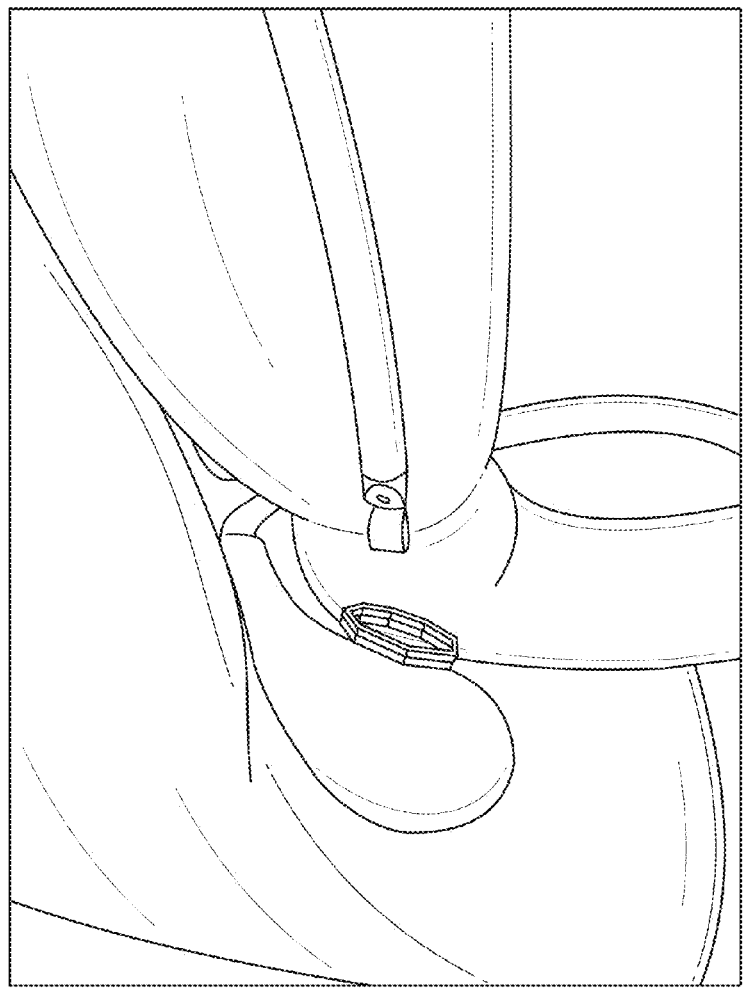
FIG. 66 depicts the magnetic attraction of daughter magnet assembly positioned against the wall of a gallbladder and a parent magnet positioned against an adjacent stomach wall.

As previously stated, the magnets may be delivered from one organ (e.g., the stomach) into another adjacent organ (e.g., the gallbladder) via a Fine Needle Aspiration (FNS) needle as illustrated in FIGS. 62 and 63. In this alternate embodiment, the individual magnets are circular in nature and pre-assembled in a N-S arrangement and injected through the inner lumen of the needle under endoscopic ultrasound guidance. These magnets may also be polarized in a N-S arrangement around the circumference of the magnet to provide for a means of apposition with the parent magnet once positioned. The distal and proximal magnets are pre-loaded with a suture through the distal and proximal eyelets of the distal and proximal magnet elements respectively. Once injected through the needle or biliary catheter, the distal and proximal magnet elements are secured together by tying off the pre-attached suture. As shown in FIG. 64, the suture is connected at the distal end to the deployed magnetic daughter assembly and runs antegrade through the inner lumen of the aspiration needle or biliary catheter. Once the needle is retracted through the wall of the stomach, the suture remains connected at the proximal end to the parent magnet assembly as shown in FIGS. 64 and 65. Once the parent magnet has been deployed into the stomach or other organ, both daughter and parent magnets are pushed together to great a tissue apposition between gallbladder and stomach as shown in FIG. 66.

Once deployed, magnet fixation is then achieved using EUS-guided T-tag delivery through the gallbladder wall with a second attachment to parent magnet in the stomach or small intestine, ensuring lock-in of parent magnet to the daughter. Such a T-tag procedure is well known to persons skilled in the art of therapeutic endoscopy. Using fluoroscopic guidance, magnetic attraction between the parent magnet and the intra-gallbladder ball-bearings can then be confirmed.

When the parent and daughter magnets are left in place for a period of time, the compressive forces on the tissue between the two magnets causes the tissue to necrose, leaving an opening surrounded by a fibrotic or collagenous border. After a period of several days (3-15), the creation of an opening, such as a cholecystogastrostomy, can be confirmed by upper endoscopy or another such technique. At that time, the cholecystogastrostomy can be traversed using the upper endoscope for the purpose of mucosal ablation. Mucosal ablation may be achieved using argon plasma coagulation (APC), electrocautery, laser, or instillation of sclerosant (e.g. alcohol or ethanolamine or sodium morrhuate). A prophylactic biliary stent may optionally be placed by endoscopic retrograde cholangiopancreatography (ERCP) prior to gallbladder mucosal ablation.

The purpose of gallbladder ablation is to induce scarring down of the gallbladder (i.e. functional cholecystectomy). This can be confirmed with a follow-up endoscopy or by radiographic (e.g. oral contrast study) or nuclear medicine study (e.g. biliary scintigraphy or HIDA study).

Aspects of the invention relate to a surgical kit or kits that contain all the additional, specialized surgical tools used to perform the tasks described above. For example, surgical kits of the invention at least include a parent magnet as described herein, and one or more daughter magnets as described herein, loaded into an introduction device such as a biliary catheter or an endoscopic instrument (e.g., EUS FNA needle and/or system). In one embodiment, the kit(s) of the invention include, but are not limited to, (i) the parent magnet in a suitable biocompatible enclosure (e.g., Parylene or biocompatible plastic) and (ii) the daughter magnet material, preloaded for deployment. Optionally, the kit(s) of the invention include a grasping snare or pinchers for assisting with the introduction and placement of the parent and/or daughter magnets.

For embodiments or situations in which the daughter magnet or magnetic material is injected directly into the gallbladder (either by transgastric means or via the small intestine wall), the daughter magnetic material may be preloaded in an EUS FNA injection needle with an outer diameter in the range of 10 Gauge to 25 Gauge, but more preferably in the range of 15 Gauge to 20 Gauge. Deployment of both magnets into the gallbladder and/or stomach can be achieved with the aid of EUS FNA is this instance.

It should be noted that the present invention is not limited to the clinical applications listed in the afore-described disclosure. The technology as per the disclosed description may also be utilized to achieve an anastomosis between other adjacent organs in both the upper and lower gastrointestinal tracts such as, but not limited to, between the small intestine/gallbladder, the stomach/duodenum and the ileum/colon for bariatric/metabolic purposes. The daughter and parent magnet components may be delivered during simultaneous endoscopy and colonoscopy procedures and mated under fluoroscopy. The afore-mentioned endoscopy and colonoscopy procedures are well known to persons skilled in the art of therapeutic endoscopy.

While the invention has been described with respect to certain embodiments, the embodiments are intended to be exemplary, rather than limiting. Modifications and changes may be made within the scope of the appended claims,

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. An implantable device comprising:
a plurality of magnetic segments; and
an exoskeleton that covers a portion of the exterior of each of the magnetic segments,
wherein the exoskeleton is adapted to direct the magnetic segments to self-assemble into a geometric shape.

2. The implantable device of claim 1, wherein the magnetic segments are elongated and are coupled end-to-end to each other by the exoskeleton.

3. The implantable device of claim 2, wherein the exoskeleton is deformable to allow the magnetic segments to be aligned linearly.

4. The implantable device of claim 1, wherein the exoskeleton comprises a shape metal alloy.

5. The implantable device of claim 4, wherein the shape memory metal comprises a nickel alloy, a copper alloy, a zinc alloy, a platinum alloy, or a cobalt alloy.

6. The implantable device of claim 4, wherein the shape memory metal comprises a nickel-titanium alloy.

7. The implantable device of claim 1, wherein the device self-assembles into a geometric shape that is angular, polygonal, or spiral.

8. The implantable device of claim 7, wherein the device comprises four or more magnetic segments and the device self-assembles into a polygon.

9. The implantable device of claim 8, wherein the polygon is a square, a hexagon, or an octagon.

10. The implantable device of claim 8, wherein a magnetic pole of each segment is normal to the face of the polygon.

11. The implantable device of claim 8, wherein the distance across the polygon, measured through the center of the polygon, is 5 mm or greater.

12. The implantable device of claim 8, wherein the distance across the polygon, measured through the center of the polygon, is 5 cm or less.

13. The implantable device of claim 1, wherein the magnetic segments comprise rare earth magnets.

14. The implantable device of claim 13, wherein the magnetic segments comprise neodymium magnets.

15. The implantable device of claim 1, wherein the magnetic segments comprise a trapezoidal face.

16. The implantable device of claim 1, further comprising an attachment point.

17. The implantable device of claim 16, wherein applying a force to the attachment point allows the magnetic segments to be re-oriented with respect to each other.

18. The implantable device of claim 16, wherein the attachment point comprises suture.

19. The implantable device of claim 18, wherein the suture is biodegradable.

20. The implantable device of claim 1, wherein the exoskeleton directs the magnetic segments from a linear configuration to a polygon configuration when the device is delivered from a lumen.

21. The implantable device of claim 1, wherein the magnetic segments have a rectangular or square cross section and the exoskeleton covers three of the four sides.

22. The implantable device of claim 1, wherein the exoskeleton provides a substantially continuous smooth surface on the annular face of the geometric shape.

23. The implantable device of claim 1, wherein the exoskeleton limits the magnetic segments to moving in a plane defined by the geometric shape.

* * * * *